(12) United States Patent
Wang et al.

(10) Patent No.: US 11,471,057 B2
(45) Date of Patent: Oct. 18, 2022

(54) SINGLE-IMPULSE PANORAMIC PHOTOACOUSTIC COMPUTED TOMOGRAPHY (SIP-PACT)

(71) Applicant: WASHINGTON UNIVERSITY, St. Louis, MO (US)

(72) Inventors: Lihong Wang, St. Louis, MO (US); Lei Li, St. Louis, MO (US); Liren Zhu, St. Louis, MO (US); Cheng Ma, St. Louis, MO (US)

(73) Assignee: Washington University, St. Louis, MO (US)

( * ) Notice: Subject to any disclaimer, the term of this patent is extended or adjusted under 35 U.S.C. 154(b) by 622 days.

(21) Appl. No.: 16/464,958

(22) PCT Filed: Nov. 29, 2017

(86) PCT No.: PCT/US2017/063764
§ 371 (c)(1),
(2) Date: May 29, 2019

(87) PCT Pub. No.: WO2018/102446
PCT Pub. Date: Jun. 7, 2018

(65) Prior Publication Data
US 2019/0307334 A1 Oct. 10, 2019

Related U.S. Application Data

(60) Provisional application No. 62/427,470, filed on Nov. 29, 2016.

(51) Int. Cl.
*A61B 5/00* (2006.01)
*G01N 29/24* (2006.01)
(Continued)

(52) U.S. Cl.
CPC .......... *A61B 5/0095* (2013.01); *A61B 5/0091* (2013.01); *A61B 5/024* (2013.01);
(Continued)

(58) Field of Classification Search
CPC ..... A61B 5/0095; A61B 5/318; A61B 5/0091; A61B 5/024; A61B 5/113; A61B 5/721;
(Continued)

(56) References Cited

U.S. PATENT DOCUMENTS 10,105,061 B2 10/2018 Tanaka et al.
2008/0170771 A1 7/2008 Yamagata et al.
(Continued)

FOREIGN PATENT DOCUMENTS

CN 102727259 A 10/2012
CN 104586353 A 5/2015
(Continued)

OTHER PUBLICATIONS

European Extended Search Report regarding European Patent Application No. 17877185.3 dated Oct. 16, 2020, pp. 1-15.
(Continued)

*Primary Examiner* — Amelie R Davis
*Assistant Examiner* — John Denny Ll
(74) *Attorney, Agent, or Firm* — Armstrong Teasdale LLP

(57) ABSTRACT

A single-impulse panoramic photoacoustic computed tomography (SIP-PACT) system for small-animal whole-body imaging is disclosed. In addition, a dual-speed of sound image universal back-projection reconstruction method is disclosed. Further, a PACT system for imaging a breast of a subject is disclosed.

20 Claims, 35 Drawing Sheets

(51) Int. Cl.
  *G06T 11/00* (2006.01)
  *G01N 29/06* (2006.01)
  *A61B 5/113* (2006.01)
  *G01N 21/47* (2006.01)
  *A61B 5/024* (2006.01)
  *G01N 21/17* (2006.01)
  *A61B 5/318* (2021.01)

(52) U.S. Cl.
  CPC .............. *A61B 5/113* (2013.01); *A61B 5/318* (2021.01); *A61B 5/721* (2013.01); *G01N 21/1702* (2013.01); *G01N 21/4795* (2013.01); *G01N 29/06* (2013.01); *G01N 29/0672* (2013.01); *G01N 29/2418* (2013.01); *G06T 11/006* (2013.01); *A61B 2562/0247* (2013.01); *G01N 2291/02475* (2013.01); *G06T 2211/421* (2013.01)

(58) Field of Classification Search
  CPC ....... A61B 2562/0247; G01N 21/1702; G01N 21/4795; G01N 29/06; G01N 29/0672; G01N 29/2418; G01N 2291/02475; G06T 11/006; G06T 2211/421
  USPC .......................................................... 600/407
  See application file for complete search history.

(56) References Cited

U.S. PATENT DOCUMENTS

| | | | | |
|---|---|---|---|---|
| 2009/0105582 A1* | 4/2009 | Dougherty | ......... | G01R 33/4824 600/420 |
| 2012/0275262 A1 | 11/2012 | Song et al. | | |
| 2013/0217995 A1 | 8/2013 | Kruger | | |
| 2013/0312526 A1* | 11/2013 | Oishi | ..................... | A61B 8/406 73/620 |
| 2015/0119680 A1 | 4/2015 | Tanaka et al. | | |
| 2016/0242651 A1 | 8/2016 | Wang et al. | | |
| 2017/0311810 A1 | 11/2017 | Nakamura | | |
| 2018/0000351 A1* | 1/2018 | Zharov | ............. | G01N 15/1056 |

FOREIGN PATENT DOCUMENTS

| | | | | |
|---|---|---|---|---|
| CN | 105686799 A | 6/2016 | | |
| EP | 1063920 B1 | 11/2006 | | |
| JP | 2002506666 A | 3/2002 | | |
| JP | 2006263282 A | 10/2006 | | |
| JP | 2008194456 A | 8/2008 | | |
| JP | 2015500064 A | 1/2015 | | |
| JP | 2016087220 A | 5/2016 | | |
| RU | 2486501 C2 | 6/2013 | | |
| WO | 2015073523 A1 | 5/2015 | | |
| WO | WO-2015073523 A1 * | 5/2015 | .......... | A61B 5/0095 |
| WO | 2012108172 A1 | 12/2015 | | |

OTHER PUBLICATIONS

International Search Report for International Application No. PCT/US2017/063764, dated Jun. 21, 2018, 1 page.

Anastasio et al., "Half-Time Image Reconstruction in Thermoacoustic Tomography," IEE Transactions on Medical Imaging, 24(2): 199-210 (2005).

Chung, "SonixDAQ Hardware Signal Chain and the Imaging Parameters," Ultrasonic Medical Corporation, retrieved online at http://www.ultrasonix.com/wikisonix/index.php?title=SonixDAQ_Hardware&oldid=9306, Revision A, Feb. 4, 2011 (7 pages).

Xu et al., "Universal Back-Projection Algorithm for Photoacoustic Computed Tomography," Physical Review E, 71: 016706-1 to 016706-7 (2005).

Partial European Search Report issued for European Application No. 17877185 dated Jun. 30, 2020 (17 pages).

* cited by examiner

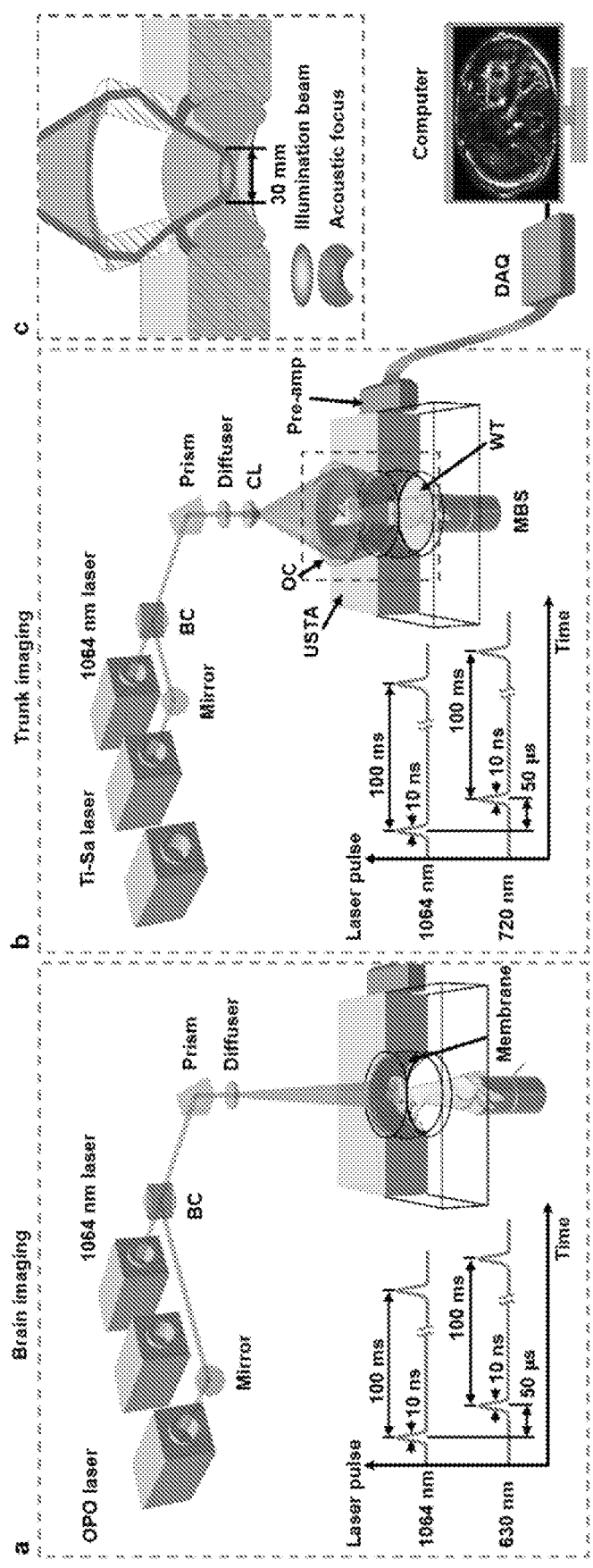

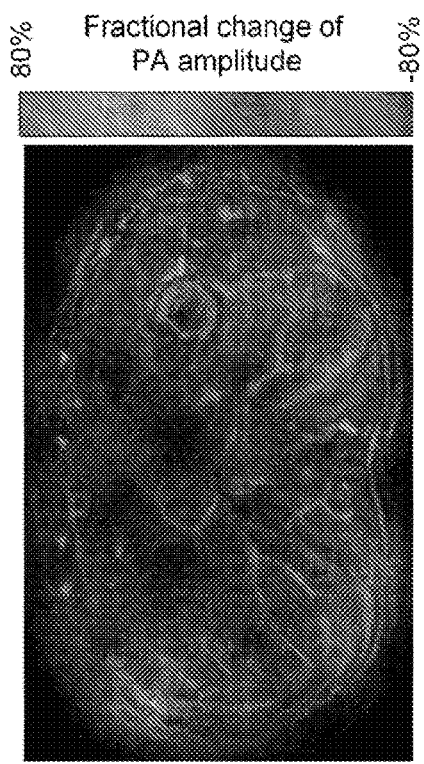
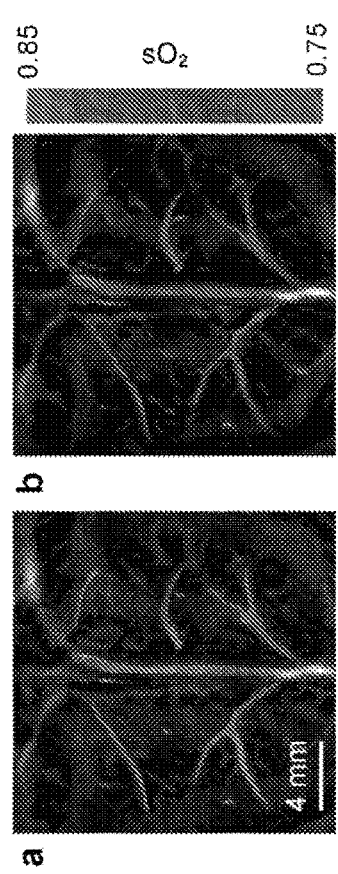
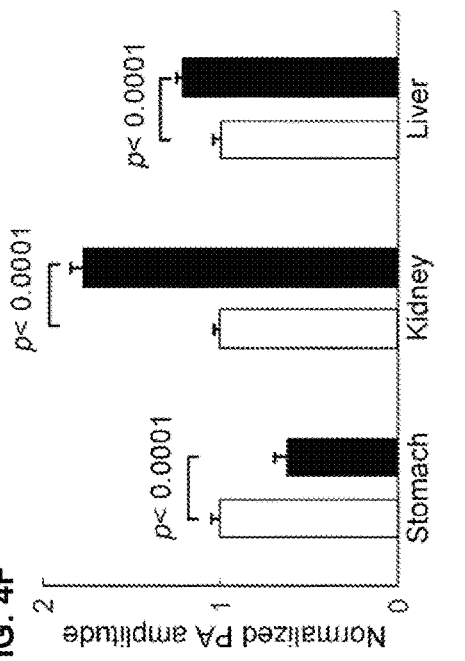
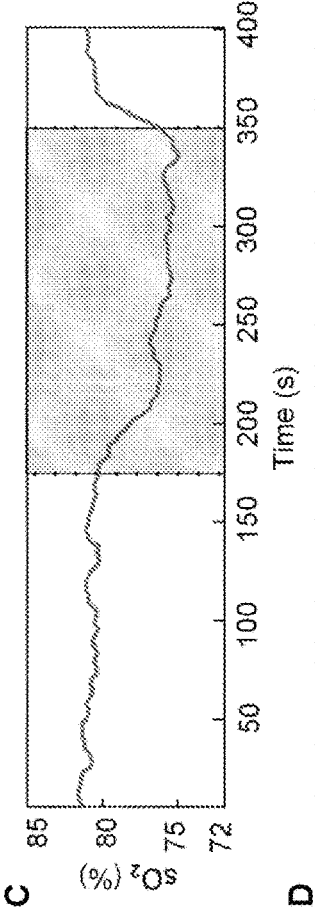
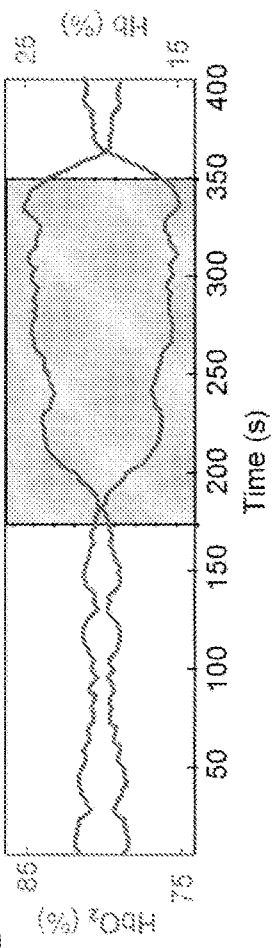
FIG. 4A  FIG. 4B  FIG. 4E
FIG. 4C  FIG. 4D  FIG. 4F

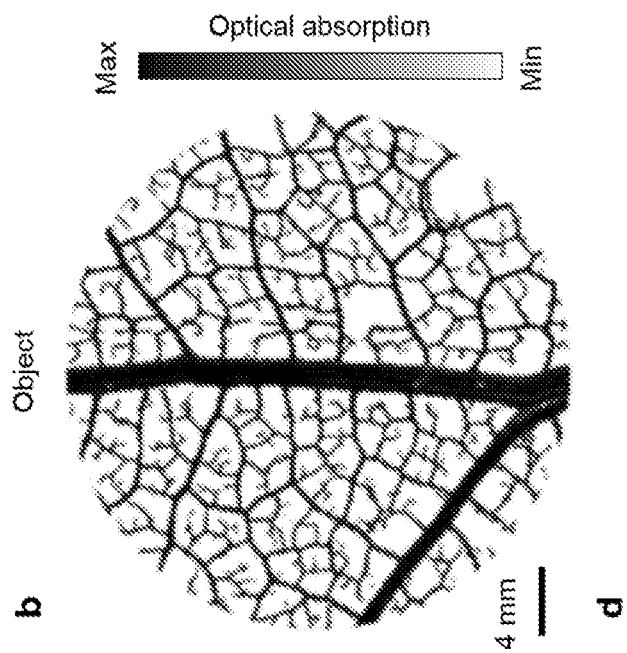
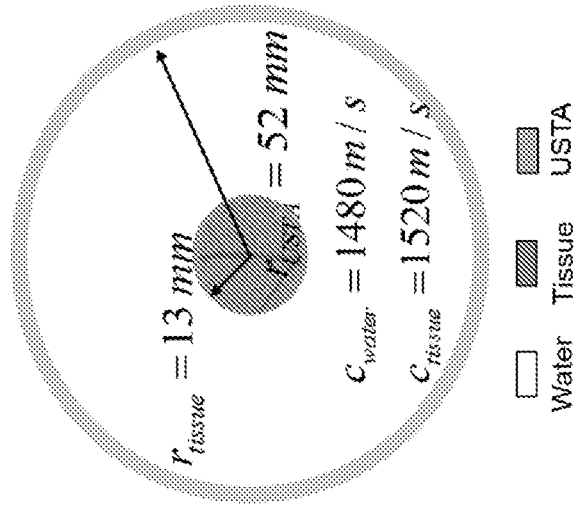
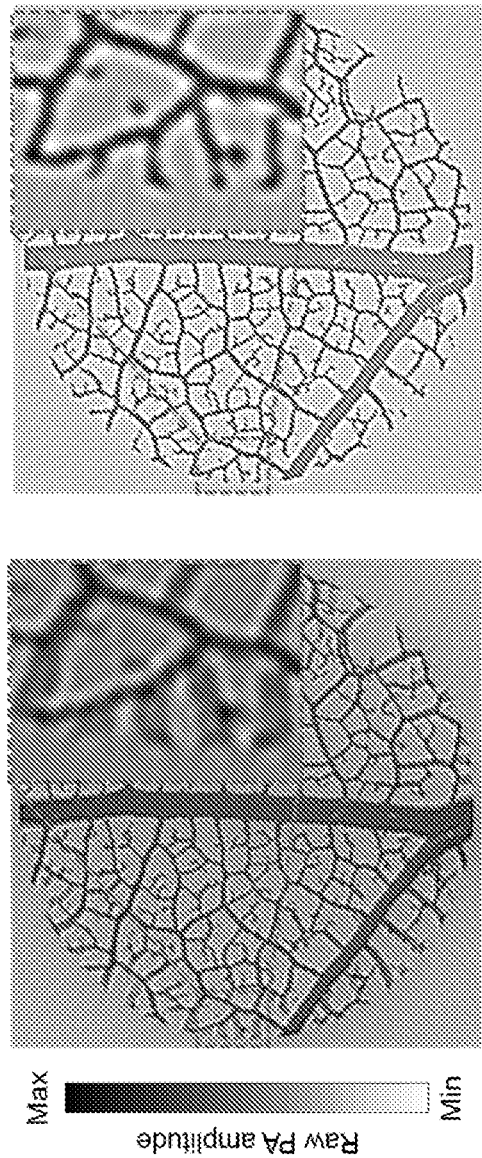
FIG. 9A  FIG. 9B  FIG. 9C  FIG. 9D

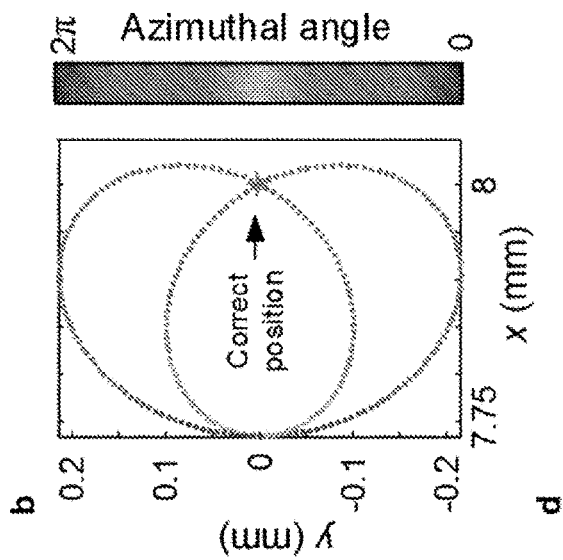
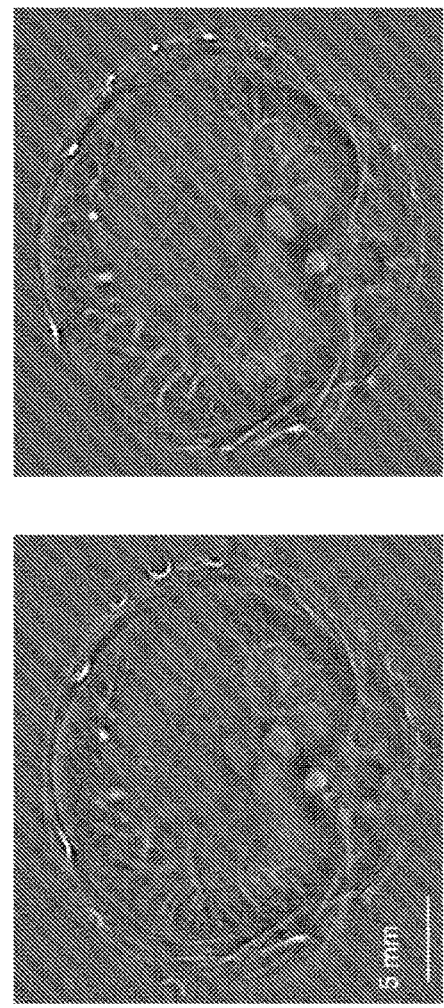
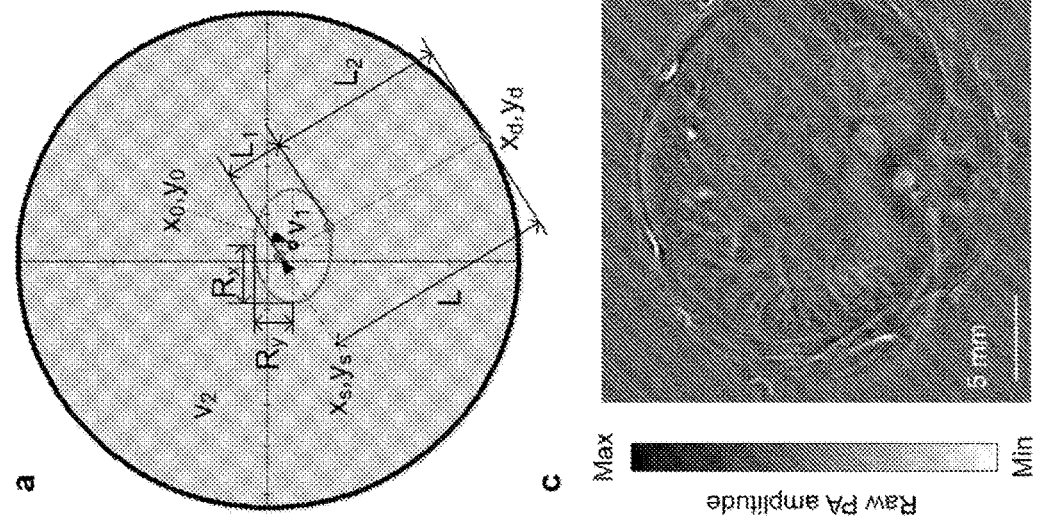
FIG. 10A  FIG. 10B  FIG. 10C  FIG. 10D

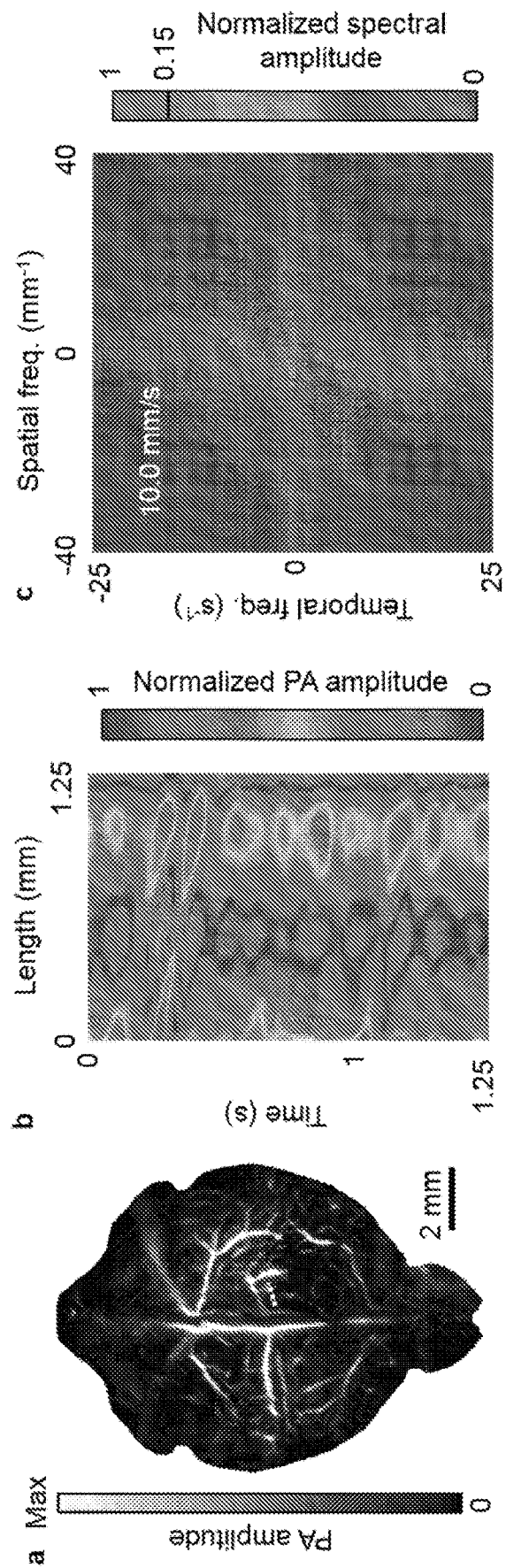

FIG. 15A
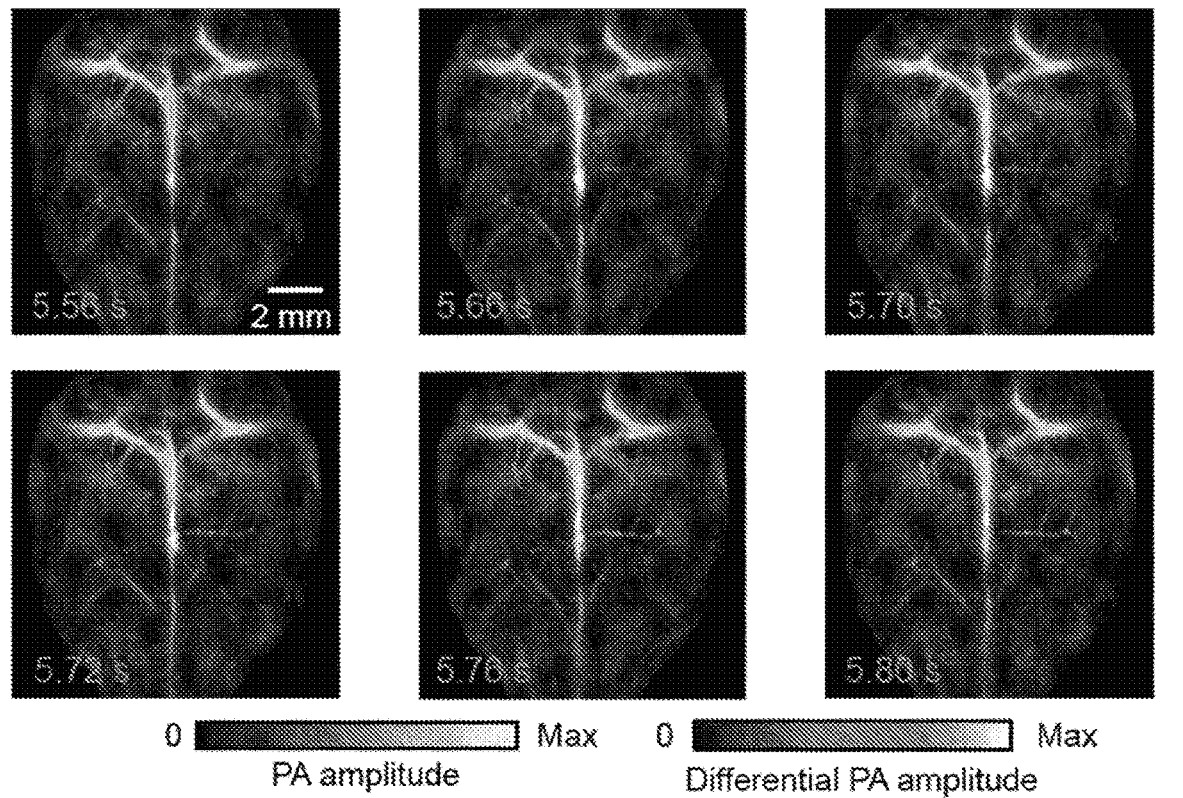
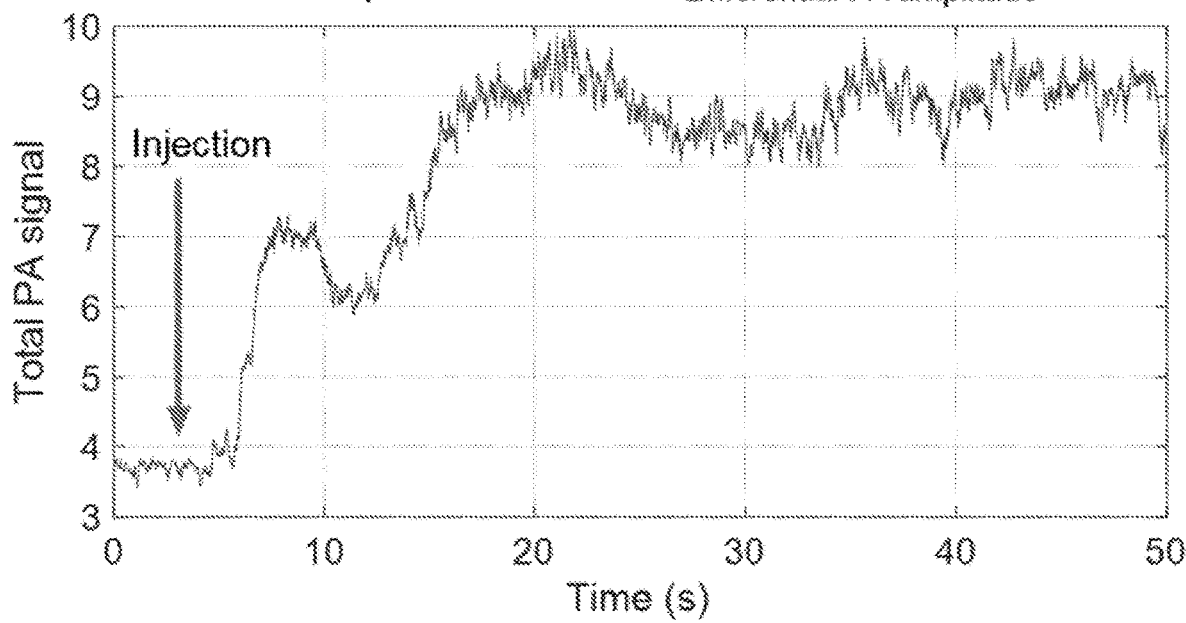
FIG. 15B

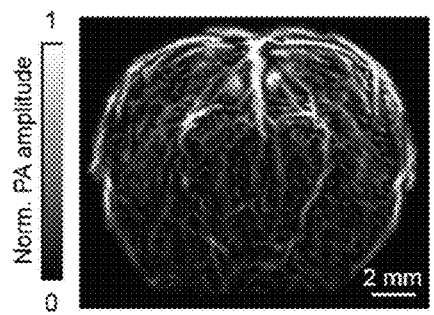 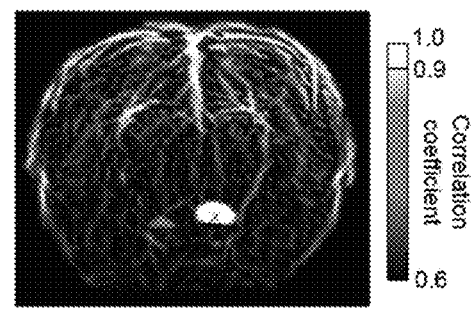
FIG. 24A  FIG. 24B
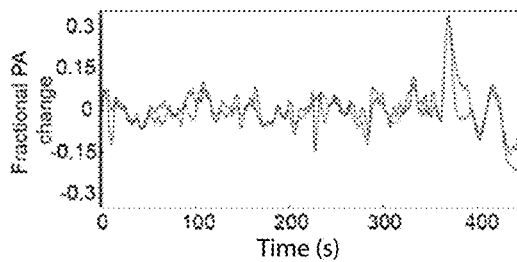 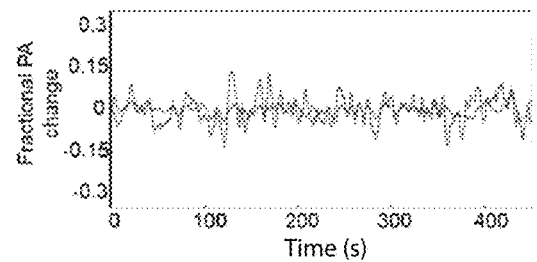
FIG. 24C  FIG. 24D
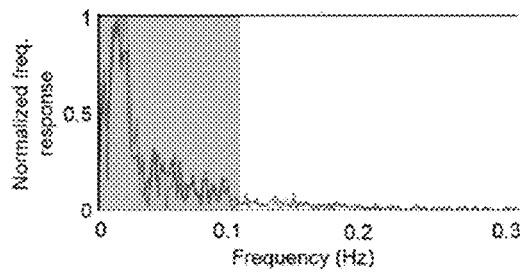 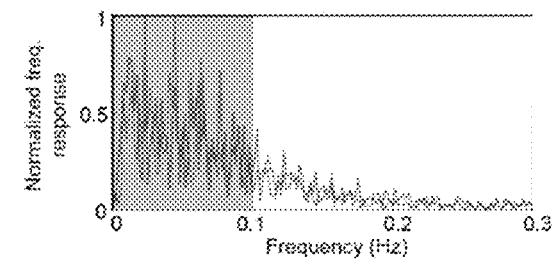
FIG. 24E  FIG. 24F
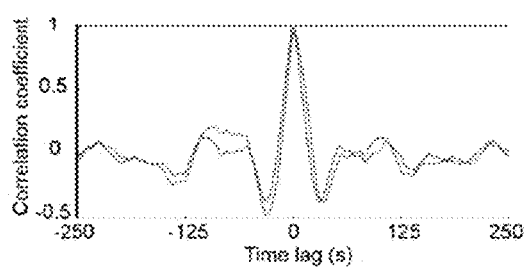 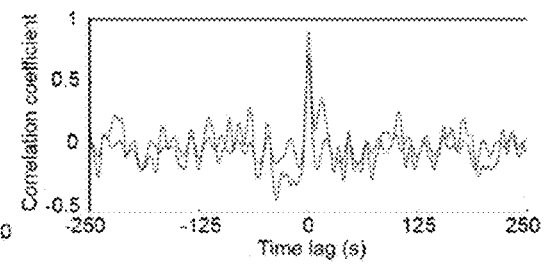
FIG. 24G  FIG. 24H

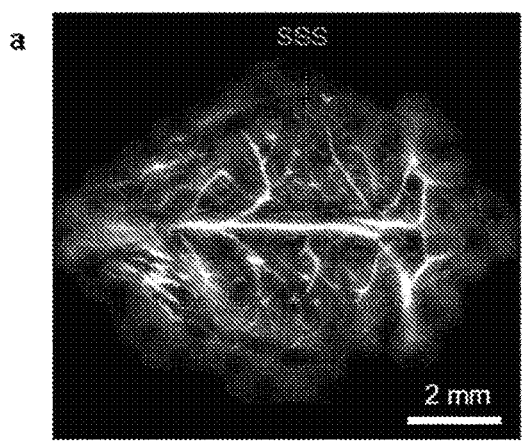
FIG. 26A
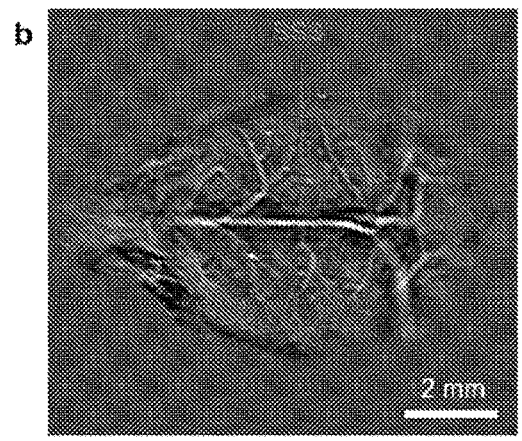
FIG. 26B
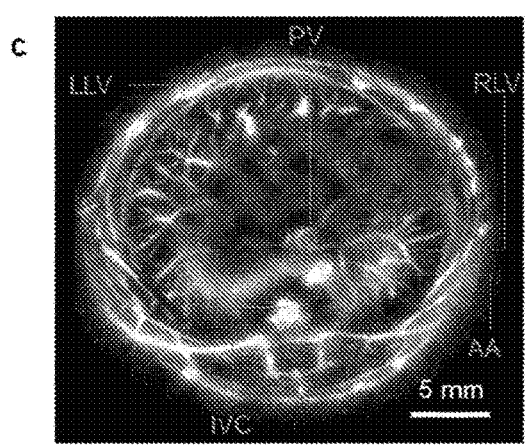
FIG. 26C
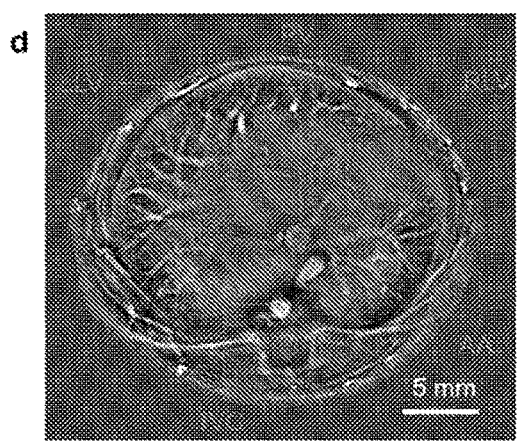
FIG. 26D
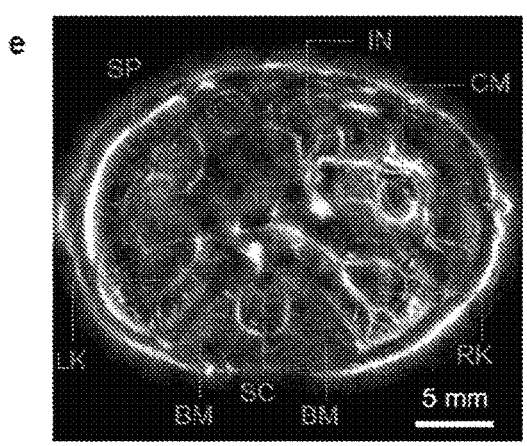
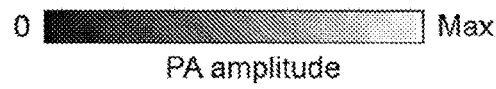
FIG. 26E
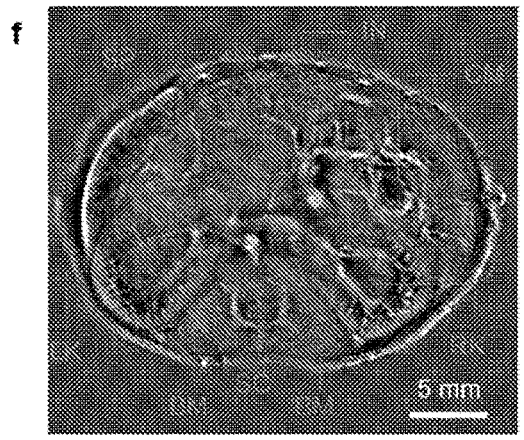
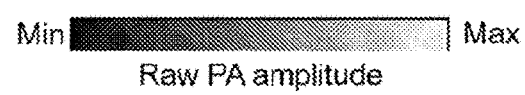
FIG. 26F

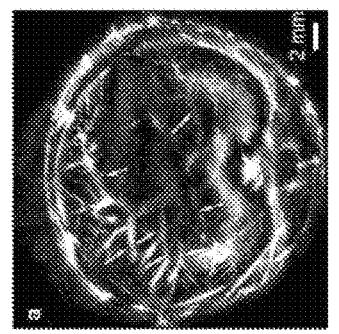
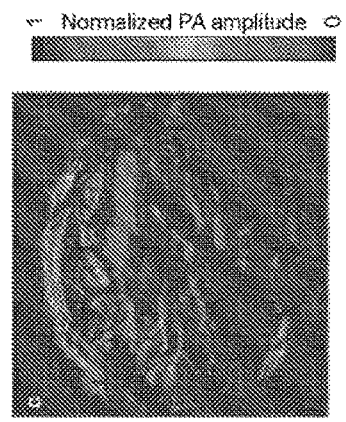
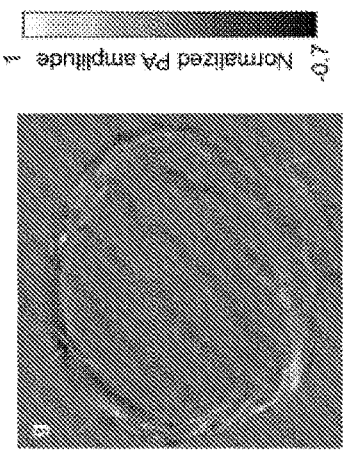
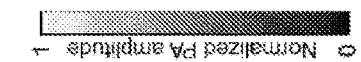
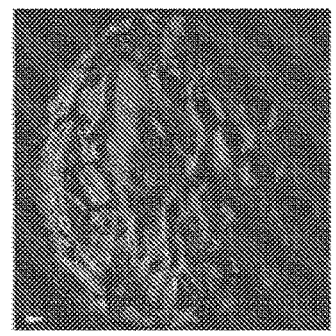
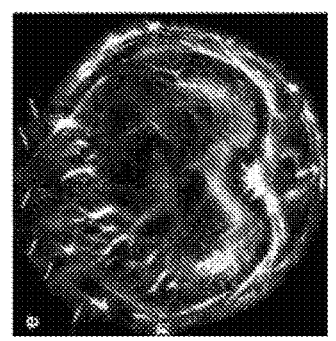
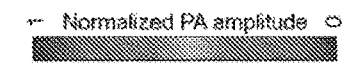
FIG. 40A  FIG. 40B  FIG. 40C
FIG. 40D  FIG. 40E  FIG. 40F
FIG. 40G

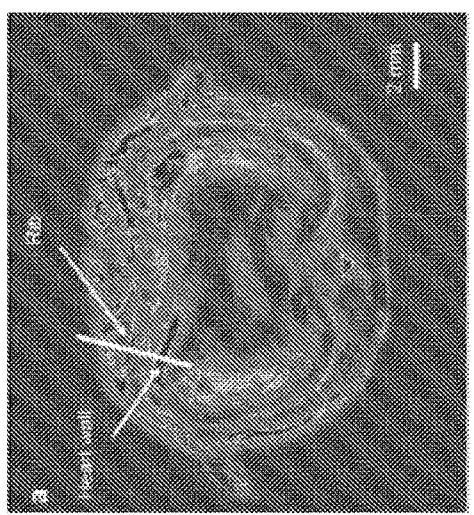
FIG. 42A
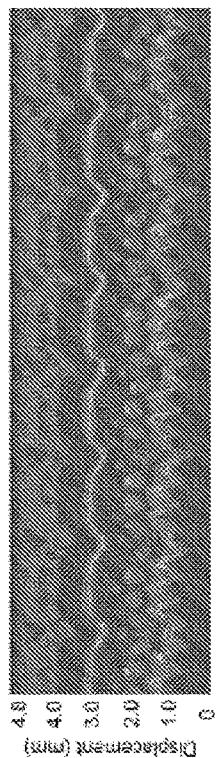
FIG. 42B
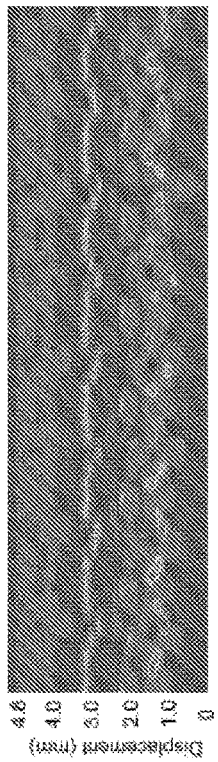
FIG. 42C
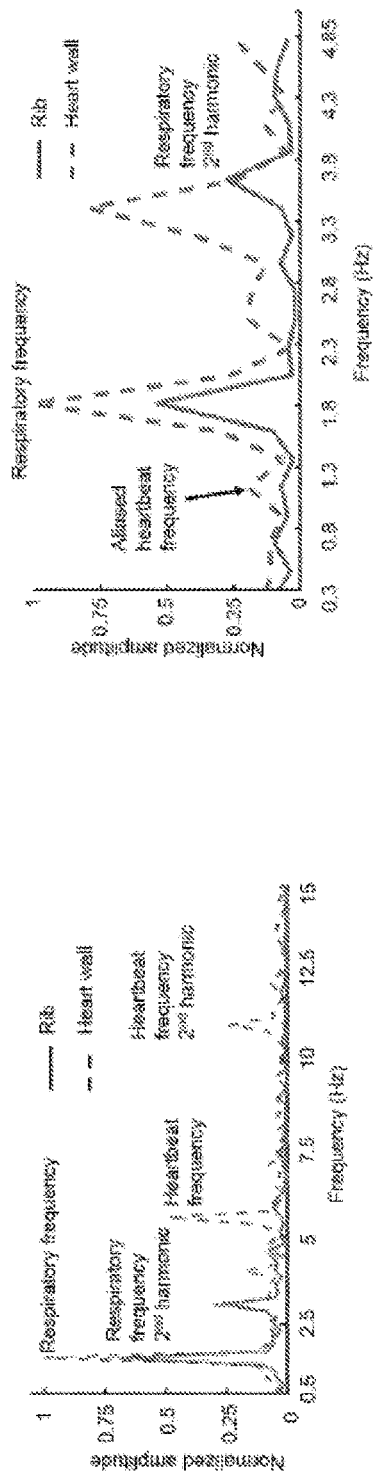
FIG. 42D
FIG. 42E

SINGLE-IMPULSE PANORAMIC PHOTOACOUSTIC COMPUTED TOMOGRAPHY (SIP-PACT)

CROSS-REFERENCE TO RELATED APPLICATION

This application is a U.S. National Phase Application of PCT/US2017/063764, filed Nov. 29, 2017, which claims the benefit of priority to U.S. Provisional Patent Application Ser. No. 62/427,470, filed Nov. 29, 2016, the contents of which are hereby expressly incorporated by reference in their entirety.

STATEMENT REGARDING FEDERALLY SPONSORED RESEARCH & DEVELOPMENT

This invention was made with government support under grant EBO16963 awarded by National Institutes of Health. The government has certain rights in the invention.

BACKGROUND OF THE INVENTION

The field of this disclosure relates generally to a photoacoustic tomography imaging system used to capture whole-body images of small animals with high frame rate and high resolution.

Small animals, in particular rodents, are essential models for preclinical studies, and they play an important role in modeling human physiology and development, in guiding the study of human diseases and in advancing the quest for effective treatments. The ability to directly visualize dynamics with high spatiotemporal resolution in these small-animal models at the whole-body scale provides insights into biological processes at the whole organism level. In addition to high spatiotemporal resolution, the ideal non-invasive small-animal imaging technique would provide deep penetration and functional contrasts. Previously, small-animal whole-body imaging has typically relied on non-optical approaches, including magnetic resonance imaging (MRI), X-ray computed tomography (X-ray CT), positron emission tomography (PET) or single-photon emission computed tomography (SPECT), and ultrasound tomography (UST). Although these techniques provide deep penetration, they suffer from significant limitations. For example, adapting MRI to achieve microscopic resolution requires costly high-strength magnetic fields and long data acquisition time, ranging from seconds to minutes; this data acquisition time is too slow for imaging dynamics. X-ray CT can achieve microscopic resolution, but lacks functional contrast. X-ray CT and PET/SPECT involve the use of ionizing radiation, which may inhibit longitudinal monitoring. UST does not provide cannot image blood oxygenation or extravascular molecular contrasts. To overcome these limitations, new imaging modalities are needed.

Optical imaging of biological tissue employs non-carcinogenic electromagnetic waves to provide extraordinary structural, functional, and molecular contrasts with either endogenous or exogenous agents. However, the application of conventional optical imaging technologies to small-animal whole-body imaging is impeded by the strong optical scattering of tissue, which prevents high-resolution imaging beyond the optical diffusion limit of about one mm in depth. Although existing diffusive optical imaging methods such as fluorescence diffuse optical tomography can provide penetration to a depth on the order of centimeters, the image resolution resulting from existing diffusive optical imaging methods is rather poor (approximately ⅓ of the penetration depth).

Photoacoustic tomography (PAT) is a high-resolution optical imaging modality that overcomes the optical diffusion limit. In PAT, the energy of incident photons is absorbed by the tissue to be imaged and re-emitted as ultrasonic waves. The ultrasonic waves are subsequently detected to generate tomographic images with optical contrasts. Due to the weak scattering of ultrasound in soft tissue (about three orders of magnitude weaker than light scattering on a per unit path length basis in the ultrasonic frequency of interest), PAT enjoys superb resolution even deep within tissues with a depth-to-resolution ratio of about 200. PAT has been implemented primarily in the forms of scanning-based photoacoustic microscopy (PAM) and reconstruction-based photoacoustic computed tomography (PACT). Previous studies have demonstrated high-speed, high-resolution functional PAM of the mouse brain in vivo with penetration up to several millimeters. PACT has enabled imaging to depths beyond 10 mm, but hardware and sensor design limitations may necessitate a tradeoff of image resolution versus temporal resolution/frame rate. PACT systems typically either make use of data acquisition multiplexing to enhance image resolution but with poor temporal resolution due to multiplexing delays, or make use of an ultrasound transducer array that enables a higher frame rate, but with unclearly resolved sub-organ features due to partial acoustic detection coverage. For high-performance small-animal whole-body imaging, a need exists for an imaging system capable of simultaneously achieving deep penetration, high spatial resolution, high fidelity, multiple contrasts, high imaging speed, and even high detection sensitivity in one system.

The ability to directly visualize dynamics of internal structures with high spatiotemporal resolution in various small-animal models at the whole-body scale may provide insights into biological processes at the whole organism level. In addition to high spatiotemporal resolution, an ideal non-invasive small-animal imaging technique should provide deep penetration and functional contrasts.

BRIEF DESCRIPTION OF THE INVENTION

In one aspect, a PACT system for producing a 2D or 3D image of at least a portion of a subject is disclosed. The PACT system includes a light source configured to direct a light pulse into an imaging plane passing through the at least a portion of the subject. A plurality of photoacoustic signals is produced within the imaging plane in response to illumination by the light pulse. The PACT system also includes a full-ring transducer array that includes a plurality of ultrasound transducers. The plurality of ultrasound transducers are distributed around a circumference of a ring surrounding the imaging plane. The full-ring transducer array is configured to spatially sample the plurality of photoacoustic signals. The full-ring transducer array is configured to spatially sample a portion of the plurality of photoacoustic signals originating from within a field of view positioned within the imaging plane. The field of view includes a diameter selected to satisfy a Nyquist spatial sampling criterion.

In another aspect, a method of reconstructing an image from a plurality of PA signals detected by a detector array comprising a plurality of detectors is disclosed. The method includes providing a speed-of-sound (SOS) map representing a spatial distribution of a first SOS $V_1$ and a second SOS $V_2$ within an imaging region of a PA imaging device. The SOS map includes an elliptical tissue region positioned within a circular water region.

For each combination of a plurality of PA signal source positions and a plurality of detector positions within the SOS map, the method in this aspect also includes: calculating a total distance L of a signal path from each PA signal source position to each detector position; calculating a first distance $L_1$ from each PA signal source position to an intersection point of the signal path with a tissue-water interface; and calculating a second distance $L_2$ from the intersection point to each detector position by subtracting $L_1$ from L. The tissue-water interface includes an elliptical boundary enclosing the tissue region on the SOS map.

In addition, for each combination of the plurality of PA signal source positions and the plurality of detector positions within the SOS map, the method in this aspect further includes calculating a delay time $t_{delay}$ according to Eqn. (12):

$$t_{delay} = \frac{L_1}{V_1} + \frac{L_2}{V_2} \qquad \text{Eqn. (12)}$$

In this aspect, the delay time $t_{delay}$ is a sum of a first time to travel at the first SOS $V_1$ through the tissue region and a second time to travel at the second SOS $V_2$ through the water region.

The method in this aspect further includes combining all calculated $t_{delay}$ values to form a dual-SOS delay map that includes each $t_{delay}$ value and each corresponding PA signal source position and detector position. The method additionally includes reconstructing the image using a universal back-projection method with the dual-SOS delay map.

In an additional aspect, a PACT system for producing a 2D or 3D image of a breast of a subject is disclosed. The PACT system includes a light source configured to direct a light pulse into an imaging plane passing through the breast of the subject. A plurality of photoacoustic signals is produced within the imaging plane in response to illumination by the light pulse. The PACT system also includes a full-ring transducer array that includes a plurality of ultrasound transducers. The plurality of ultrasound transducers are distributed around a circumference of a ring surrounding the imaging plane. The full-ring transducer array is configured to spatially sample the plurality of photoacoustic signals. The full-ring transducer array is configured to spatially sample a portion of the plurality of photoacoustic signals originating from within a field of view positioned within the imaging plane. The field of view includes a diameter selected to satisfy a Nyquist spatial sampling criterion.

BRIEF DESCRIPTION OF THE DRAWINGS

The following drawings illustrate various aspects of the disclosure.

FIG. 1A is a schematic representation of dual-wavelength illumination in a SIP-PACT system for mouse brain functional imaging in one aspect;

FIG. 1B is a schematic representation of single-wavelength illumination from the SIP-PACT system suitable for mouse trunk imaging in one aspect;

FIG. 1C is a close-up view of the focusing optics (dashed box region) of the SIP-PACT system illustrated in FIG. 1B, showing a conical design of light delivery and PA wave detection using top illumination;

FIG. 4A is an image of a cortical vasculature of a mouse overlaid with a map of $sO_2$ levels measured during hyperoxia using a SIP-PACT system in one aspect;

FIG. 4B is an image of a cortical vasculature of a mouse overlaid with a map of $sO_2$ levels measured during hypoxia using a SIP-PACT system in one aspect;

FIG. 4C is a graph showing changes in brain $sO_2$ levels during an oxygen challenge (highlighted in grey) obtained using analysis of images similar to the $sO_2$ maps shown in FIG. 4A and FIG. 4B;

FIG. 4D is a graph showing changes in brain concentrations of oxy-hemoglobin and deoxy-hemoglobin during an oxygen challenge (highlighted in grey) obtained by analysis of images similar to the $sO_2$ maps of FIG. 4A and FIG. 4B;

FIG. 4E is a cross-sectional image of a lower abdominal cavity overlaid with a map of fractional changes in the amplitudes of PA signals corresponding to blood oxygen levels obtained using a SIP-PACT system in one aspect;

FIG. 4F is a bar graph summarizing the normalized PA amplitude levels representing blood oxygen levels ($sO_2$) of several internal organs during hyperoxia (white bars) and hypoxia (black bars);

FIG. 9A is a schematic diagram illustrating a numerical simulation of a dual speed universal back-projection reconstruction method;

FIG. 9B is a map of a simulated optical absorption distribution of a numerical phantom simulation;

FIG. 9C is a SIP-PACT image reconstructed using an existing single speed reconstruction method, including a close-up inset highlighting splitting artifacts associated with the unmatched speed of sound in the simulated numerical phantom;

FIG. 9D is a SIP-PACT image reconstructed using a dual speed reconstruction method in one aspect, including a close-up inset illustrating the reduction in splitting artifacts due to inclusion of a second speed of sound within the reconstruction method;

FIG. 10A is a schematic diagram defining various parameters used in a dual speed back-projection in an aspect;

FIG. 10B is a schematic showing a map of back-projected positions of a point source using a single-speed reconstruction method in which the color of each back-projected position denotes an in-plane azimuthal angle of the transducer array illustrated in FIG. 10A, and in which the correct position of the point source is denoted by a star;

FIG. 10C is an in vivo SIP-PACT image of a cross-section of a mouse trunk (liver) reconstructed using filtered back-projection based on a single-speed reconstruction method (v=1.520 mm/µs);

FIG. 10D is an in vivo SIP-PACT image of the cross-section of the mouse trunk shown in FIG. 10C, reconstructed using filtered back-projection based on a dual-speed reconstruction method ($v_1$=1.590 mm/µs and $v_2$=1.507 mm/µs);

FIG. 13A is a label-free SIP-PACT image of a mouse brain cortex after injection of CTCs;

FIG. 13B is a time trace plot similar to the time trace plot of FIG. 12B of each pixel along an artery transect denoted by a dashed line in FIG. 13A;

FIG. 13C is a map of a 2D Fourier transform of the data of FIG. 13B similar to the map of FIG. 12C;

FIG. 15A contains a series of SIP-PACT images of a mouse cortex obtained at different times after the injection of a PA contrast agent Each image cis overlaid with a color map representing a magnitude of differential PA signal measured at each time relative to a corresponding PA signal obtained prior to the injection of the PA contrast agent;

FIG. 15B is a graph of the total PA signal of the mouse brain as a function of time for a period after the injection of a PA contrast agent;

In FIG. 16, regions corresponding to abdominal organs are delineated by dashed lines and labels: IN, intestine; LK, left kidney; RK, right kidney; and SP, spleen;

FIG. 24A is an image showing a correlation map of a rat brain with left and right seeds marked by crosses superimposed on the brain image.

FIG. 24B is an image showing a correlation map of a rat brain with left and right seeds marked by crosses superimposed on the brain image.

FIG. 24C is a graph of the spontaneous variations in the PA signal in the contralateral regions marked by the crosses in FIG. 24A.

FIG. 24D is a graph of the spontaneous variations in the PA signal in the contralateral regions marked by the crosses in FIG. 24B.

FIG. 24E is a graph of the frequency distribution of the PA signals in the correlated regions in FIG. 24A.

FIG. 24F is a graph of the frequency distribution of the PA signals in the correlated regions in FIG. 24B.

FIG. 24G is a graph of the temporal correlation function between the PA signals obtained at the seed region (right cross spot) and the nearby region (blue curve, corresponding to the high-intensity spot on the right brain in (a)) or between the same seed region and the contralateral region (red curve, corresponding to the high-intensity spot on the left brain in FIG. 24A).

FIG. 24H is a graph of the temporal correlation function between the PA signals obtained at the seed region (right cross spot) and the nearby region (blue curve, corresponding to the high-intensity spot on the right brain in FIG. 24B) or between the same seed region and the contralateral region (red curve, corresponding to the high-intensity spot on the left brain in FIG. 24B).

FIG. 26A is an enhanced unipolar image showing a mouse cortical vasculature, SSS, superior sagittal sinus.

FIG. 26B is a reconstructed image using half-time dual-speed-of-sound universal back projection showing a mouse cortical vasculature, SSS, superior sagittal sinus.

FIG. 26C is an enhanced unipolar image showing two lobes of the liver, AA, abdominal aorta; IVC, inferior vena cava; LLV, left lobe of liver; PV, portal vein; RLV, right lobe of liver.

FIG. 26D is a reconstructed image using half-time dual-speed-of-sound universal back projection showing two lobes of the liver, AA, abdominal aorta; IVC, inferior vena cava; LLV, left lobe of liver; PV, portal vein; RLV, right lobe of liver.

FIG. 26E is an enhanced unipolar image showing the lower abdominal cavity, BM, backbone muscles; CM, cecum; IN, intestines; LK, left kidney; RK, right kidney SC, spinal cord; SP, spleen.

FIG. 26F is a reconstructed image using half-time dual-speed-of-sound universal back projection the lower abdominal cavity, BM, backbone muscles; CM, cecum; IN, intestines; LK, left kidney; RK, right kidney SC, spinal cord; SP, spleen.

FIG. 40A is a SIP-PACT image reconstructed using full-time dual-speed-of-sound universal back-projection and a detection view angle of 360°.

FIG. 40B is a SIP-PACT image reconstructed using full-time dual-speed-of-sound universal back-projection and a detection view angle of 270°.

FIG. 40C is a differential image between FIG. 40A and FIG. 40B.

FIG. 40D is a SIP-PACT image reconstructed using half-time dual-speed-of-sound universal back-projection and a detection view angle of 360°.

FIG. 40E is a SIP-PACT image reconstructed using half-time dual-speed-of-sound universal back-projection and a detection view angle of 270°.

FIG. 40F is a differential image between FIG. 40D and FIG. 40E.

FIG. 40G is a differential image between FIG. 40A and FIG. 40D.

FIG. 42A is an image showing a cross-sectional image of an upper thoracic cavity.

FIG. 42B is a spatiotemporal map of the PA signals extracts from two transects denoted as superimposed lines in the image of FIG. 42A, in which the imaging was performed at a frame rate of 50 Hz.

FIG. 42C is a spatiotemporal map of the PA signals extracts from two transects denoted as superimposed lines in the image of FIG. 42A, in which the imaging was performed at a frame rate of 10 Hz.

FIG. 42D is a graph showing Fourier transforms of the 50 Hz spatiotemporal map of FIG. 42B, showing the respiratory frequency and heartbeat frequency, respectively.

FIG. 42E is a graph showing Fourier transforms of the 10 Hz spatiotemporal map of FIG. 42C, showing the respiratory frequency, but with the heartbeat frequency aliased due to the low frame rate.

DETAILED DESCRIPTION OF THE INVENTION

Figure 2A:
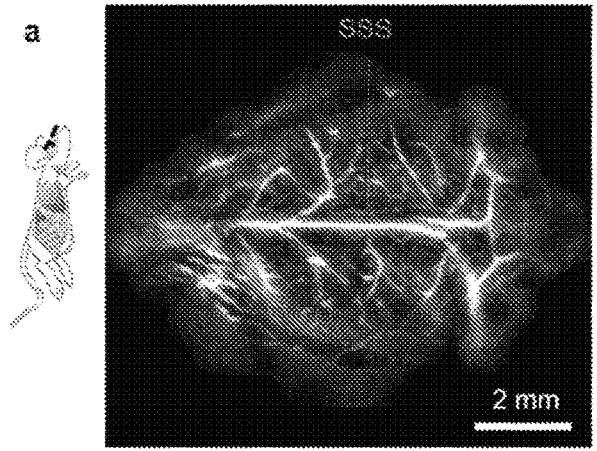
FIG. 2A is a label-free SIP-PACT image of the vasculature of a mouse brain cortex.
Figure 2B:
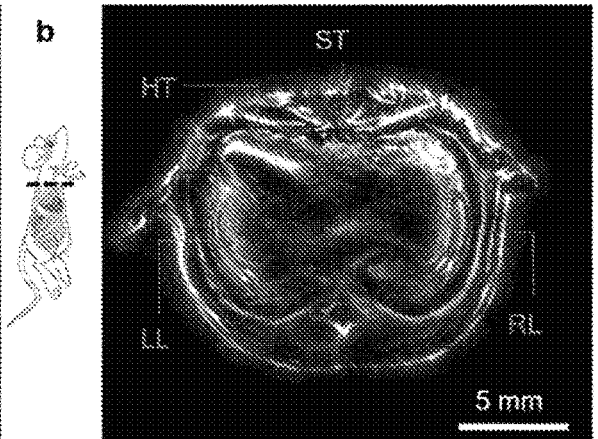
FIG. 2B is a cross-sectional label-free SIP-PACT image of a mouse upper thoracic cavity.
Figure 2C:
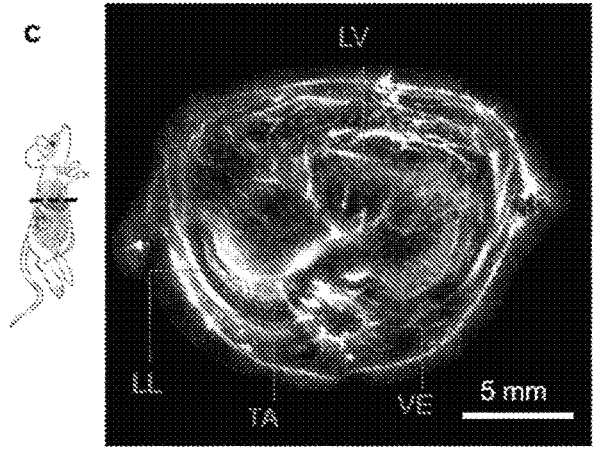
FIG. 2C is a cross-sectional label-free SIP-PACT image of a mouse lower thoracic cavity.
Figure 2D:
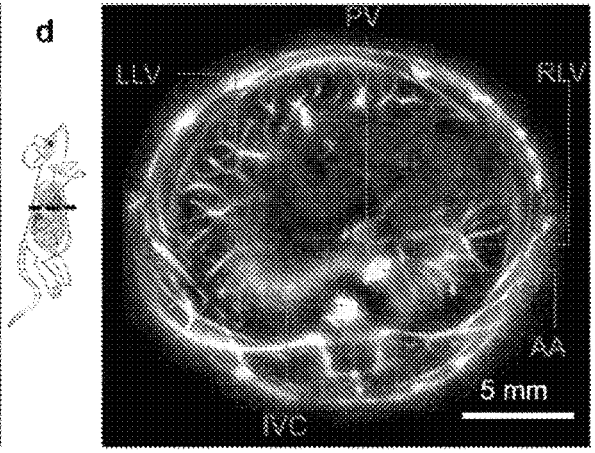
FIG. 2D is a cross-sectional label-free SIP-PACT image of two lobes of a mouse liver.
Figure 2E:
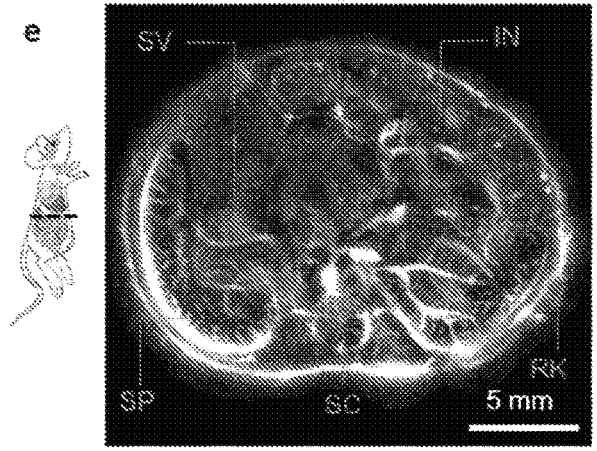
FIG. 2E is a cross-sectional label-free SIP-PACT image of a mouse upper abdominal cavity.

In various aspects, a single-impulse panoramic photoacoustic computed tomography (SIP-PACT) system for small-animal whole-body imaging is disclosed. The SIP-PACT system enables the acquisition of PA images characterized by high spatiotemporal resolution, strong anatomical and functional contrasts, deep penetration into the imaged animal, and full-view fidelity. In one aspect, the SIP-PACT system may penetrate through about three cm of tissue in vivo to acquire cross-sectional images with 100-μm resolution at a 50-Hz frame rate, using only a single laser impulse to acquire all PA signals needed to reconstruct an entire image corresponding to one imaging plane. Using the disclosed SIP-PACT system to acquire repeated images within the same imaging plane, whole-body dynamics may be imaged in real time with clear sub-organ anatomical and functional detail, and circulating melanoma cells may be tracked in vivo without need for labeling. The images made possible by the disclosed SIP-PACT system may enable advances in research related to pharmacology, pathology, oncology, and others.

In various aspects, the disclosed SIP-PACT system enables the capture of structural, functional, and/or cellular small-animal whole-body images with high spatiotemporal resolution and image quality. The imaging capability enabled by the architecture of the SIP-PACT system overcomes several limitations of existing whole-body imaging systems by simultaneously achieving high spatial resolution as well as rapid data acquisition speed. In one aspect, the high spatial resolution acoustic detection of the SIP-PACT system may be enabled by the inclusion of a full-ring ultrasound transducer array with a field of view configured to detect PA signals throughout the imaging plane, thereby minimizing partial-view artifacts. In addition, the fast temporal resolution of the SIP-PACT system is simultaneously enabled through the inclusion of one-to-one mapped preamplification and analog-to-digital sampling of each transducer in the full-ring ultrasound transducer array. The resulting high spatiotemporal resolution enables the acquisition of PA images using a single laser impulse to obtain a sufficient number and spatial distribution of PA signals from within the imaging plane to reconstruct a complete 2D image in various aspects.

In addition to the inclusion of ultrasound sensing elements with enhanced spatial sensitivity and data acquisition speed, the SIP-PACT system further makes use of a novel dual-speed-of-sound universal back-projection (dual-SOS UBP) algorithm to compensate for the first-order effect of acoustic inhomogeneities within the body of the imaged animal, thereby further enhancing the fidelity and quality of the PA images obtained using the SIP-PACT system. The dual-SOS UBP algorithm overcomes the limitation of existing image reconstruction methods by compensating for the first-order effect of acoustic inhomogeneities without increasing the complexity of signal demodulation and image reconstruction. Existing methods either make use of time-consuming iterative speed-of-sound corrections, or require additional hardware and software to acquire a map of the speed-of-sound (SOS) within the body of the animal to be imaged in order to account for acoustic inhomogeneities. The dual-SOS UBP algorithm is an extension of an existing universal back-projection (UBP) algorithm that accounts for acoustic inhomogeneities without significantly impacting the main advantage of the UPB algorithm (rapid image reconstruction time) and without need for additional hardware or software.

In various aspects, the SIP-PACT system enables at least several new whole-body imaging capabilities, with performance complementary to the non-optical approaches described herein previously. By way of non-limiting example, the SIP-PACT system may non-invasively image whole-body internal anatomies of mice, with sub-organ vasculature and internal organ structures clearly resolved at a 50 Hz frame rate without need for contrast agents or other extrinsic labeling. At such high spatiotemporal resolutions, the biological dynamics associated with heartbeats and respiration may be clearly observed without motion artifacts. The SIP-PACT system may also take advantage of the absorption spectral signatures of oxy-hemoglobin and deoxy-hemoglobin to provide for mouse brain and whole-body functional imaging at a comparably high frame rate. Furthermore, by incorporating ultrasonically encoded PA flowography methods, the SIP-PACT system may measure whole-body blood flow speeds without need for exogenous labeling. In combination with the functional imaging capabilities described herein, the SIP-PACT system in one aspect may enable the non-invasive imaging of whole-body metabolic rate of oxygen consumption at a relatively high frame rate, which may provide quantitative information about the oxygen consumption of tumors or other physiological structures. The SIP-PACT system in another aspect may be used to image the process of perfusion of a near infrared (NIR) dye in the brain and/or internal organs of a mouse to enable molecular imaging of these structures. In another additional aspect, the SIP-PACT system may be used to visualize and track circulating tumor cells (CTCs) in a live mouse brain without need for labeling.

As a result of the fully parallelized data acquisition of all ultrasonic transducer channels described herein above, the SIP-PACT system enables wide-field photoacoustic imaging in a single laser shot without need for scanning or multiplexing to form an image. In various aspects, the SIP-PACT system may enable the capture of snapshot images of the object at a microsecond time scale (including the time associated with laser excitation and acoustic propagation), which is sufficiently fast to observe most biological processes above the cellular scale with no motion artifacts.

In one additional aspect, the SIP-PACT system may be configured as described herein below to obtain 2D images at a frame rate of at least 1 kHz up to a hardware-limited frame rate of up to about 20 kHz. At this high imaging speed, the SIP-PACT system may be used for whole-brain neural imaging of single action potential pulses. Existing neural imaging methods make use of an existing high-resolution optical method, such as two-photon microscopy, or other existing non-optical methods with deep penetration, such as functional MRI. These existing high-resolution optical methods provide shallow and highly localized information with limited insights into the global picture of neuronal function, and existing non-optical methods with deep penetration typically have relatively limited spatiotemporal resolutions. As a result, studying how neurons and complex neural circuits interact in both time and space may be currently hindered by the lack of contrast agents and image formation technology capable of imaging deep into the brain to visualize fast neuron activities, such as the propagation of action potentials and sub-threshold events that take place on sub-millisecond to millisecond timescales. In this one additional aspect, the SIP-PACT system may enable the detection of local neural activities with high spatiotemporal resolution in a more global context to enhance the understanding of how such local neural activities interchange, communicate, and accumulate to generate behavioral consequences. Used in conjunction with voltage-sensitive PA proteins or dyes, the SIP-PACT system may enable the challenging task of whole-brain, high spatiotemporal resolution neural imaging.

I. SIP-PACT System

FIG. 1A and FIG. 1B are schematic drawings illustrating the arrangements of various elements of a SIP-PACT system in two aspects. In both aspects illustrated in FIG. 1A and FIG. 1B, the SIP-PACT system includes at least one laser source configured to produce a plurality of laser pulses to be directed into at least a portion of a whole body of an animal to be imaged via one or more optical elements. The plurality of laser pulses illuminates a plurality of biological structures within the whole body of the animal, thereby inducing the production of a plurality of PA signals.

Referring again to FIG. 1A and FIG. 1B, the plurality of PA signals may be detected by an ultrasound transducer array (denoted as USTA in FIG. 1A and FIG. 1B) incorporated into the SIP-PACT system. The SIP-PACT systems illustrated in FIG. 1A and FIG. 1B further include a plurality of pre-amps configured to amplify the plurality of PA signals detected by the ultrasound transducer array with minimal introduction of noise as described in additional detail herein below. In an aspect, each ultrasound transducer of the ultrasound transducer array may be coupled directly to each corresponding pre-amp configured to exclusively amplify the PA signals received by a single ultrasound transducer in the ultrasound transducer array. Without being limited to any particular theory, the direct coupling of the plurality of pre-amps to the plurality of ultrasound transducers in the ultrasound transducer array is thought to reduce the data acquisition times by obviating the need to multiplex the measured PA signals from the plurality of ultrasound transducers into shared pre-amps. Further, it is thought that the highly parallelized amplification of the detected PA signals as described herein above may reduce the introduction of noise into the plurality of PA signals prior to amplification due to the reduction of potential noise-generating electrical leads, connections and/or junctures enabled by the direct coupling of each pre-amp to each corresponding ultrasound transducer in the ultrasound transducer array.

In various aspects, the frame rate of the SIP-PACT system in various aspects may be influenced by any one or more of a variety of factors including, but not limited to: laser pulse rate and hardware processing rates associated with data acquisition and other processes associated with SIP-PACT imaging, such as signal amplification, analog to digital conversion, and data buffering/storage. As described herein above, the arrangement of the ultrasound transducers in a full-ring array, as well as the parallelized arrangement of transducers, pre-amplifiers, and/or analog to digital converters reduces the impact of many of these factors, thereby enabling high spatiotemporal resolution capable of measuring biological dynamics in small animals.

In various aspects, the SIP-PACT system may be configured to obtain brain images and/or whole body images at various axial locations along a whole body of an animal. FIG. 1A illustrates schematically a SIP-PACT system configured to obtain brain images that includes optical elements arranged to direct laser pulses in the form of a single diffuse beam to the brain of the small animal from above, shown illustrated in detail in FIG. 1C. FIG. 1B illustrates schematically a SIP-PACT system configured to obtain whole body images at various axial locations that includes optical elements arranged to direct laser pulses in the form of a toroidal beam, shown illustrated in detail in FIG. 1D. The toroidal beam delivers light radially inward within a preselected imaging plane corresponding to a single axial location to be imaged. In an aspect, the SIP-PACT system may further include at least one scanning element such as a magnetic base scanner (MBS; see FIG. 1B) configured to translate and/or rotate the small animal in order to reposition the whole body of the animal such that the toroidal beam illuminates another predetermined axial position to be imaged.

Referring again to FIG. 1B, the SIP-PACT system may further incorporate additional equipment including, but not limited to, a data acquisition system (DAQ) and a computer. The additional equipment may be configured to coordinate the operation of various devices of the SIP-PACT system, such as the laser source(s), ultrasound transducer array, and/or scanning elements used to acquire a plurality of PA signals suitable for producing SIP-PACT images. The additional equipment may be further configured to receive amplified PA signals from the ultrasound transducer array, condition the amplified PA signals to enhance signal-to-noise ratio, and/or reconstruct SIP-PACT images using a reconstruction algorithm.

In various additional aspects, the SIP-PACT system may be modified to perform 2D or 3D breast imaging. In one aspect, a single breath-hold PACT system (SBH-PACT) enables non-invasive breast imaging that includes the benefits of SIP-PACT imaging as described herein, including, but not limited to, deep penetration, high spatiotemporal resolution, and 2D/3D switchable modes. The enhanced spatiotemporal resolution and expanded imaging capabilities enabled by SIP-PACT imaging further extends the capabilities of existing non-invasive breast imaging methods deep penetration to provide additional diagnostic abilities including, but not limited to, sensitive breast cancer detection. In one aspect, the SBH-PACT system has a relatively high framing rate of at least 10 Hz, enabling 3D imaging to be accomplished within the period of a single breath hold of a patient. Compared to existing breast imaging methods, such as mammography, SBH-PACT utilizes non-ionizing radiation, demonstrates sensitivity in radiographically dense breasts, and imposes less or no pain during imaging by only slightly compressing the breast against the chest wall. Further, SBH-PACT may distinguish malignant tumors from benign tumors by quantifying blood vessel densities in the tumor.

FIG. 45 is a schematic illustration of a SBH-PACT system in one aspect. The SBH-PACT system includes an illumination laser, an ultrasonic transducer array, signal amplification/acquisition modules, a linear scanning stage, and a patient bed. In this aspect, the illumination laser produces a 1064-nm laser beam (PRO-350-10, Quanta-Ray, 10-Hz pulse repetition rate, 8-12-ns pulse width) that passes through a lab-polished axicon lens (25 mm diameter, 160° apex angle), followed by expansion by an engineered diffuser (EDC-10-A-2s, RPC Photonics) to form a donut-shaped light beam. The laser fluence (20 mJ/cm$^2$) is selected to fall within the American National Standards Institutes (ANSI) safety limit for laser exposure (100 mJ/cm$^2$ at 1064 nm at a 10-Hz pulse repetition rate).

Figure 44:
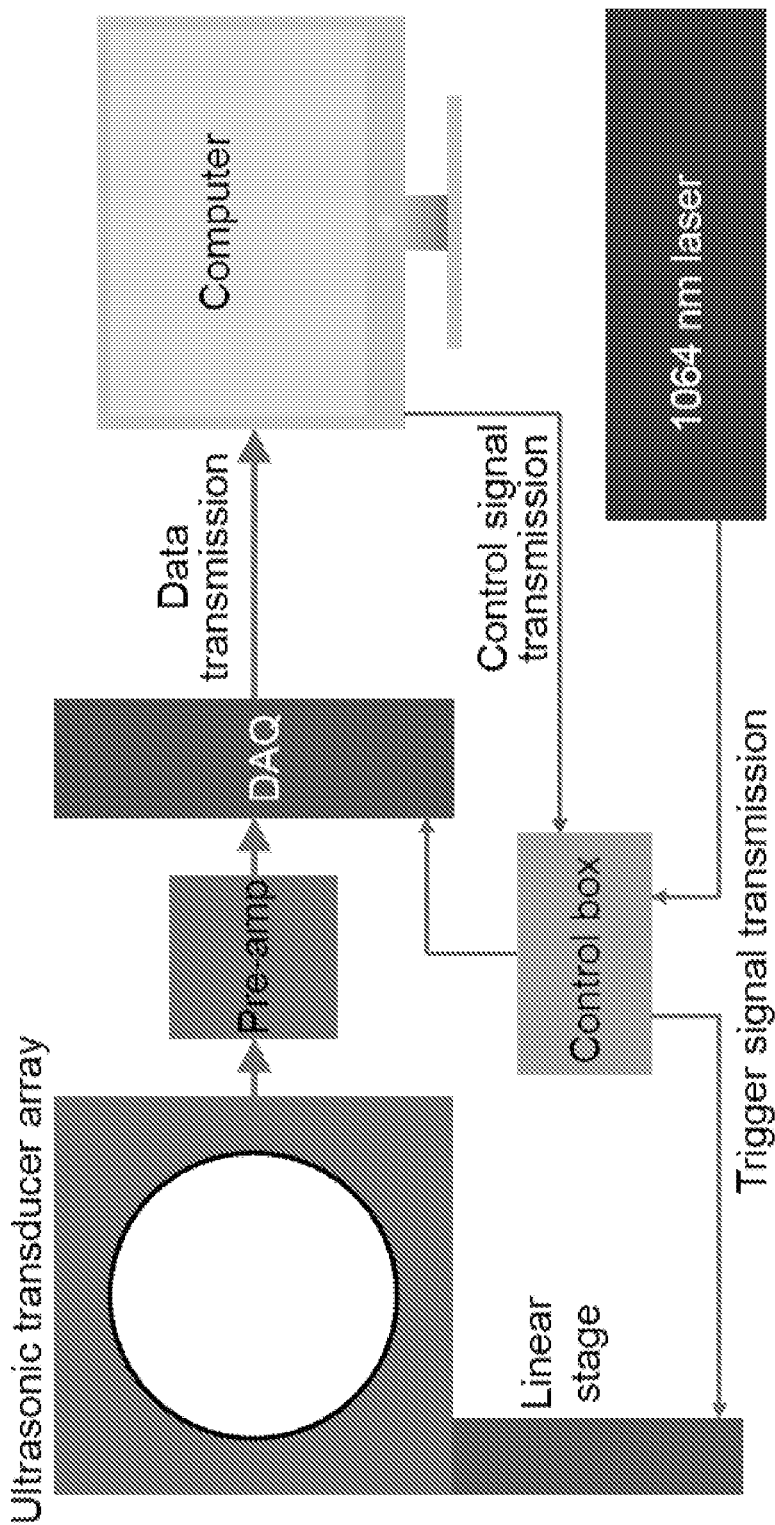
FIG. 44 is a schematic illustration of the electrical elements of a SBH-PACT breast imaging system.

To achieve 2D panoramic acoustic detection, the SBH-PACT system includes a 512-element full-ring ultrasonic transducer array (Imasonic, Inc.; 220 mm ring diameter; 2.25 MHz central frequency; more than 95% one-way bandwidth). Each element has a flat-rectangular aperture (5 mm element elevation size; 1.35 mm pitch; 0.7 mm inter-element spacing). The ultrasonic transducer array housing is mounted on a stainless steel rod (25 mm diameter) and enclosed in an acrylic water tank. A linear stage (THK America, Inc., KR4610D) is fixed beneath the water tank and is configured to move the transducer array elevationally via the stainless steel rod. Four sets of lab-made 128-channel preamplifiers (26 dB gain) are positioned around the water tank, and are connected to the ultrasonic array housing via signal cable bundles. Each set of preamplifiers is further connected to a 128-channel data acquisition system (SonixDAQ, Ultrasonix Medical ULC; 40 MHz sampling rate; 12 bit dynamic range) with programmable amplification up to 51 dB. The digitized radio frequency data are first stored in an onboard buffer, and then transferred to a computer through a universal serial bus 2.0 (see FIG. 44). The data acquisition systems are configured to record PA signals within 100 μs after each laser pulse excitation. To synchronize the SBH-PACT system, the laser's external trigger is used to trigger both the data acquisition systems and the linear scanner.

In use, the patient is positioned prone with one breast dependent and placed into a large aperture in the imaging bed. An agar pillow affixed on top of an acrylic tube lightly presses the breast against the chest wall. Compared to craniocaudal or mediolateral breast compression, compression against the chest wall not only avoids pain, but also gives the least thickness breast tissue for light to penetrate from the nipple to the chest wall. The laser illuminates the breast from beneath the patient's breast, and the ultrasonic transducer array detects photoacoustic waves circumferentially around the breast. The light beam is converted into a donut shape via the axicon lens followed by an engineered diffuser. Compared to a Gaussian beam, the donut beam provides more uniform illumination inside the breast and also deposits less energy on the nipple and areola, which have a higher concentration of pigment. The selected illumination wavelength of 1064 nm is characterized by low optical attenuation within the breast tissues, thereby enabling sufficient optical penetration in breast tissue for PACT imaging.

Detailed descriptions of the elements of the SIP-PACT and SBH-PACT systems in various aspects are provided herein below.

a) Transducer Array

In various aspects, the SIP-PACT system includes an ultrasound transducer array to detect a plurality of PA signals within the whole body of an animal. The ultrasound transducer array includes a plurality of ultrasound transducers arranged to form an array enclosing at least a portion of the whole body of the animal to be imaged. In various aspects, the arrangement of the plurality of ultrasound transducers may be configured to enable complete detection coverage over the entire spatial extent of each whole-body image obtained using the SIP-PACT system. In one aspect, the complete detection coverage may be the entire extent of an axial slice through the whole body or brain of an animal. In another aspect, the complete detection coverage may be a 3D volume containing at least a portion of the whole body of the animal.

In an aspect, the complete detection coverage enabled by the incorporation of the ultrasound transducer array obviates the need to rely upon the use of scanning the ultrasound transducers and the use of multiple laser pulses to acquire each PA image. As a result, the ability of the SIP-PACT system in various aspects to detect PA signals sufficient to reconstruct an entire 2D or 3D image in response to a single laser pulse enables a significantly higher frame rate relative to existing PACT systems or other imaging modalities.

In various aspects, the ultrasound transducer array may be arranged in any 2D or 3D configuration without limitation. In various aspects, the arrangement of the plurality of ultrasound transducers in the array typically enclose at least a portion of the whole body of the animal to be imaged to enable complete detection coverage for each image obtained by the SIP-PACT system. Non-limiting examples of suitable arrangements for the transducers in the ultrasound transducer array include: a linear arrays full-ring, a half-ring, an ellipse, a cylinder, a hemisphere, a full sphere, and any other suitable arrangement of transducers. In various aspects, ultrasound transducer arrays that are arranged in a 2D configuration may be scanned in order to obtain PA signals sufficient to reconstruct an entire 2D or 3D image. By way of non-limiting example, a linear array may be scanned in a rotational pattern to obtain PA signals sufficient to reconstruct an entire 3D image.

In one aspect, the ultrasound transducer array may be a full-ring ultrasound transducer array, in which at least a portion of the animal to be imaged is positioned within the interior of the ring. In this aspect, the full-ring ultrasonic transducer array may include a plurality of ultrasound transducers distributed around the perimeter of the full ring. The number of transducers included in the full-ring ultrasound transducer array may be selected based on any one or more of at least several factors including, but not limited to: desired detection resolution, available space along the circumference of the ring, dimensions of the ring, and any other relevant factor. In various aspects, the full-ring ultrasound transducer array may include at least about 10 transducers up to about 1600 transducers or more.

In various aspects, the number of transducers in the ultrasound transducer array may be selected based on any one or more of at least several factors. Higher numbers of transducers may enhance the resolution of the PA images obtained using the SIP-PACT system, but higher numbers of transducers may also necessitate additional pre-amp channels in the pre-amp device and additional data channels in the analog-to-digital sampling device to enable parallelized amplification and data sampling, as described herein below. The size of the body of the animal to be imaged using the SIP-PACT system may also influence the number of transducers included in the ultrasound transducer array; larger array dimensions may need to be provided for imaging larger animals, and more transducers may be included in the ultrasound transducer array to provide a desired resolution of PA images obtained by the SIP-PACT system. Higher numbers of transducers in the ultrasound transducer array may further influence frame rates, because the additional PA signal data obtained by additional transducers may take additional time to process during signal conditioning and PA image reconstruction.

By way of non-limiting example, a full-ring transducer array with 512 elements may enable sampling an object within a field of view of about 16 mm diameter, as determined by the equation below:

$$\frac{N\lambda}{2} \geq \pi D$$

where N=512 is the number of elements, $\lambda$=200 µm is the wavelength corresponding to the high-cut-off frequency of the transducer, and D is the diameter of the FOV. Within a FOV of 16 mm, the reconstructed images resulting from PA signals obtained by the 512-element full-ring transducer array have uniform resolution. Without being limited to any particular theory, a higher number of transducers may increase the FOV with uniform resolution.

In various aspects, the type of ultrasound transducers included in the ultrasound transducer array may be any suitable type of transducer without limitation. In one aspect, all transducers included in the ultrasound transducer array may be focused ultrasound transducers including, but not limited to, cylindrically focused ultrasound transducers. In one aspect, all focused transducers may be focused to a common center point coinciding with the geometric center of the ring. In other aspects, at least a portion of the ultrasound transducers may be focused at different positions from one another. In yet other aspects, the ultrasound transducers in the ultrasound transducer array may include any combination of focused and unfocused ultrasound transducers.

By way of non-limiting example, a full-ring transducer array including, all focused transducer elements, such as cylindrically focused transducer elements, may be incorporated into a SIP-PACT imaging system for 2D imaging. Without being limited to any particular theory, the incorporation of the focused transducers enhances the elevational resolution of the reconstructed PA images and the sensitivity of the transducer array within a 2D focal plane. By way of another non-limiting example, a transducer array that includes all unfocused transducer elements may be incorporated into a SIP-PACT imaging system for 3D imaging.

In various other aspects, the operational parameters characterizing the performance of each transducer in the transducer array may be selected to be compatible with PA CT imaging using a single laser pulse wavelength, two laser pulse wavelengths, or three or more laser pulse wavelengths to illuminate the region to be imaged. In addition, the sampling rate of each transducer in the transducer array may be selected to enable SIP-PACT imaging at a suitably high frame rate of up to about 20 kHz.

In various aspects, the frame rate of the SIP-PACT system may range from about 10 Hz to about 20 kHz, as determined by the laser repetition rate. In various other aspects, the software controlling the operation of the various devices and/or elements of the SIP-PACT system may be modified to operate the SIP-PACT system at a frame rate below a frame rate determined by the laser repetition rate. In these various other aspects, the SIP-PACT system may operate at a frame rate of about 5 Hz, about 2 Hz, about 1 Hz, or lower.

In one exemplary aspect, the SIP-PACT system may include a 512-element full-ring ultrasonic transducer array (Imasonic, Inc., 5 MHz, 90% one-way bandwidth). In this exemplary aspect, each transducer may have a cylindrical focus of 0.02 NA, a 20 mm element elevation size, 0.061 mm pitch, and 0.01 mm inter-element spacing. In this arrangement, the full-ring ultrasonic transducer array enables 2D panoramic in-plane acoustic detection, thereby avoiding partial-view artifacts related to the directive emission of PA waves. In one aspect, the 512-element full-ring ultrasonic transducer array as described herein above provides an ~30 mm diameter field of view (FOV), ~100 µm isotropic in-plane resolution, and full-view fidelity (i.e., no partial-view artifacts).

In various aspects, the ultrasound transducer array may further include one-to-one mapped pre-amplification, in which each ultrasound transducer in the transducer array may be coupled directly to one dedicated pre-amp channel configured to pre-amplify only those PA signals detected by one ultrasound transducer of the ultrasound transducer array, resulting in parallelized pre-amplification of the PA signals detected by the plurality of transducers in the ultrasound transducer array. In these various aspects, the plurality of pre-amp channels may be operatively coupled to the corresponding plurality of ultrasound transducers with minimal lengths of electrical connecting cables. In one aspect, the plurality of pre-amp channels may be directly coupled to the corresponding plurality of ultrasound transducers to eliminate the electrical connecting cables altogether. Without being limited to any particular theory, it is thought that the direct connection of each pre-amp channel to its corresponding ultrasound transducer minimizes noise within the detected PA signals received by each pre-amp channel from each corresponding ultrasound transducer, resulting in reduced noise within the pre-amplified PA signals produced by each pre-amp channel.

Any one or more suitable pre-amp devices may be incorporated into the SIP-PACT system without limitation. In one aspect, a single pre-amp device that includes a plurality of pre-amp channels may be incorporated into the SIP-PACT system, so long as the number of pre-amp channels provided in the single pre-amp device matches or exceeds the total number of ultrasound transducers in the ultrasound transducer array. In another aspect, two or more pre-amp devices may be incorporated into the SIP-PACT system, so long as the combined total number of pre-amp channels from the two or more pre-amp devices matches or exceeds the total number of ultrasound transducers in the ultrasound transducer array. In one aspect, the SIP-PACT system may include a single 512-channel pre-amplifier with a 26 dB gain directly connected to a housing of a full-ring ultrasonic transducer array, with minimized connection cable length to reduce cable noise.

In various aspects, the pre-amp gain of the plurality of pre-amp channels of the at least one pre-amp device may be any suitable value without limitation. The pre-amp gain selected for use in the SIP-PACT system may be influenced by one or more of at least several factors including, but not limited to: acceptable signal-to-noise ratio, operating parameters of other data acquisition and data processing elements of the SIP-PACT system such as the analog-to-digital sampling devices, signal amplifiers, buffers, and computing devices. Without being limited to any particular theory, the pre-amp gains may be selected to fall within a range that is suitably high for enabling transmission of the PA signals with minimal signal contamination, but below a gain that may saturate the dynamic ranges of the data acquisition (DAQ) system used to digitize the amplified PA signals as described herein below. In various aspects, the pre-amp gain of the plurality of pre-amp channels of the at least one pre-amp device may be at least about 5 dB, at least about 7 dB, at least about 9 dB, at least about 11 dB, at least about 13 dB, at least about 15 dB, at least about 17 dB, at least about 19 dB, at least about 21 dB, at least about 23 dB, at least about 25 dB, and at least about 30 dB.

In various other aspects, the SIP-PACT system may further include one-to-one mapped analog-to-digital sampling, in which each pre-amp is operatively coupled to a corresponding dedicated data channel of an analog-to-digital sampling device to enable parallelized analog-to-digital sampling of the plurality of pre-amplified PA signals. The pre-amplified PA signals produced by each individual pre-amp channel are received by a single dedicated data channel of the at least one analog-to-digital sampling devices. Any one or more suitable analog-to-digital sampling devices may be incorporated into the SIP-PACT system without limitation. In one aspect, a single analog-to-digital sampling device that includes a plurality of channels may be incorporated into the SIP-PACT system, so long as the number of data channels provided in the single analog-to-digital sampling device matches or exceeds the total number of pre-amp channels of the at least one pre-amp devices. In another aspect, two or more analog-to-digital sampling devices may be incorporated into the SIP-PACT system, so long as the combined total number of data channels in the two or more analog-to-digital sampling devices meets or exceeds the total number of pre-amp channels of the at least one pre-amp devices.

In one exemplary aspect, the pre-amplified PA signals were digitized by a 512-channel data acquisition (DAQ) system that included four analog-to-digital sampling devices (SonixDAQ, Ultrasonix Medical ULC, 128 channels each, 40 MHz sampling rate, 12-bit dynamic range) with programmable amplification up to 51 dB. In one aspect, the digitized PA signals may be stored in an onboard buffer and subsequently transferred to a computing device via a USB 2.0 connection. In another aspect, the digitized PA signals may be transferred to a computing device directly after digitization by the at least one analog-to-digital sampling device.

In various aspects, SIP-PACT imaging is enabled using two-dimensional (2D) acoustic detection geometry, and the SIP-PACT system is configured to form each 2D cross-sectional image of a whole body of an animal using illumination from a single laser pulse. The in-plane resolution of the 2D cross-sectional image is determined by the acoustic time-of-flight resolution, and the elevational resolution is determined by the acoustic focus and the center acoustic frequency. Without being limited to any particular theory, both resolutions may be enhanced by the incorporation of higher frequency ultrasonic transducers in the transducer array. In one aspect, the data acquisition (DAQ) system may provide 512 channels in parallel to enable fully parallelized processing of each ultrasound transducer in the transducer array at an 80 MHz sampling rate. In this aspect, the 80 MHz sampling rate may be compatible with an ultrasonic transducer array that includes transducers with a 15 MHz center frequency and/or a laser source capable of producing laser pulses at a pulse repetition rate on the order of kHz, thereby enabling finer spatial resolution and higher imaging speed. In various aspects, the enhanced spatiotemporal resolution of SIP-PACT imaging enabled by the incorporation of higher frequency ultrasound transducers and high pulse repetition rate laser sources may be compatible with relatively demanding imaging tasks, including, but not limited to neuroimaging.

In various aspects, an acoustic coupling element matched to the transmissivity of the animal to be imaged may be positioned between the external surface of the animal and the ultrasound transducer array. Any known devices, compositions, and methods for providing an acoustically transmissive material between a portion of the animal to be imaged and the transducers of the acoustic transducer array may be incorporated as an acoustic coupling element into the SIP-PACT system without limitation. Non-limiting examples of suitable acoustic coupling agents include a layer of acoustic coupling gel, a tank containing an acoustic coupling medium such as water, and any combination thereof. In one non-limiting example, at least a portion of the animal to be imaged may be immersed in a water tank. In various aspects, additional devices including, but not limited to compressive elements, vacuum pumps, and any other suitable device may be incorporated into the SIP-PACT system to remove and/or to inhibit the formation of any air bubbles within the acoustic coupling medium that may produce confounding PA signals not associated with the structures within the focal region of the ultrasound transducer array.

b) Pulsed Laser and Associated Optical Elements

Referring again to FIG. 1A and FIG. 1B, the SIP-PACT system further includes at least one pulsed laser configured to produce a plurality of laser pulses to be directed into the whole body of the animal using at least one optical element. In an aspect, each laser pulse produced by the at least one pulsed laser is configured to induce a plurality of PA signals within the portion of the whole body to which the laser pulse is directed. As described herein above, the plurality of PA signals induced by a single laser pulse are detected by the transducer array and reconstructed into a PA image as described herein previously.

In various aspects, each of the at least one pulse lasers may produce a plurality of laser pulses at a pulse wavelength. The pulse wavelength may be selected based on any one or more of at least several factors including, but not limited to: enhanced penetration of the particular tissue to be imaged by the pulse wavelength, enhanced contrast of structures of interest with respect to surrounding structures, as may be useful in non-labeled visualization of circulating tumor cells, and enhanced contrast of exogenous structures of interest as may be useful in SIP-PACT imaging of the perfusion of contrast agents such as NIR dyes. In one aspect, a pulse wavelength ranging from about 650 nm to about 1350 nm may be selected to maximize optical penetration through a whole body of a mammal to be imaged, as this wavelength range is to encompass pulse wavelengths that are less attenuated within mammalian tissues relative to wavelengths falling outside of this "optical window". In one particular aspect, a pulse wavelength of about 1064 nm may be selected to enable PA imaging in mammalian tissues using the SIP-PACT system.

In an aspect, the at least one pulsed laser may produce laser pulses at a single wavelength, at two (dual) wavelengths, or at three or more (multiple) wavelengths as needed. In various aspects, the plurality of laser pulses may be produced at one or more wavelengths within a range of from approximately 650 nm to approximately 1350 nm, thereby enabling maximal optical penetration for whole-body imaging of animal subjects. Without being limited to any particular theory, this wavelength range is characterized by enhanced penetration through biological tissues; for example, this wavelength range is previously known to correspond to pulse wavelengths where mammalian tissues least attenuate light.

In an aspect, the SIP-PACT system may make use of a single pulse wavelength selected for enhanced penetration of a particular tissue to be imaged, and/or enhanced contrast of structures of interest with respect to surrounding structures. In another aspect, the SIP-PACT system may make use of dual and/or multiple pulse wavelengths to enable functional imaging including, but not limited to determining oxygen saturation within blood and other tissues. For example, a first pulse wavelength may be selected to enable maximum contrast for oxy-hemoglobin, and a second pulse wavelength may be selected to enable maximum contrast for deoxy-hemoglobin or, alternatively, enable maximum contrast for all hemoglobin. Dual/multiple pulse wavelengths may also be selected for enhanced contrast of different structures, such as blood cells, CTCs, white blood cells, contrast agents such as NIR dyes, or enhanced contrast of exogenous structures of interest (i.e. perfusion of contrast agents such as NIR dyes). In various aspects, the SIP-PACT system may include a pulsed laser producing laser pulses at a single pulse wavelength including, but not limited to: a 720 nm laser such as a LS-2145-LT-150 Ti-sapphire (Ti-Sa) pulsed laser (Symphotic Tii) with 20 Hz repetition rate and 12 ns pulse width; a 1064 nm laser such as a DLS9050 pulsed laser (Continuum) with a 50 Hz repetition rate and a pulse width ranging from about 5 ns to about 9 ns; and any other suitable pulsed laser.

Figures 11A, 11B, 11C, 11D:
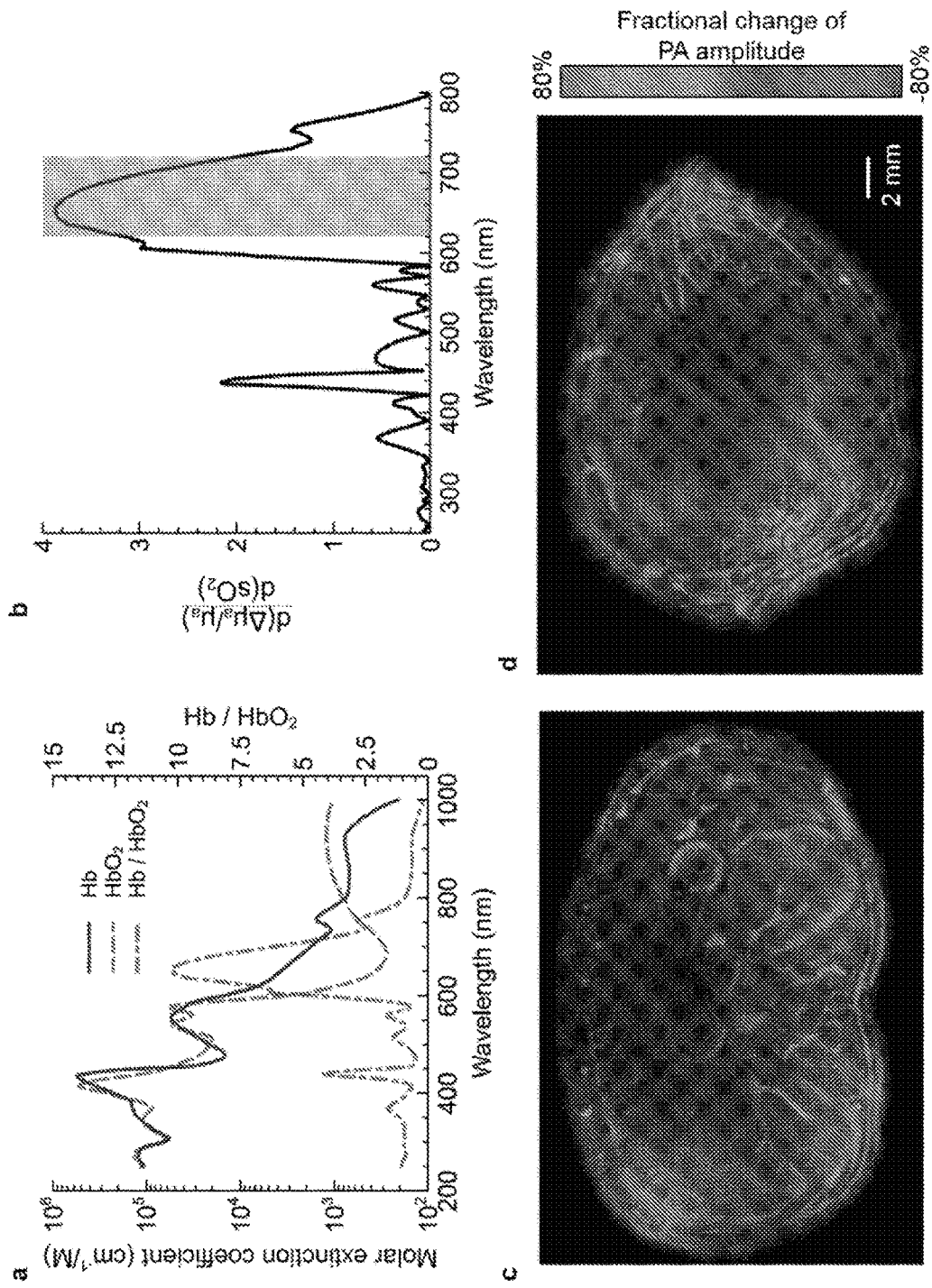
FIG. 11A is a graph of an absorption spectra of oxy-hemoglobin ($HbO_2$, long dashes), an absorption spectra of deoxy-hemoglobin (Hb, solid line), and a spectrum of the absorption ratio of deoxy-hemoglobin to oxy-hemoglobin ($Hb/HbO_2$, dot-dash line)
FIG. 11B is a graph showing a spectrum of the fractional changes in blood absorption coefficient ($\mu_a$) corresponding to the blood sO2 change ($d(\Delta\mu_a/\mu_a) d(sO_2)$) over the wavelengths of the visible and NIR light spectra.
FIG. 11C is an image showing a map of fractional changes of PA signal amplitude corresponding to fractional changes of blood oxygen levels in a cross-section of a lower abdominal cavity during oxygen challenge obtained from analysis of a label-free SIP-PACT image.
FIG. 11D is an image showing a map of fractional changes of PA signal amplitude corresponding to fractional changes of blood oxygen levels in a cross-section of two lobes of a liver during oxygen challenge obtained from analysis of a label-free SIP-PACT image.

By way of non-limiting example, the molar optical absorption of deoxy-hemoglobin is much higher than that of oxy-hemoglobin within the wavelength range of about 600 nm-800 nm, as illustrated in FIG. 11A. As a result, PA signals elicited in response to laser pulses within this 600 nm-800 nm wavelength range may be more sensitive to changes in deoxy-hemoglobin concentration, as illustrated in FIG. 11B. In one aspect, an intermediate pulse wavelength including, but not limited to, 720 nm may be selected for whole-body functional imaging, to balance the factors of suitable penetration depth and deoxy-hemoglobin sensitivity.

Figures 12A, 12B, 12C:
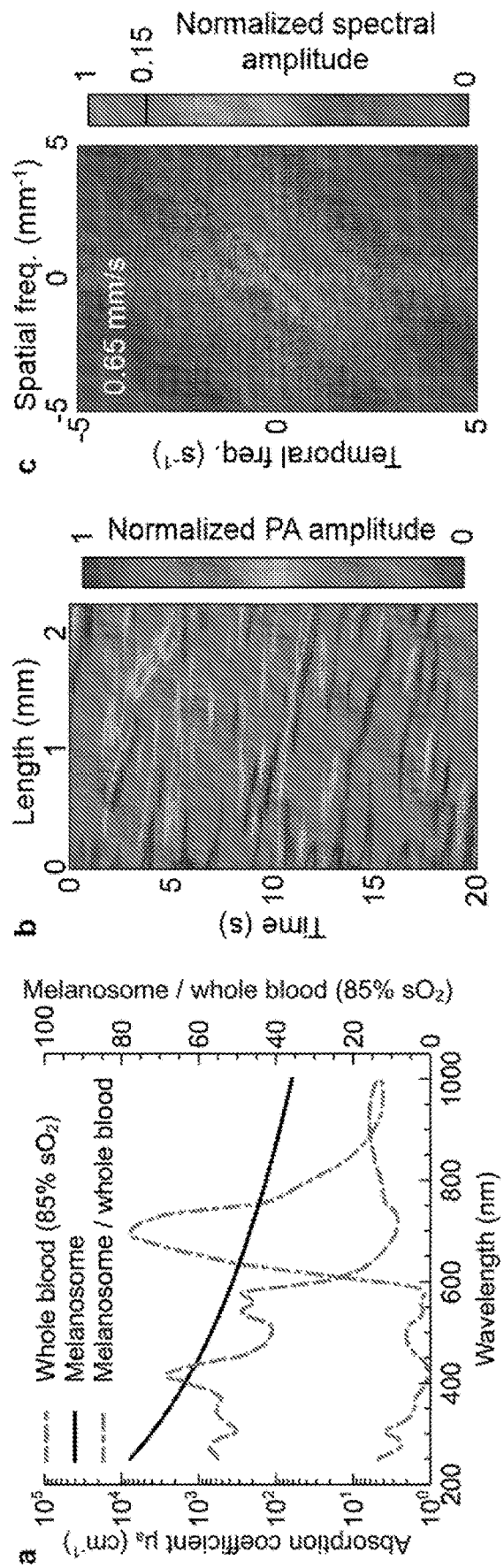
FIG. 12A is a graph showing the absorbance spectra of whole blood (85% $sO_2$) and melanosomes, as well as a spectrum of the absorption ratio of melanosomes and whole blood.
FIG. 12B is a time trace plot of each pixel along a transect denoted by a dashed line in FIG. 5A. Within the time trace plot, the horizontal axis corresponds to distance along the transect and the vertical axis corresponds to time after injection of CTCs.
FIG. 12C is a map of a 2D Fourier transform of the data of FIG. 12B. Lines with matched slopes in the space-time domain (i.e. similar velocities) are mapped onto a single line in the spatiotemporal frequency domain corresponding to the map of FIG. 12C.

By way of another non-limiting example, the optical absorption of melanosomes decreases slowly with an increase in wavelength, and the optical absorption of hemoglobin is relatively weak within the far red and NIR regions, as illustrated in FIG. 12A. As further illustrated in FIG. 12A, the optical absorption ratio between melanosomes and whole blood at about 85% $sO_2$ peaks at about 680 nm. In an aspect, a pulse laser configured to produce a plurality of laser pulses at an excitation pulse wavelength of about 680 nm including, but not limited to a Q-Smart 850 pulsed laser (Quantel) with a 10 Hz repetition rate and a 6 ns pulse width with a basiScan-M/280 (Newport) optical parametric oscillator (OPO) may be used for imaging circulating melanoma cancer cells using the SIP-PACT system as described herein.

In various aspects, each pulsed laser of the SIP-PACT system is configured to deliver a plurality of laser pulses at a pulse repetition rate ranging from about 1 Hz and about 20 kHz. The pulse repetition rate for each pulsed laser may be selected based any one or more of at least several factors including, but not limited to: enablement of a desired frame rate (i.e. temporal resolution) to reduce motion artifacts; capture of processes such as infusion of a contrast agent; capture of physiological processes such as propagation of action potentials, calcium responses, and/or heart beats; ensure relaxation of tissues between laser pulses to minimize artifacts induced by residual temperature or pressure fluctuations associated with previous laser pulses; and any other relevant factor.

By way of non-limiting example, during single-wavelength SIP-PACT imaging, a single-wavelength pulsed laser, such as a 1064 nm pulsed laser, may deliver laser pulses at a pulse repetition rate of about 50 Hz. In various other aspects, during dual-wavelength or multi-wavelength SIP-PACT imaging, the pulsed lasers may be operated in a coordinated manner such that each laser pulse produced by each corresponding pulsed laser is separated from an adjacent laser pulse produced by another corresponding pulsed laser, resulting in a repeating series of laser pulses, in which each series contains one of each laser pulse produced at each of the pulse wavelengths by each corresponding pulsed laser of the at least one pulsed lasers and each laser pulse is separated from each adjacent laser pulse by a suitably long delay time. In an aspect, the suitably long delay may be configured to enable relaxation of the illuminated tissue between laser pulses to prevent artifacts in the PA signals related to tissue heating by a prior laser pulse in the repeating series of laser pulses.

In various aspects, for a SIP-PACT system conducting dual-wavelength or multi-wavelength PA imaging, the delay time between each laser pulse in a repeating series used in dual-wavelength or multi-wavelength imaging may range from about 10 µs to about 100 µs. In one aspect, the delay time between each adjacent laser pulses used during dual-wavelength or multi-wavelength PA imaging may be about 50 µs. Without being limited to any particular theory, a delay of about 50 µs is sufficiently short to ensure that the animal to be imaged remains relatively stationary in terms of most biological activities, resulting in essentially simultaneous illumination.

By way of non-limiting example, a repeating series of laser pulses is illustrated schematically on the inset graphs of FIG. 1A and FIG. 1B. As illustrated in FIG. 1A, two pulse wavelengths are produced in an alternating sequence with a delay of 50 µs between the first 1064 nm pulse and the second 630 nm (see FIG. 1A) or 720 nm (see FIG. 1B) pulse. Both the first and the second laser pulses have pulse widths of 10 ns and pulse repetition rates of 10 Hz (1/100 ms).

In an aspect, the SIP-PACT system may further include a control card configured to synchronize the operation of the at least one pulsed laser to produce the repeating series laser pulses used for dual-wavelength or multi-wavelength imaging. Non-limiting examples of suitable control cards include a sbRIO-9626 control card (National Instruments). By way of non-limiting example, the control card may be operatively coupled to Q-switch triggers of each pulsed laser with a fixed delay of 50 µs, to enable a first pulsed laser to fire about 50 µs later than a second pulsed laser.

In various other aspects, each pulsed laser of the SIP-PACT system is configured to deliver a plurality of laser pulses at a pulse width ranging from about 1 ps to about 20 ns. The pulse width of each laser pulse may be selected based any one or more of at least several factors including, but not limited to: laser pulse fluence in compliance with applicable safety standards including, but not limited to, ANSI safety standards; laser pulse fluence sufficient to elicit the production of detectable PA signals throughout the spatial extent of the portion of the animal to be imaged; pulse width sufficiently long to inhibit tissue damage due to non-thermal effects; pulse width sufficiently small to discern moving structures within the whole body of the animal to be imaged, such as circulating blood cells; and any other relevant factor.

In various aspects, the laser pulse width may be selected to enable a desired bandwidth of the PA signals produced by various sources within a region of a whole body of an animal. Without being limited to any particular theory, the bandwidth of the PA signals produced by the various sources may be selected to be broader than the transmissible bandwidth of the PA signals. The transmissible bandwidth of the PA signals, in turn, may be selected to enable a penetration range sufficient to transmit the PA signals from the sources within the whole body of the animal to the ultrasound transducer array positioned outside the animal. In animal tissues, higher frequency signals attenuate faster, resulting in lower penetration ranges. In addition, operational parameters of other devices and/or elements of the SIP-PACT system including, but not limited to, the ultrasonic transducer bandwidth, may influence the selection of a PA signal frequency and associated transmissible bandwidth. Accordingly, the laser pulse width may be selected to accommodate a transmissible bandwidth that is selected according to any one or more of the factors described above.

In various aspects, the SIP-PACT system may further include one or more optical elements configured to direct the plurality of laser pulses produced by the at least one pulsed laser into a region of a whole body of an animal to be imaged using the SIP-PACT system. The focal region of the ultrasound transducer array coincides with at least a portion of the region of the whole body of an animal to be imaged that is illuminated by the laser pulses, so that PA signals induced by the plurality of laser pulses are detected by the ultrasound transducer array and used to reconstruct one or more PA images.

In various aspects, the one or more optical elements are operatively coupled to the at least one pulsed laser in order to receive the plurality of laser pulses produced by the at least one pulsed laser. Further, the one or more optical elements are configured to perform various transformations of the plurality of laser pulses including, but not limited to: alter the direction of travel of each laser pulse; redistribute the distribution of light energy across a cross-sectional area of each laser pulse into an essentially uniform spatial distribution of light energy; alter the cross-sectional size and/or shape of each laser pulse; modulate the light intensity or fluence of each laser pulse; modulate the relative time of arrival of two different laser pulses produced by two corresponding pulsed lasers, selectively transmit or block transmission of laser pulses from one or more pulsed lasers, and any other suitable transformation of the plurality of laser pulses.

Non-limiting examples of suitable optical elements suitable for incorporation into the SIP-PACT system include one or more of: prisms, mirrors, diffusers, condensers, lenses, beam splitters, beam combiners, optic fibers, wave-guides, and any other known optical element suitable for modifying one or more characteristics of the laser pulse. Non-limiting examples of characteristics of a laser pulse that may be modified and/or modulated using one or more optical elements include: cross-sectional profile, cross-sectional dimensions, direction of travel, wave speed, wave length, polarization, intensity, phase, wavefront shape, superposition with other laser pulses, cross-sectional energy homogeneity, pulse width, delay with respect to other laser pulses in a pulse series, and any other relevant characteristics of a laser pulse.

In an aspect, a diffuser may be configured to homogenize a laser pulse profile so that the energy intensity is distributed uniformly across a cross-sectional area of a laser pulse. Non-limiting examples of suitable diffusers include various engineered diffusers such as ring diffusers. In one aspect, the diffuser may be a commercially available engineered diffuser including, but not limited to, an EDC-10-A-1r (RPC Photonics). Non-limiting examples of suitable condensers include various customized condensers, such as a customized ring condenser. Non-limiting examples of suitable prisms include triangular prisms, rhomboidal prisms, and any other suitable prism. Non-limiting examples of suitable lenses include convex lenses, concave lenses, cylindrical lenses, half-cylinder lenses, compound lenses, and any other suitable lens. In another aspect, the lens may be a commercially available lens including, but not limited to, an AX-FS-1-140-0 conical lens (Del Mar Photonics). Non-limiting examples of suitable mirrors include planar mirrors, convex mirrors, and concave mirrors.

In various aspects, the one or more optical elements may be further configured to enable an illumination approach selected according to the region of the whole body of the animal to be imaged and/or the type of imaging to be conducted using the SIP-PACT system. In one aspect, the one or more optical elements may be configured to enable a top illumination approach, as illustrated in FIG. 1A and FIG. 1C. In another aspect, the one or more optical elements may be configured to enable a side illumination approach, as illustrated in FIG. 1B and FIG. 1D. The selection of specific optical elements incorporated into the SIP-PACT system may be influenced at least in part by the illumination approach to be used by the SIP-PACT system.

Referring to FIG. 1A and FIG. 1C, a top illumination approach directs a plurality of laser pulses into a region of the whole body of the animal from above and detects PA signals elicited in response to illumination by each laser pulse using side detection. For brain imaging illumination, the excitation beam was uniformly shined on the cortex after passing through an engineered diffuser.

As illustrated in FIG. 1A, the one or more optical elements may include a mirror, a beam combiner, a prism, and a diffuser. Laser pulses produced by the least one pulsed laser may be directed to the mirror and/or to the beam combiner. Each laser pulse entering the beam combiner exits along a single direction toward the prism. The prism redirects each entering laser pulse from the beam combiner toward the top of the animal to be imaged by way of the diffuser. Each laser pulse emerging from the diffuser is homogenized and expanded to enable a laser pulse with a relatively uniform cross-sectional energy distribution and a cross-sectional area matched to the cross-sectional area of the portion of the animal to be imaged. As illustrated in FIG. 1A and FIG. 1C, the cross-sectional area of each laser pulse illuminating the animal to be imaged from above may be sized to illuminate at least the entire cross-sectional area of the animal positioned within the focal plane of the ultrasound transducer array. Although tissue structures in the animal illuminated by each laser pulse using the top illumination approach may produce additional PA signals, including the tissue structures above and below the focal plane of the transducer array, only those PA signals originating from tissue structures within the focus region of the ultrasound transducer array are detected and reconstructed into a PA image. In an aspect, the top illumination approach may be suitable for use in brain cortex imaging using the SIP-PACT system.

Referring to FIG. 1B and FIG. 1D, a side illumination approach directs a plurality of laser pulses toward a surface region of the whole body of the animal from the side in the form of a ring-shaped laser pulse illuminating the outer surface of the whole body of the animal to be imaged. In various aspects, the light energy delivered by each ring laser pulse propagate and scatter inward toward the interior of the animal's body, enabling illumination of at least a region of the whole body positioned within the focal plane of the ultrasound transducer array. In an aspect, the transverse plane containing the illuminated surface region of the animal to be imaged coincides with the focal plane of the ultrasound transducer array (see FIG. 1D). As described previously herein, illumination of structures by the propagated/scattered light at sufficient pulse fluence may elicit PA signals from these structures, and at least a portion of the PA signals may be produced by structures positioned outside of the focal plane of the ultrasound transducer array. Although tissue structures above and below the focal plane of the ultrasound transducer array within the animal illuminated by each ring-shaped laser pulse using the side illumination approach may produce additional PA signals, only those PA signals originating from tissue structures within the focal plane of the ultrasound transducer array are detected and reconstructed into a PA image as described herein.

In various aspects, the side illumination approach may enable various types of SIP-PACT imaging including, but not limited to, imaging of a trunk of the animal. As illustrated in FIG. 1B, the one or more optical elements included in the SIP-PACT system in this aspect may include a mirror, a beam combiner (BC), a prism, and a diffuser, a conical lens (CL), and a ring-shaped optical condenser (OC). As illustrated in FIG. 1B, laser pulses produced by the least one pulsed laser may be directed to the mirror and/or to the beam combiner. Each laser pulse entering the beam combiner exits along a single direction toward the prism. The prism redirects each entering laser pulse from the beam combiner toward the diffuser positioned between the prism and the animal to be imaged. Each homogenized and expanded laser pulse emerging from the diffuser is directed toward a conical lens positioned between the diffuser and the animal to be imaged. The conical lens focuses the incoming beam with a circular cross-sectional profile into beam with a ring-shaped cross-sectional profile directed toward the ring-shaped optical condenser. The ring-shaped optical condenser redirects the ring-shaped laser pulse toward the focal plane of the ultrasound transducer array and further reduces the radius of the ring-shaped laser pulse to enable the illumination of the exposed surface of the animal coinciding with the focal plane of the ultrasound transducer array. As illustrated in FIG. 1B and FIG. 1D, the cross-sectional diameter of each ring-shaped laser pulse may be sized to illuminate at least the entire circumference of the exposed region of the animal to be imaged coinciding with the focal plane of the ultrasound transducer array. In an aspect, the one or more optical elements may direct each ring-shaped laser pulse in a direction configured to illuminate a region of the animal's volume that is coincident with the focus of the ultrasound transducer array to enable confocal PA imaging.

In one aspect, the one or more optical elements of the SIP-PACT system may be configured to enable a top illumination approach or a side illumination approach, but not both approaches. In another aspect, the one or more optical elements of the SIP-PACT system may be configured as modular elements that may be removed, rearranged, replaced, or otherwise altered to enable the top illumination approach, the side illumination approach, or any combination thereof. By way of non-limiting example, a diffuser, a conical lens (CL), and a ring-shaped optical condenser (OC) may be reversibly positioned within the top illumination SIP-PACT system of FIG. 1A to transform this system into a side illumination SIP-PACT system similar to the system illustrated in FIG. 1B.

c) Scanning Elements

In one aspect, the SIP-PACT system may image a single 2D plane through the whole body of an animal repeatedly to obtain a time series of PA images to track changes of structures within the 2D plane such as perfusion of a contrast dye or changes in oxygen concentrations. In this aspect, a means of precisely positioning the body of the animal relative to the imaging elements of the SIP-PACT system and/or a means of maintaining the position of the animal's body while obtaining a time-series of PA images may enhance the quality of the 2D time series obtained. In another aspect, the SIP-PACT system may obtain PA images corresponding to a series of 2D planes through the whole body of an animal to visualize structures throughout the whole body of the animal. In this other aspect, the series of PA images obtained at different 2D planes may be combined to reconstruct a 3D PA image of the whole body of the animal. In this other aspect, a means of repositioning the animal relative to the imaging elements of the SIP-PACT system such that each desired 2D plane of the animal is imaged in a coordinated manner with respect to the operation of the pulsed and associated optical elements.

In various aspects, the SIP-PACT system may further include one or more scanning elements configured to position (or reposition as required) the whole body of the animal relative to the focal plane of the ultrasound transducer array within the SIP-PACT to enable CT imaging. In various aspects, the scanning elements may be configured to translate the whole body of the animal to be imaged along a scanning pattern to enable a series of PA images corresponding to 2D slices through the body of the animal. The scanning pattern may be any pattern without limitation, including but not limited to step-wise movements along a linear axis of the animal. Non-limiting examples of suitable axes along which the step-wise movements of a scanning pattern may be defined include an inferior-superior axis, an anterior-posterior axis, a medial-lateral axis, or any other suitable axis defined relative to the body of the animal to be imaged. In one aspect, the scanning elements of the SIP-PACT system may be configured to translate the animal to be imaged along the animal's inferior-superior (head-toe) axis in discrete steps to enable the SIP-PACT system to obtain a series of PA images various distances along the axis. In this aspect, the one or more scanning elements may translate the whole body of the animal between a plurality of positions along the animal's inferior-superior axis in order to obtain PA images at a series of transverse planes similar to the series of PA images corresponding to transverse slices through a whole body of a mouse, as shown in FIGS. 2A, 2B, 2C, 2D, 2E, 2F and 2G.

Any known suitable scanning element may be used without limitation, in particular various scanning devices used to translate the field of view (FOV) of high-resolution imaging devices including, but not limited to, microscope scanning stages. Non-limiting examples or suitable scanning elements include: a linear microscope stage, a two-axis stage, a three-axis stage, micromanipulators, and magnetic base scanners (MBSs). In one aspect, the elements related to obtaining the PA images of the SIP-PACT system may be translated relative to a stationary animal to be imaged. In this aspect, any one or more of the pulsed lasers and associated optical elements and the ultrasound transducer array may be mounted to a scanning device to translate the imaging elements relative to the stationary animal. In another aspect, the animal to be imaged may be translated relative to stationary imaging elements of the SIP-PACT system as illustrated in FIG. 1B. In this other aspect, an animal restraint or other animal holding device may be mounted to a scanning device to translate the animal within the animal restraint or other animal holding device relative to the imaging elements.

d) Computing Device

In various aspects, the SIP-PACT system may be implemented using a computing device to enable one or more of the aspects of the SIP-PACT imaging method described herein including, but not limited to: the operation of devices such as the pulsed lasers, the ultrasound transducer array and/or the scanning elements; the processing of PA signals received from the ultrasound transducer array such as filtering, smoothing, and/or otherwise ameliorating noise, and the reconstruction of PA images from the PA signals using a reconstruction algorithm such as a dual speed-of-sound (SOS) universal reconstruction algorithm.

Figure 17:
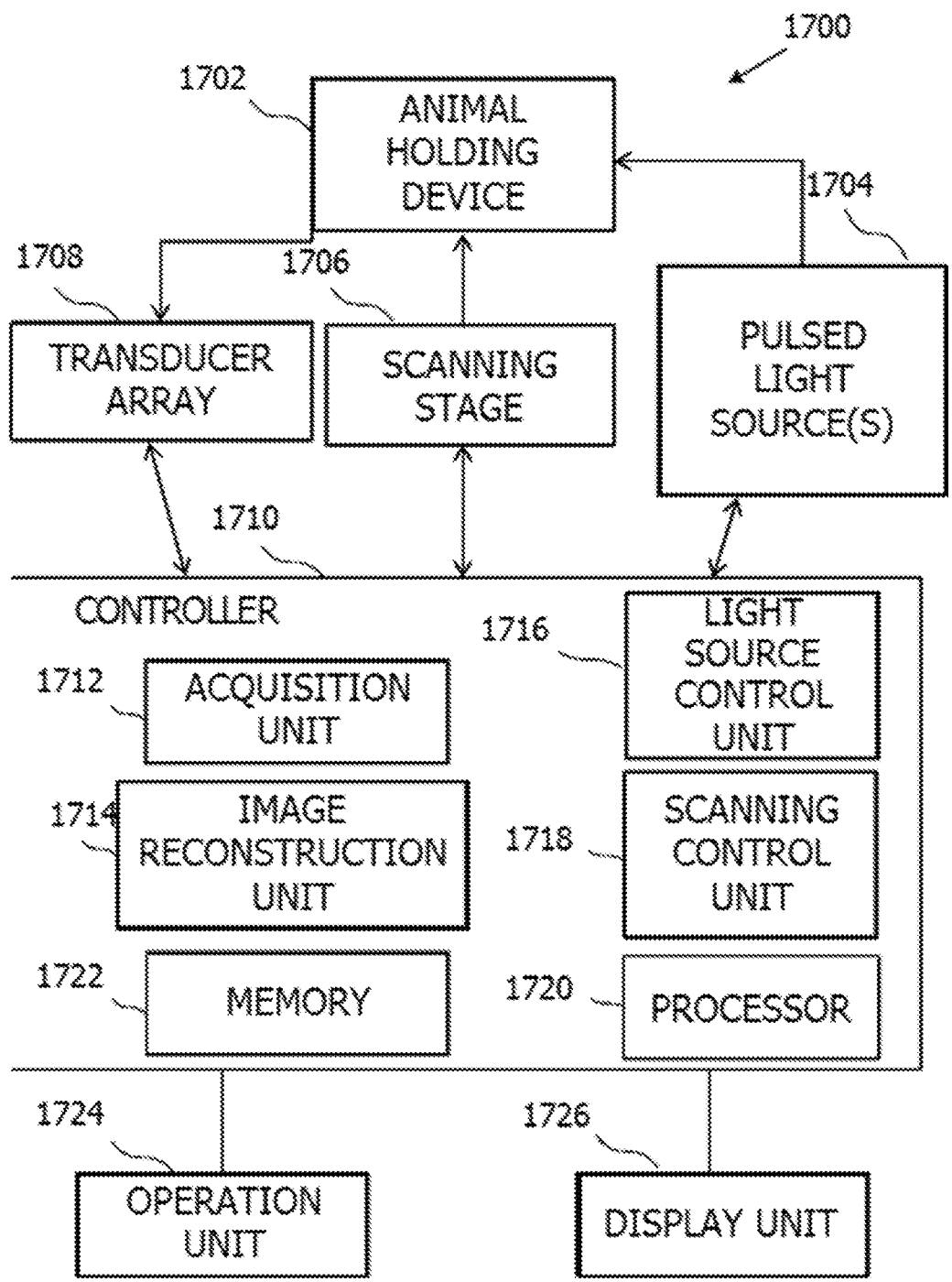
FIG. 17 is a block diagram illustrating elements of a SIP-PACT system for obtaining an attenuation map for PET imaging using DUFA-MUTE MR imaging data in one aspect.

FIG. 17 is a block diagram of a simplified SIP-PACT system 1700 in one aspect. The SIP-PACT system 1700 may include an animal holding device 1702 configured to releasably restrain a whole body of an animal within an optically and acoustically transparent coupling medium including, but not limited to water in a water tank as described herein above. The SIP-PACT system 1700 may also include: at least one pulsed light source 1704 configured to direct laser pulses into the tissues of the animal to be imaged using the SIP-PACT system 1700; a scanning stage 1706 configured to translate the animal holding device 1702 and/or pulsed light sources 1704 and transducer array 1708 as described herein above; a transducer array 1708 configured to detect a plurality of PA signals in the form of ultrasound waves emitted from the tissues of the animal in response to illumination by the pulsed light sources 1704, and a controller 1710 configured to perform a variety of control and data processing functions associated with the operation of the SIP-PACT system 1700. In some aspects, the components of the SIP-PACT system 1700 may be combined and/or separated in alternative arrangements without limitation. In other aspects, the SIP-PACT system 1700 may include additional elements configured to provide support and/or additional capabilities for the elements of the SIP-PACT system 1700 shown in FIG. 17.

Referring again to FIG. 17, the animal holding device 1702 may be any suitable animal holder or animal restraint without limitation, so long as the animal holding device 1702 is constructed of one or more materials that are optically transparent at the laser pulse wavelengths of the one or more pulsed light sources 1704 and are also acoustically transparent to ultrasound waves produced by the tissues of the animal in response to illumination by the one or more light pulses, as described herein above. In some aspects, the animal holding device 1702 may incorporate an acoustic coupling material including, but not limited to, water that may be provided in the form of a water tank as illustrated in FIG. 1A and FIG. 1B. In another additional aspect, the animal holding device 1702 may be operatively coupled to the scanning stage 1706, thereby enabling the animal holding device 1702 and animal to be imaged to be repositioned or moved in a scanning pattern in various aspects as described herein above.

In another aspect, the pulsed light source(s) 1704 may include one or more pulsed light sources including, but not limited to, pulsed lasers configured to deliver light pulses suitable for PA imaging into the tissues of an animal to be imaged. On one aspect, if the pulsed light source 1704 includes at least two pulsed lasers, each of the pulsed lasers may produce laser pulses with different laser pulse wavelengths as described herein above. The pulsed light source(s) 1704 may further include one or more optical elements operatively coupled to the pulse laser(s) and the animal holding device 1702. In an aspect, the optical elements included in the pulsed light source(s) 1704 may be configured to direct the laser pulses produced by the one or more pulsed lasers into the tissue of the animal to be imaged as described herein above. In other additional aspects, the pulsed light source 1704 may be operatively coupled to the scanning stage 1706 to enable the pulsed light source 1704 to be repositioned in a spatially coordinated manner with the animal holding device 1702 and the transducer array 1708. In one non-limiting example, the pulsed light source(s) 1704 may be repositioned using the operatively coupled scanning stage 1706 to enable SIP-PACT imaging at two or more transverse planes within a brain of the animal, as illustrated schematically in FIG. 1A.

In an additional aspect, the transducer array 1708 may be configured to detect a plurality of PA signals in the form of ultrasound waves produced within the tissues of animal to be imaged in response to illumination by laser pulses from the pulsed light source 1704. Any suitable transducer array as described herein above may be provided as the transducer array 1708 without limitation. In an aspect, the transducer array 1708 may be configured to receive and/or to periodically capture the output signal to be sent to the controller 1710 for image processing. In other aspects, the transducer array 1708 may be operatively coupled to the scanning stage 1706 to reposition the transducer array 1708 in a coordinated manner with the animal holding device 1702 and the pulsed light sources 1704. By way of non-limiting example, a transducer array 1708, provided in the form of a linear transducer array characterized by a limited field of view, may be repositioned to at least one additional position to obtain PA signals from a combined field of view that encompasses the entire region to be imaged within the animal.

Referring again to FIG. 17, the controller 1710 may be configured to communicate with the pulsed light source 1704, the scanning stage 1706, and the transducer array 1708 to send control signals to operate the various devices of the system 1700 and to receive data including, but not limited to, a plurality of PA signals used to produce PA images as well as sensor data used to monitor the function of various devices of the system 1700 and to provide feedback data used to inform various control schemes for the various devices of the system 1700. Without being limited to any particular theory, the feedback data may include a plurality of sensor signals produced by sensors encoding a state of a particular device of the system 1700. Non-limiting examples of states of elements encoded by the feedback data include: a position of an element, a temperature of an element, an activated or deactivated status of an element, an error signal generated by a device of the system 1700, and/or any other relevant states of the system 1700.

In an aspect, the controller may coordinate the timing and duration of the operation of the various devices of the SIP-PACT system 1700 to enable the generation and detection of PA signals from within the animal positioned within the animal holding device 1702. In one aspect, the controller 1700 may optionally include a timer device (not shown) to further enable the coordinating timing of the operation of various devices of the system 1700.

Referring again to FIG. 17, the controller 1710 may include an acquisition unit 1712, an image processing unit 1714, a light source control unit 1716, a scanning control unit 1718, at least one processor 1720, and a memory 1722. In one aspect, the controller 1710 may be a computing device that further includes an operation unit 1724 and a display unit 1726. In another aspect, the at least one processor 1720 of the controller 1710 may include the image processing unit 1712, the acquisition unit 1714, the light source control unit 1716, and/or the scanning control unit 1718.

The acquisition unit 1712 may be configured to coordinate the operation of various devices associated with the initial conditioning and transfer of signals including, but not limited to, electrical voltages encoding PA signals as detected by the transducer array 1708 in various aspects. Non-limiting examples of initial data conditioning include: data filtering, Fourier transforming, and any other suitable data conditioning method.

In one aspect, the acquisition unit 1712 may be configured to operate signal processing devices including, but not limited to a plurality of pre-amps, one or more analog-to-digital converters (ADC), one or more data buffer devices, and one or more data storage devices associated with processing signals encoding measurements obtained by various devices of the system 1700 and associating the encoded measurements with one or more indices or labels to identify the source and/or intended use of the encoded measurements. In an additional aspect, the acquisition unit 1712 may be configured to receive a plurality of PA signals and associate each PA signal with an index identifying the individual transducer within the transducer array 1708 at which each PA signal was detected. In at least some aspects, the acquisition unit 1712 may be configured to receive the output signals including, but not limited to PA measurements, for analysis prior to transmitting the output signals to the image processing unit 1712. In other aspects, the acquisition unit 1712 may be configured to transmit acquisition data associated with the output signals to the image processing unit 1712.

The image processing unit 1714 may be configured to receive the output signal to produce an image to be displayed. In one aspect, the image processing unit 1714 may be configured to process the PA signals received from the transducer array 1708 via the acquisition unit 1712 to reconstruct at least one 2-dimensional PA image according to an image reconstruction method, described in additional detail herein below. In one aspect, the PA signals may be used to reconstruct a series of 2-dimensional images representing a view of the structures within the same viewing plane, each 2-dimensional image-representing frame corresponding to one time point from within a cumulative time range associated with all 2-dimensional images in the series. In another aspect, the PA signals may be used to reconstruct a series of 2-dimensional images, and each 2-dimensional image represents a view of the structures within a single viewing plane from a set of viewing planes defined along an axis that is mutually perpendicular to all viewing planes in the series. In this other aspect, the series of 2-dimensional images from the series of viewing planes may be combined to form a three-dimensional image of the combined volume encompassed by the series of viewing planes.

In an additional aspect, the image processing unit 1714 may further condition the PA images to produce other PA images encoding or highlighting different aspects of structures within the field of view of the PA image. In one aspect, a reconstructed PA image may be subjected to additional conditions to produce additional 2-dimensional PA images with varying contrast schemes.

By way of non-limiting example, a set of Hessian-based Frangi vesselness filters may be applied at different scales to various reconstructed 2D PA images, and the filtered PA images may be summed or averaged pixel-wise to produce a 2-D anatomical image. In this example, the same Hessian-based Frangi vesselness filters may be applied for both the negative and positive components of each input PA image to account for the bipolar nature of PA signals, which are characterized by relatively high most negative and positive values corresponding to regions with relatively large optical absorption. In various aspects, the filter scales used in all the enhanced images described herein range from about 0.01 mm to about 1.5 mm. In various other aspects, the filter scales may be about 0.05 mm, about 0.10 mm, about 0.15 mm, about 0.20 mm, about 0.50 mm, about 0.75 mm, about 1.00 mm, and about 1.25 mm. In yet another aspect, the filter scales may be chosen empirically. In this other aspect, the filter scales may be chosen empirically to cover the range of one half to ten times the quantified resolution. In various aspects, this contrast enhancement technique is nonlinear, and therefore unsuitable for use in quantitative analyses.

As shown in FIGS. 26A, 26B, 26C, 26D, 26E, and 26F, the anatomical structures in both the original bipolar images (FIGS. 26B, 26D, and 26E) and enhanced unipolar images (FIGS. 26A, 26C, and 26F) match well with each other.

Referring again to FIG. 17, the light source control unit 1716 may be configured to operate the at least one pulsed light source 1704 in a coordinated manner and with suitable laser pulse characteristics for singe-wavelength and/or multiple-wavelength PA imaging as described herein above. In an aspect, the light source control unit 1716 may produce one or more control signals encoding operational parameters for the one pulsed light source 1704 including, but not limited to: pulse fluence, pulse width, pulse frequency, pulse wavelength, relative timing of pulse production by two or more pulsed light sources, and any other relevant operational parameter. In an aspect, the light source control unit 1716 may be further configured to monitor feedback data used to modulate the one or more control signals produced by the light source control unit 1716. Non-limiting examples of suitable feedback data includes signal, light intensity at the light source, temperature of the light source, electrical signals such as currents or voltages associated with the operation of the pulsed light sources 1704, and any other relevant feedback data.

The scanning control unit 1718 may be configured to control the operation of the scanning stage 1706 to enable the various types of SIP-PACT imaging accomplished by the SIP-PACT system 1700. By way of non-limiting example, the scanning control unit 1718 may produce a series of control signals encoding a series of commands received by one or more actuators of the scanning stage 1706 to reposition the animal holding stage 1702 so that a preselected transverse plane of the animal is aligned with the imaging plane of the transducer array 1708. In this non-limiting example, the scanning control unit 1718 may produce an additional series of control signals to maintain the preselected transverse plane of the animal in alignment with the imaging plane of the transducer array 1708. The series of PA images reconstructed from the PA signals obtained in this way represent a series of images associated with different times within a cumulative data acquisition period of the system 1700.

By way of another non-limiting example, the scanning control unit 1718 may produce a series of control signals encoding a series of commands received by one or more actuators of the scanning stage 1706 to reposition the animal such that each data acquisition cycle is conducted with a different transverse plane of the animal aligned with the imaging plane of the transducer array 1708. In this example, the timing of the movements of the animal within the animal holding device 1702 may be coordinated with the operation of the pulsed light sources 1704 and transducer array 1708 to ensure that the animal is maintained in a stationary position during each data acquisition cycle. In this example, the series of PA images reconstructed from the PA signals obtained in this manner represent views within various transverse planes within the animal that may be reconstructed into a 3-dimensional image of a volume of the animal encompassed by the range of transverse planes imaged by the system 1700.

The processor 1720 may include any type of conventional processor, microprocessor, or processing logic that interprets and executes instructions. Processor 1720 may be configured to process instructions for execution within the controller 1710, including instructions stored in the memory 1722 to display graphical information for a GUI on an external input/output device, such as display unit 1726 coupled to a high speed interface. In other implementations, multiple processors and/or multiple buses may be used, as appropriate, along with multiple memories and/or types of memory. In addition, multiple controllers 1710 may be connected, with each controller device providing portions of the necessary operations (e.g., as a server bank, a group of blade servers, or a multi-processor system). In some aspects, the processor 1720 may include the acquisition unit 1712, the image processing unit 1714, the light source control unit 1716, and/or the scanning control unit 1718.

The memory 1722 facilitates data storage in the SIP-PACT system 1700. In some aspects, the memory 1722 includes a plurality of storage components such as, but not limited to, a hard disk drive, flash memory, random access memory, and a magnetic or optical disk. Alternatively or additionally, the memory 1722 may include remote storage devices such a server in communication with the controller 1710. The memory 1722 stores at least one computer program that, when received by the at least one processor, cause the at least one processor to perform any of the functions of the controller 1710 described above. In one implementation, the memory 1722 may be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product may also contain instructions that, when executed, perform one or more functions, such as those described herein. The information carrier may be a non-transitory computer- or machine-readable medium, such as the memory 1722 or memory on the processor 1720. Additionally, the memory 1722 may be configured to facilitate storage of a plurality of PA images obtained from an animal positioned within the animal holding device 1702 as processed by the controller 1710.

The operation unit 1724 may be configured to enable a user to interface (e.g., visual, audio, touch, button presses, stylus taps, etc.) with the controller 1710 to control the operation of the SIP-PACT system 1700. In some aspects, the operation unit 1724 may be further coupled to the animal holding device 1702, transducer array 1708, scanning stage 1706, and/or pulsed light source(s) 1704 to control the operation of the respective devices of SIP-PACT system 1700 during operation.

The display unit 1726 may enable a user to view data and control information of the SIP-PACT system 1700. The display unit 1726 may further be coupled to other components of the SIP-PACT system 1700 such as the animal holding device 1702. The display unit 1726 may include a visual display such as a cathode ray tube (CRT) display, liquid crystal display (LCD), light emitting diode (LED) display, or "electronic ink" display. In some aspects, the display unit 1726 may be configured to present a graphical user interface (e.g., a web browser and/or a client application) to the user. A graphical user interface may include, for example, an image display for images acquired by the SIP-PACT system 1700 of an animal positioned within the animal holding device 1702, and operational data of the SIP-PACT system 1700.

As used herein, a processor such as the processor 1720 may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As described herein, computing devices and computer systems include a processor and a memory. However, any processor in a computer device referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

II. PA Image Reconstruction Method

Referring again to FIG. 17, the image reconstruction unit 1714 of the controller 1710 of the SIP-PACT imaging system 1700 may reconstruct the PA signals detected by the transducer array 1708 into a 2-dimensional or 3-dimensional PA image according to a PA image reconstruction method. In various aspects, the PA signals may be conditioned by the acquisition unit 1712 as described herein above prior to reconstruction of the PA image. The image reconstruction unit 1714 may make use of any suitable PA image reconstruction method including, but not limited to, a universal back-projection method, and a dual-speed-of-sound (dual-SOS) PA reconstruction method.

In some aspects, the PA reconstruction method provided for the image reconstruction unit 1714 may be a universal back-projection method. However, the universal back-projection method assumes a homogeneous composition of the animal tissues characterized by a constant speed of sound (SOS) throughout the reconstructed imaging area. However, without being limited to any particular theory, it is assumed that whole-body imaging, as conducted by the SIP-PACT system in various aspects, may include a heterogeneous distribution of tissues and cavities with differing SOS such as bone tissue and air-filled sacs such as the lungs within the imaging region. As a result, the use of the universal back-projection method may introduce uncertainty into the reconstructed PA images associated with SOS heterogeneity within the field of view of the system.

Without being limited to any particular theory, various existing image reconstruction methods have made use of different approaches to address the uncertainties of image resolution associated with SOS heterogeneity within the field of view of a PA imaging system. These existing methods rely either on iterative SOS corrections or incorporate additional hardware and software to directly measure and map the spatial distribution of the SOS within the imaging region of the PA imaging device, referred to herein as a SOS map. Both approaches dramatically increase the complexity of signal demodulation and image reconstruction, rendering these approaches impractical and potentially limiting for use in the high frame rate and high-resolution PA CT imaging accomplished by the SIP-PACT system disclosed herein.

To improve the quality of reconstructed PA images that include SOS heterogeneity within the imaging region, a dual-SOS PA image reconstruction method may be used by the image reconstruction unit 1714 in an aspect. In this aspect, the use of the dual-SOS PA reconstruction method may impose no additional computational cost to the task of PA image reconstruction by the image reconstruction unit 1714 relative to the UPB algorithm used for PA image reconstruction in previous PA imaging systems. By correcting only first-order errors introduced by SOS heterogeneity, as described herein below, it was discovered unexpectedly that the dual SOS PA reconstruction method significantly enhanced the quality of reconstructed PA images relative to PA images reconstructed using the UBP reconstruction method with minimal added computational cost. Without being limited to any particular theory, the SOS heterogeneity within an imaging region that includes a water region and a tissue region is significantly more pronounced (i.e. constitutes a first-order effect), whereas the SOS heterogeneity within an imaging region with several tissue types may be significantly less pronounced. By way of non-limiting example, the SOS of water, the liver, and the kidney are 1480 m/s, 1590 m/s, and 1570 m/s, respectively.

FIG. 10A is a schematic illustration of the factors associated with the dual-SOS reconstruction method. Referring to FIG. 10A, the imaging region 106 of SIP-PACT system may be segmented into two zones: a tissue zone 1002 and a water zone 1004. The dual-SOS reconstruction method assumes uniform SOS within each zone 1002/1004, but is different across the zones 1002/1004. The dual-SOS reconstruction method further assumes that the cross-sectional profile of the animal's body within the imaging region may be approximated by an ellipse characterized by a center position $(x_0, y_0)$ and major and minor radii $(R_x, R_y)$. In addition, refraction at the interface boundary between the tissue zone 1002 and the water zone 1004 is neglected in an aspect. As a consequence, rays representing the propagation of sound within this dual-SOS medium travel straight from the sound source location $(x_s, y_s)$ to a detector location $(x_d, y_d)$. Without being limited to any particular theory, the neglect of refraction effects in the dual-SOS image reconstruction method of dual SA second was demonstrated to reconstruct PA images of sufficient accuracy, according to a simple geometrical analysis (not shown).

Given the simplifying assumptions summarized in FIG. 10A, the sound propagation delay between any source-detector pair within the imaging region may be determined and summarized in the form of a delay map, assuming that the SOS within the tissue region 1002 is $V_1$ and the SOS within the water region is $V_2$. The delay map generated in the dual-SOS reconstruction method may be substituted in the place of the single-SOS delay map typically used in UBP reconstruction methods. It is to be noted that if a series of images are obtained at, or close to, a fixed elevational position, as is the case with the acquisition of a time-series of 2-dimensional images, the delay map may calculated once for a single 2-dimensional imaging plane, and the saved delay map may be reused in the reconstruction of subsequent PA images, without need for additional measurement and analysis associated with the development of a delay map. In the case of a 3-dimensional image, a series of delay maps may be reused in the reconstruction of subsequent PA images obtained at imaging planes that are relatively close to an imaging plane corresponding to one of the saved delay maps. The delay map generated by the dual-SOS assumption may be used to reconstruct images with no additional computational cost.

In various aspects, the dual-SOS image reconstruction method is a modification of an existing universal back-projection (UPB) image reconstruction method. The UPB reconstruction method makes use of a single-SOS delay map that includes the elapsed time for a PA signal originating at a plurality of PA source positions $(x_s, y_s)$ within the imaging region of the PA imaging device to travel to each detector in a detector array situated at each detector position $(x_d, y_d)$ assuming a uniform SOS throughout the imaging region.

The dual-SOS image reconstruction method produces a dual-SOS delay map that includes the same elapsed times for the PA signal to propagate from all combinations of PA source positions $(x_s, y_s)$ and all detector positions $(x_d, y_d)$. This dual-SOS delay map is substituted for the single-SOS delay map used in the existing UPB method as described herein above, and the remaining steps of the UPB reconstruction method are conducted as previously described to reconstruct the PA images.

Figure 18:
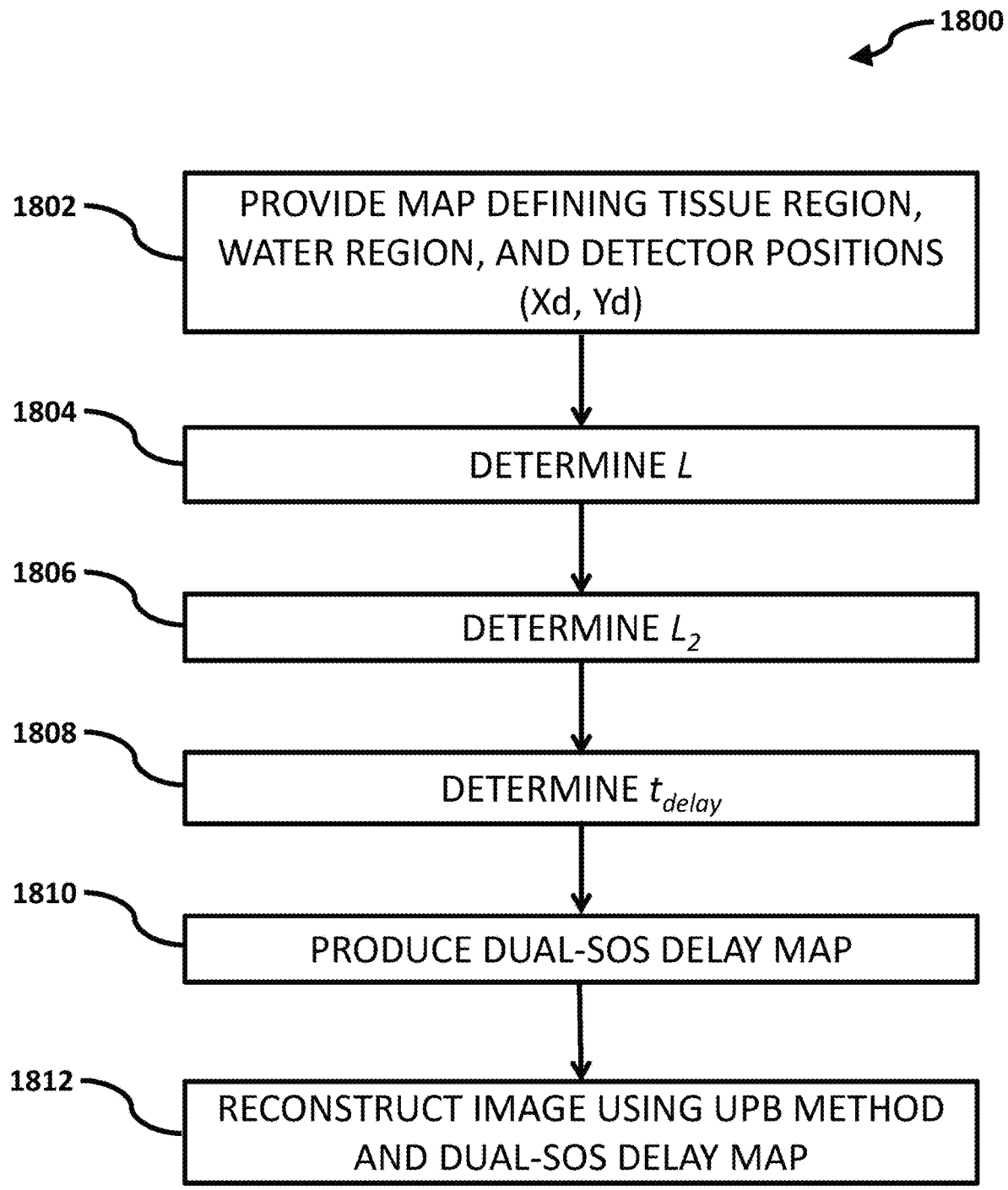
FIG. 18 is a flow chart describing the steps of a dual-SOS image reconstruction method in one aspect.

FIG. 18 is a flow chart summarizing the steps of a dual-SOS image reconstruction method 1800 in an aspect. Referring to FIG. 18, the dual-SOS image reconstruction method 1800 includes providing a map 1006 defining the tissue region 1002, the water region, 1004 and the positions of each individual transducer $(x_d, y_d)$ in the transducer array. Referring again to FIG. 10, the tissue region 1002 may be defined as an elliptical area positioned within a circular water region 1004. The center of the circle defining the circular water region 1004 is defined as the origin (x,y)=(0, 0) of the coordinate system of the map 1006. The elliptical area representing the tissue region 1002 is centered at an arbitrary position $(x_o, y_o)$ anywhere within the circular water region 1004 so long as the entire elliptical tissue region 1002 is contained completely within the water region 1004 in various aspects. The elliptical tissue region 1002 is further characterized by a semi-major axis distance $R_x$ and a semi-minor axis distance $R_y$.

Referring again to FIG. 10A, all source positions $(x_s, y_s)$ from which PA signals are produced are constrained to fall within the elliptical tissue region 1002 in various aspects. Without being limited to any particular theory, it is assumed that the PA signals detected by the SIP-PACT system 1700 result from the illumination of structures within the whole body of the animal (i.e. from somewhere within the animal's tissues), which equates to an $(x_s, y_s)$ falling within the elliptical tissue region 1102 defined in FIG. 10A.

Referring again to FIG. 10A, any PA signal originating from a source position $(x_s, y_s)$ travels a total distance L to be detected by a detector positioned at $(x_d, y_d)$. This total distance L may be divided into a sum of two intermediate distances: $L_1$, the distance traveled through the tissue region 1002 at the tissue SOS $V_1$ and $L_2$, the distance traveled through the water region 1004 at the water SOS $V_2$. It is to be noted that the dual-SOS image reconstruction method 1800 neglects the effects of diffraction of the PA signal path at the tissue-water interface boundary 1010. As a result, all PA signals are assumed to travel a straight-line path from $(x_s, y_s)$ to each detector at position $(x_d, y_d)$.

Referring again to FIG. 18, the dual-SOS image reconstruction method 1800 further includes determining the total distance L traveled by each PA signal from the PA signal source position $(x_s, y_s)$ to each detector at position $(x_d, y_d)$ at 1804. In one aspect, the distance L may be calculated at 1804 according to Eqn. (1):

$$L=\sqrt{(x_d-x_s)^2+(y_d-y_s)^2} \quad \text{Eqn. (1)}$$

The dual-SOS image reconstruction method 1800 further includes determining the distance $L_1$ traveled by each PA signal from the PA signal source position $(x_s, y_s)$ to a tissue-water interface position $(x_{twi}, y_{twi})$ at 1804. In this aspect, the tissue-water interface position $(x_{twi}, y_{twi})$ represents the intersection of the straight-line signal path traveled by the PA signal with the tissue-water interface 1010 (see FIG. 10).

In one aspect, the tissue-water interface position $(x_{twi}, y_{twi})$ may be calculated using a series of equations derived from the a geometrical analysis of the map 1006 defining the positions of the tissue region 1002 within the water region 1004 as well as the coordinates describing the elliptical shape of the tissue region 1002. In this aspect, the slope k and intercept b of the signal path may be determined according to Eqn. (2) and Eqn. (3) below:

$$k = \frac{y_d - y_s}{x_d - x_s} \quad \text{Eqn. (2)}$$

$$b = y_s - kx_s \quad \text{Eqn. (3)}$$

Given the slope and intercept of the straight-line signal path, the x-coordinate of the intersection of this signal path with tissue-water interface $x_{twi}$ may be calculated using Eqns. (4), (5), (6), and (7):

$$A = \frac{1}{R_x^2} + \frac{k^2}{R_y^2} \quad \text{Eqn. (4)}$$

$$B = 2\left(\frac{k(b-y_0)}{R_y^2} - \frac{x_0}{R_x^2}\right) \quad \text{Eqn. (5)}$$

$$C = \frac{x_0^2}{R_x^2} + \frac{(b-y_0)^2}{R_y^2} - 1 \quad \text{Eqn. (6)}$$

$$x_{twi} = -B \pm \frac{\sqrt{B^2 - 4AC}}{2A} \quad \text{Eqn. (7)}$$

Note that Eqn. (7) yields two values for $x_t$, in the aspect. Accordingly, the $x_{twi}$-value that satisfies Eqn. (8) is selected from the two values of $x_{twi}$ provided by Eqn. (7):

$$(x_s - x_{twi})(x_{twi} - x_d) > 0 \quad \text{Eqn. (8)}$$

Given the elliptical boundary of the tissue region 1002 is defined as an ellipse with center $(x_o, y_o)$, semi-major axis distance $R_x$ and semi-minor axis distance $R_y$, the y-coordinate of the intersection of this signal path with tissue-water interface $y_{twi}$ may be calculated according to Eqn. (9):

$$y_{twi} = 2\left(\frac{(b-x_{twi})}{R_x^2} - \frac{y_0}{R_y^2}\right) \quad \text{Eqn. (9)}$$

In this aspect, once $(x_{twi}, y_{twi})$ has been determined as described herein above, $L_1$ may be calculated at 1804 according to Eqn. (10):

$$L_1 = \sqrt{(x_{twi}-x_s)^2+(y_{twi}-y_s)^2} \quad \text{Eqn. (10)}$$

Referring again to FIG. 18, the dual-SOS image reconstruction method 1800 further includes determining the distance $L_2$ traveled by each PA signal from the tissue-water interface position $(x_{twi}, y_{twi})$ to the position of each detector $(x_d, y_d)$ at 1806. In one aspect, the distance $L_2$ may be determined according to Eqn. (11):

$$L_2 = L - L_1 \quad \text{Eqn. (11)}$$

Referring again to FIG. 18, the dual-SOS image reconstruction method 1800 further includes determining the delay time $t_{delay}$ at 1808. As used herein, $t_{delay}$ refers to the total elapsed time from the time a PA signal is produced at a source position $(x_s, y_s)$ to detection time at which the PA signal is detected by a detector positioned at $(x_d, y_d)$. In one aspect, the delay time $t_{delay}$ may be determined according to Eqn. (12):

$$t_{delay} = \frac{L_1}{V_1} + \frac{L_2}{V_2} \qquad \text{Eqn. (12)}$$

In various aspects, the $t_{delay}$ determined at 1808 corresponds to a single PA signal travelling to a single detector in the detector array. For each PA signal produced at one source position $(x_s, y_s)$, there exist N delay times $t_{delay}$, corresponding to the N detectors in the detector array. In addition, within the tissue region 1002, M different possible PA signal source positions $(x_d, y_d)$ may be defined. In one aspect, the delay map may include the delays for PA signals produced at M possible PA signal source positions $(x_d, y_d)$ to be received at all N detectors at all possible detector positions $(x_d, y_d)$ in the detector array. In this aspect, the detector map may include a total of N×M delay times.

Referring again to FIG. 18, the dual-SOS image reconstruction method 1800 further includes producing a dual-SOS delay map at 1810 in an aspect. In this aspect, the delay map may be produced by combining all possible delay times as described above. In one aspect, the delay map may be produced in the form of a delay time database that includes a plurality of delay time entries. Each delay time entry may include a single PA signal source positions $(x_d, y_d)$ followed by N delay times, in which each of the N delay times corresponds to a single detector with the detector array. In addition, the delay map may further include a detector array table providing a means of associating the delay times in each delay time entry to the appropriate detector in the detector array.

As shown in FIG. 18, the dual-SOS image reconstruction method 1800 further includes reconstructing an image using the universal back-projection (UPB) method as described herein above at 1812.

Although the above description of the dual-SOS image reconstruction method 1800 was described in the context of an elliptical tissue region 1002 within a circular water region 1004, it is to be understood that the dual-SOS image reconstruction method 1800 may be modified as needed to render the method compatible with different sizes and/or shapes of tissue regions 1002 and water regions 1004. By way of non-limiting example, the tissue region 1002 may be defined to have a non-elliptical profile and/or the water region 1004 may be defined to have a non-circular profile. Any arbitrary profile shape may be used to define the profiles of the tissue region 1002 and/or water region 1004, so long as there exists a means of determining the (x,y) coordinates of the tissue-water interface 1010.

In addition, it is to be understood that the dual-SOS image reconstruction method 1800 may be expanded to incorporate one or more additional regions with different SOS. By way of non-limiting example, a bone region may be defined within the tissue region 1002 in an aspect with a bone-specific SOS. In this aspect, the method 1800 may further include determining an addition portion of the delay time associated with the travel of the PA signal through the bone region.

III. Visualization Using SIP-PACT System

In various aspects, the SIP-PACT system may be used to perform imaging and computed tomography directed to visualize changes in various structures over time with relatively high resolution, as well as detailed 2-dimensional and 3-dimensional images with various endogenous and exogenous contrasts. In one aspect, the SIP-PACT system may be used to perform 2-dimensional temporally resolved PA imaging of whole-body dynamics as described herein above and in the examples provided herein below.

In another aspect, the SIP-PACT system may be used to noninvasively map the whole-body arterial network and measure the relative difference in the phase of the pulse waves of the arteries using the pulse-contrast PA imaging as described herein above and in the examples provided herein below. This capability may provide a non-invasive and direct diagnostic tool for chronic coronary artery disease and chronic renal disease. Aortic pulse wave measurement and analysis have been widely used to study cardiovascular diseases in both clinical and preclinical researches. With a frame rate of 50 Hz, the SIP-PACT system may reveal whole-body cardiac related dynamics and may selectively map the whole-body arterial network in animals such as mice. Relatively steady phase delays between arteries within internal organs may also be computed, which may indicate changes in the cross-sectional areas resulting from pulse wave propagation through the arterial network. Thus, the capability of mapping the arterial network and the relative phase delay distribution within each cross-section enables SIP-PACT to be a potential non-invasive tool for direct diagnosis of chronic coronary artery disease and chronic renal disease.

In another aspect, the SIP-PACT system may be used to perform functional imaging including, but not limited to, the measurement of blood oxygen level in the brain and body, thereby providing an effective means to access neural activity and whole-body metabolism. Leveraging the absorption spectral difference between oxy-hemoglobin and deoxy-hemoglobin, the SIP-PACT system achieves functional imaging in both the brain and trunk, which enables applications such as monitoring hemodynamic-related metabolic activities across internal organs during chemotherapy.

In one aspect, dual-wavelength SIP-PACT may be conducted to obtain images mapping blood oxygen levels within the body of an animal including the trunk and the brain. In one aspect, the dual-wavelength SIP-PACT may be conducted using wavelengths of 630 nm and 1064 nm. The 1064 nm pulse wavelength may be selected for ready transmission through mammalian tissues, and the 630 nm wavelength may be selected for relatively high contrast between deoxy-hemoglobin (Hb) and oxyhemoglobin (HbO$_2$) (see FIG. 11A and FIG. 11B). In various aspects, other wavelength with comparable functional properties may be substituted for the 630 nm and 1064 nm wavelengths.

In an aspect, sO$_2$ may be determined according to Eqn. (13) and Eqn. (14):

$$\begin{bmatrix} C_{HbO_2} \\ C_{Hb} \end{bmatrix} = \begin{bmatrix} \varepsilon_{HbO_2} & \varepsilon_{Hb} \\ \varepsilon_{HbO_2} & \varepsilon_{Hb} \end{bmatrix}^{-1} \begin{bmatrix} PA_{630}/F_{630} \\ PA_{1064}/F_{1064} \end{bmatrix} \qquad \text{Eqn. (13)}$$

$$sO_2 = \frac{C_{HbO_2}}{C_{HbO_2} + C_{Hb}} \qquad \text{Eqn. (14)}$$

where $C_{HbO2}$ and $C_{Hb}$ are oxy-hemoglobin and deoxy-hemoglobin concentrations, respectively, $\varepsilon_{HbO2}$ and $\varepsilon_{Hb}$ are molar extinction coefficients of oxy-hemoglobin and deoxy-hemoglobin, respectively, $PA_{630}$ and $PA_{1064}$ are the photoacoustic amplitudes at the 630 nm and 1064 nm wavelengths, respectively, and $F_{630}$ and $F_{1064}$ are the optical fluences at the feature being imaged for the 630 nm and 1064 nm wavelengths, respectively.

In other additional aspects, dye perfusion within internal organs of an animal may be visualized using the SIP-PACT system with a high temporal resolution as described in the examples provided herein below. In addition, the movements of circulating melanoma cancer cells may be tracked over time using the SIP-PACT system, providing an additional ability to image metastasis. In another aspect, 3-dimensional PA imaging may be conducted using the SIP-PACT system as described herein.

EXAMPLES

The following examples illustrate various aspects of the disclosure.

Example 1: 3D Whole Body PACT Using SIP-PACT System

To demonstrate 3D whole body photoacoustic computed tomographic (PACT) imaging using the SIP-PACT system and methods described herein, the following experiments were conducted.

Figure 25:
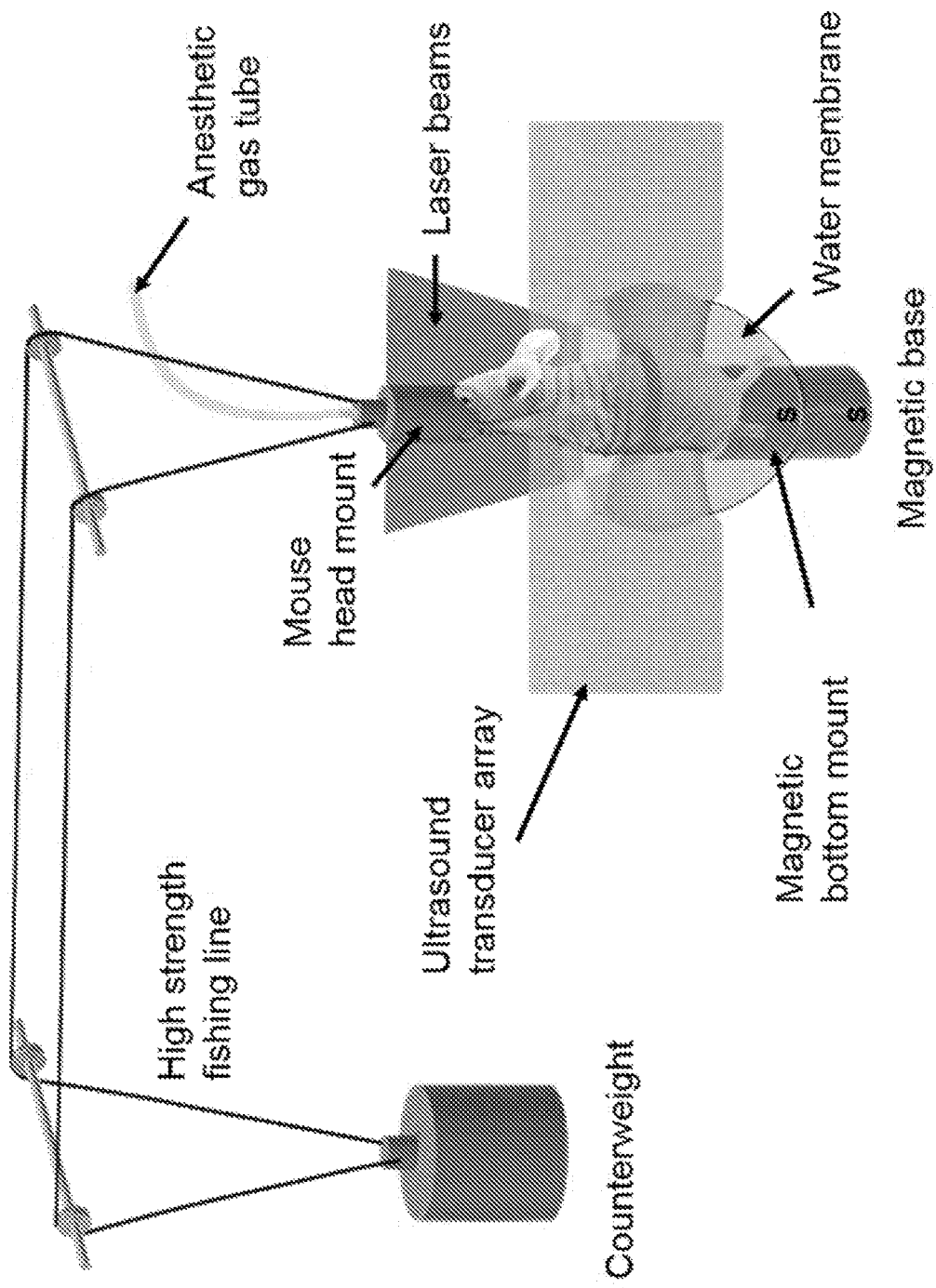
FIG. 25 is a schematic illustration of an animal holder for whole-body imaging using a SIP-PACT system according to one aspect of the disclosure.

Adult, 8-10-week old nude mice (Hsd:Athymic Nude-FoxlNU, Harlan Co.; 20-30 g body weight) were used for whole body imaging in vivo experiments. Throughout the experiment, each mouse was maintained under anesthesia with 1.5% vaporized isoflurane. For brain imaging, the mouse was secured to a lab-made imaging platform (see FIG. 25), and the cortical surface was positioned in alignment with the ring transducer array's focal plane. During the whole body imaging experiments, the mouse's fore and hind legs were respectively taped to the top and bottom parts of the lab-made holder that held the animal upright during imaging. The top of the holder included an aluminum tube affixed to the animal's nose and mouth, and the bottom of the holder included an aluminum cylinder attached to a permanent magnet base. The magnet base securely held the animal holding device to the scanning stage for elevational scanning. The top and bottom parts of the animal holding device were connected by four lengths of 4 lb. test fishing line (0.13 mm diameter braided line). Each animal's trunk was immersed in water, and its body temperature was maintained at 37° C. by circulating the water through a heating bath outside the tank.

The SIP-PACT system described herein above and illustrated schematically in FIG. 1A and FIG. 1B was used to obtain brain images and whole body images at various axial locations along each mouse's body. The SIP-PACT system included a 512-element full-ring ultrasonic transducer array (Imasonic, Inc., 5 MHz, 90% one-way bandwidth for 2D panoramic in-plane acoustic detection. Image reconstruction using the digitized raw data was performed using the dual-speed-of-sound universal back-projection algorithm described herein above. Two different illumination approaches were applied respectively for imaging the mouse brain cortex and trunk: top illumination and side detection were used for brain cortex imaging (see FIG. 1A), and full-ring side illumination and side detection (aligned confocally to maximize detection sensitivity) were used for trunk imaging (see FIG. 1B). Laser pulses with a pulse wavelength of 1064 nm and a 50 Hz repetition rate were used for all images.

FIGS. 2A, 2B, 2C, 2D, 2E, and 2F are PA images obtained non-invasively using the SIP-PACT system for transverse slices (illustrated schematically in insert drawings of mouse) of the whole body of the mice. The SIP-PACT imaged the anatomy of the brain cortex (FIG. 2A) and the internal organs within the thoracic cavity: heart (HT in FIG. 2B), lungs (LL/RL in FIGS. 2B and 2C) and the abdominal cavity (liver (LV in FIG. 2C and LLV/RLV in FIG. 2D), spleen (SP in FIGS. 2E and 2F, kidney (LK/RR in FIGS. 2E and 2F), stomach (SM in FIG. 2F), and intestine (IN in FIGS. 2E and 2F). Each entire cross-section was clearly imaged with a homogeneous ~100 μm spatial resolution, with detailed structures revealed by hemoglobin contrast. After scanning the animal vertically through the confocal plane and stacking the slices of cross-sectional images, a three-dimensional (3D) tomogram of the mouse trunk was compiled (not shown). Based on the above images, the thickest section of the mouse trunk had a diameter of ~28 mm.

These experiments demonstrated that the SIP-PACT system performed whole body PA imaging at a spatial resolution of about 100 μm.

Example 2: 2D Time-Resolved Imaging of Cardiac and Respiratory Cycles Using SIP-PACT System To demonstrate 2D whole body time-resolved imaging of cardiac and respiratory cycles using the SIP-PACT system and methods described herein, the following experiments were conducted.

Nude mice were prepared and mounted in the SIP-PACT system illustrated in FIG. 1B using a protocol similar to the protocol described in Ex. 1. The mouse was positioned in the SIP-PACT system so that the focal plane of the ring transducer array passed through the heart of the patient, resulting in a PA image similar to the PA image shown in FIG. 2B. The SIP-PACT system was operated in a manner similar to Ex. 1 using full-ring side illumination and side detection with 1064 nm laser pulses delivered at a 50 Hz repetition rate to the same transverse plane of the mouse's thoracic cavity to obtain a time-series of images.

Figure 3A:
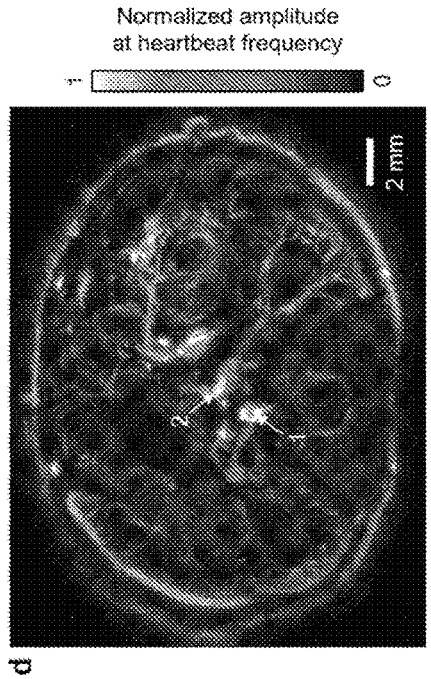
FIG. 3A is a cross-sectional label-free SIP-PACT image of an upper thoracic cavity.
Figure 3B:
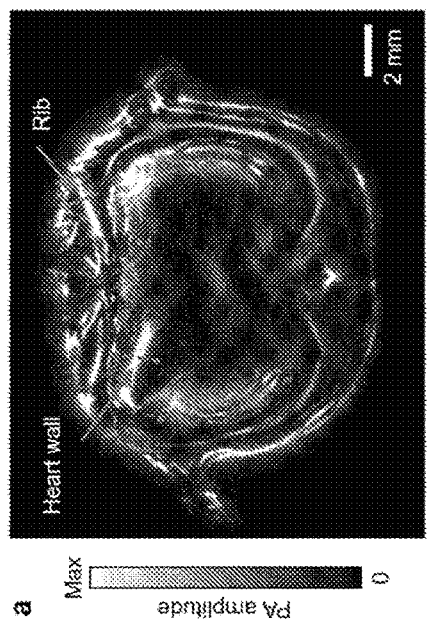
FIG. 3B is a line profile graph summarizing trajectories of a rib during respiration (top graph) and heart wall over numerous heartbeats (bottom graph) obtained by analysis of a series of images similar to the image of FIG. 3A obtained over an acquisition time of about 5 seconds.
Figure 3D:
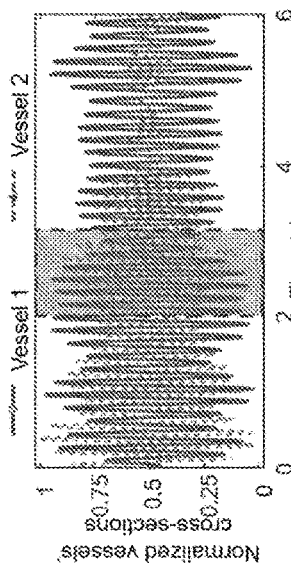
FIG. 3D is an anatomical image overlaid with a heartbeat-encoded arterial network mapping.
Figure 3E:
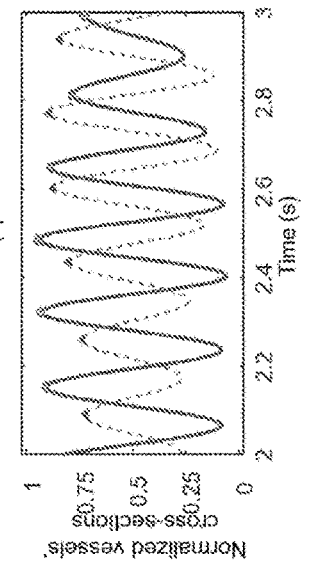
FIG. 3E is a graph of changes in the cross-sections of each of two vessels denoted by arrows in FIG. 3D, showing the changes in vessel cross-section associated with arterial pulse propagation.
Figure 3C:
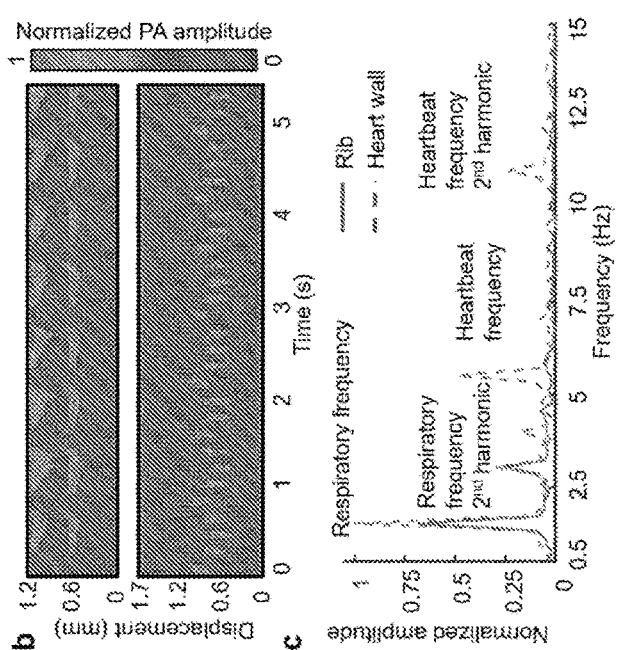
FIG. 3C is a graph illustrating frequency spectra (normalized amplitudes of Fourier transforms versus frequency (Hz)) of the rib and heart wall movements showing the distribution of respiratory and heartbeat frequencies, respectively.

FIG. 3A is a representative image of the transverse slice through the thoracic cavity of the mouse. At an imaging frame rate of 50 Hz, respiratory motions and heartbeats were fully captured. To quantify the motion in the thoracic cavity, changes in PA signals along a solid red transect line overlaid on FIG. 3A (corresponding to a rib) and along a dashed blue transect line overlaid on FIG. 3A (corresponding to a heart wall) over the time-series of PA images were analyzed to identify and track respiratory motion and heartbeats, respectively. The PA signals along the transect lines indicated in FIG. 3A were extracted and the primary PA signal peaks in each frame were tracked. FIG. 3B are maps of the PA amplitudes as a function of distance along the transect (trajectory, vertical axis) and time (horizontal axis) for the red transect (top map) and for the blue transect (bottom map). For each transect line examined, the PA signal peak's position formed a time trace that was transformed into the temporal frequency domain via Fourier transform, where the respiratory frequency components and/or the heartbeat frequency components were visualized. The data mapped in FIG. 3B was subjected to Fourier analysis to generate the frequency spectra shown graphed in FIG. 3C. Fourier analysis shows that the motion of the rib (red solid line) repeated at a respiratory frequency of ~1 Hz, and the motion of the heart wall (dashed blue line) repeated at both the respiratory frequency of ~1 Hz and at a heartbeat frequency of ~5.2 Hz (FIG. 3C).

Figure 2F:
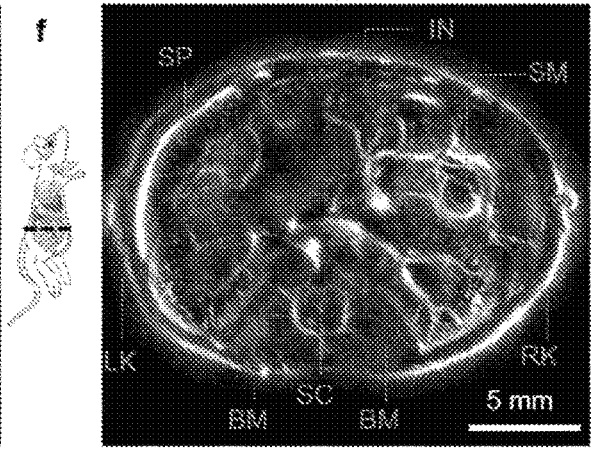
FIG. 2F is a cross-sectional label-free SIP-PACT image of a mouse lower abdominal cavity.

In addition, a motion-contrast PA image of an arterial network was produced using frequency analysis of a time series of PA images of a transverse slice through the abdominal lower cavity of the mouse (corresponding to the transverse slice image of FIG. 2F). Fourier transforms were performed on each time trace from each pixel of the time series of PA images to obtain frequency spectra for each pixel. The amplitude of PA signal variation for each pixel throughout the entire field of view (FOV) of the image that occurred at the heartbeat frequency of ~5.2 Hz was extracted from each spectrum. FIG. 3D is a motion-contrast PA image mapping the amplitude of normalized PA signal changes at the heartbeat frequency. This motion-contrast PA image selectively images the arterial network over the whole-body cross-sectional image (FIG. 3D). In particular, the renal arterial network of the right kidney is highlighted by the motion-contrast (PA signal changes at heartbeat frequencies) in FIG. 3D.

To analyze the phase delay of blood flow across different arteries in an artery network, we examined neighboring patches of the selected vertically distributed arteries, segmented the selected arteries at each frame by thresholding, and computed the cross-sectional areas of each of the selected arteries at each frame of the time series of PA images. The time series of PA images of two vertically distributed arteries from the arterial network (highlighted by arrows 1 and 2 in FIG. 3D) were analyzed to compute the changes of the cross-sectional areas over time. The changes in the cross-sectional areas of the selected arteries were then filtered with a high-pass filter to remove low-frequency interferences using a zero-phase digital filtering technique to avoid changing the phase information, with the cutoff frequency set at the halfway point between the respiratory frequency's 2nd harmonic and the heartbeat frequency. The changes in cross-sectional area for the selected arteries were normalized to 0 and 1, according to the overall minimum and maximum values, which did not alter phase information.

Figure 3F:
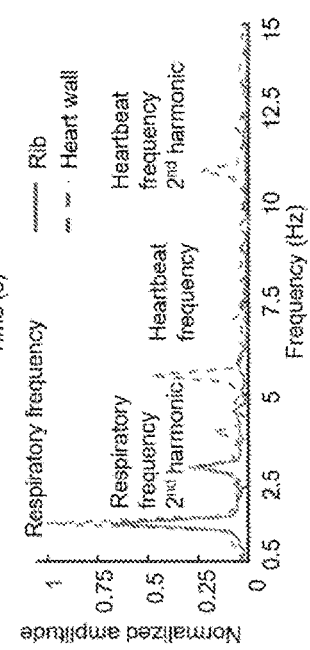
FIG. 3F is a graph showing an enlargement of the grey portion of the graph shown in FIG. 3E, highlighting the relative phase delay between the expansion-contraction cycles of the cross sections of the two vessels.

Within the cross-sectional view of lower abdominal cavity illustrated in FIG. 3D, the variations in PA signals from arteries were temporally correlated due to their direct connection to the heart. FIG. 3E is a graph of the normalized cross-sections of the marked arteries in FIG. 3D as a function of time. During systole, the aortic wall dilates due to the ejection of blood from the contracted left ventricle, generating a pressure wave that travels along the arterial tree. FIG. 3F is an enlargement of the graph of FIG. 3E, showing a steady phase delay in enlargement between vessel 1 and vessel 2, indicating that the changes of the cross-sectional areas in these vessels were likely the result of pulse waves propagating through the arterial network.

These experiments demonstrated that the SIP-PACT system enables the capture of time series PA images at a frame rate of 50 Hz and at relatively high spatial resolution. Spectral analysis of the time series PA images, such as Fourier analysis, enabled enhanced imaging capabilities, such as the mapping of whole-body arterial networks in mice using PA signal variations at the heartbeat frequency as an inherent contrast agent. Time-series analysis of the time series PA images enabled quantification of whole-body cardiac related dynamics, including phase differences in blood flow between different vessels in an arterial network.

Example 3: Functional Imaging Using SIP-PACT System

To demonstrate functional imaging using the SIP-PACT system and methods described herein, the following experiments were conducted.

Adult, 3-4-month-old Swiss Webster mice (Hsd: ND4, Swiss Webster, Harlan Co.; 20-30 g body weight) were used for in vivo functional brain and CTC imaging. Prior to brain functional imaging using the SIP-PACT system, the hair of each mouse was removed by clippers and depilatory cream. Each mouse was then secured to a lab-made imaging platform, and the brain's cortical surface was positioned aligned with the transducer array's focal plane as described in Ex. 1. Each mouse breathed an inhalation gas containing varying concentrations of oxygen to systemically modulate the oxygen saturation of hemoglobin ($sO_2$) within the mice during functional SIP-PACT imaging, as described in detail below.

A SIP-PACT system similar to the system described in Ex. 1 (see FIG. 1A) was used to obtain time series PA images of the mouse brain. For these experiments, the mouse brain was illuminated from above with two laser pulses of different wavelengths: 1064 nm and 630 nm. The 1064 nm pulse wavelength was selected for ready transmission through mammalian tissues, and the 630 nm wavelength was selected for relatively high contrast between deoxyhemoglobin (Hb) and oxyhemoglobin ($HbO_2$) (see FIG. 11A and FIG. 11B). Taking advantage of the difference in the PA signals produced by oxy-hemoglobin and deoxy-hemoglobin, oxygenation dynamics were imaged using the SIP-PACT system by eliciting PA signals from the mouse brain in response to alternate illumination by laser pulses with the two different wavelengths delivered at 10 Hz and at biologically negligible delays (50 µs) as illustrated in the inset graph of FIG. 1A.

The SIP-PACT system was used to image both the cortical vasculature and the $sO_2$ of the cortical vessels noninvasively and in vivo during an oxygen challenge administered to each mouse via manipulation of the oxygen levels in the inhalation mixture supplied to each mouse. For the first three minutes of imaging, a mixture of 95% oxygen and 5% nitrogen with gaseous isoflurane added to the inhalation mixture for anesthesia was supplied to each mouse. During the oxygen challenge, the composition of the inhalation mixture was switched to 5% oxygen and 95% nitrogen for 3 minutes (4.5 minutes for whole-body oxygen challenge), and then switched back to the initial concentration (95% oxygen and 5% nitrogen) to end the oxygen challenge.

Oxygen saturation ($sO_2$), % Hb, and % $HbO_2$ was calculated using Equations (2) and (3) disclosed herein above. To estimate PA/F for each of the wavelengths in Equation (2), all PA signal data from all channels of the ring transducer array was normalized using the signal generated at the transducer's surface. The original 4000 frames of raw data from the ring transducer array were divided into 160 bins and averaged within each bin on a per channel basis. The data cube (i.e. PA signal amplitude as a function of x,y position at a plurality of data acquisition times) was subsequently averaged along the third dimension (time) with a window size of five. Reconstructed PA images were smoothed using a Hessian filter, and several branches of vessels were segmented to display the calculated $sO_2$ in color. FIG. 4A is a map of oxygen saturation within the vessels of the brain calculated at a normoxic state prior to the oxygen challenge, and FIG. 4B is a corresponding map of oxygen saturation at a hypoxic state during the oxygen challenge. FIG. 4C is a graph of the $sO_2$ levels in the mouse brain as a function of time during the oxygen challenge, with the hypoxic period highlighted as a grey region. FIG. 4D is a graph of the individual concentrations of $HbO_2$ (blue line) and Hb (red line) corresponding to the $sO_2$ levels shown in FIG. 4C. The oxygen challenge was accompanied by a drop in $sO_2$ resulting from hypoxia, and the drop in systemic $sO_2$ level during hypoxia was manifestly slower than the return to normoxic $sO_2$ concentrations during recovery, consistent with previous observations.

Whole-body oxygen dynamics during the oxygenation challenge were assessed using a SIP-PAT system similar to the system illustrated in FIG. 1B. For the whole-body functional imaging, each whole mouse body was illuminated from the sides with two alternating laser pulses of different wavelengths: 1064 nm and 720 nm. The 1064 nm pulse wavelength was selected for ready transmission through mammalian tissues, and the 720 nm wavelength was selected for relatively high contrast between deoxyhemoglobin (Hb) and oxyhemoglobin (HbO$_2$) (see FIG. 11A and FIG. 11B). Oxygenation dynamics were imaged using the SIP-PACT system by eliciting PA signals from the mouse body at various transverse planes through the thoracic and abdominal cavities of the mouse in response to alternate illumination by laser pulses of two different wavelengths delivered at 10 Hz and at a 10 μs delay, as illustrated in the inset graph of FIG. 1B.

To quantify whole-body oxygen dynamics, the first 1000 frames (corresponding to the first 50 seconds of the experiment) of the whole-body functional images were averaged as a baseline image, and a subsequent 2500 frames (corresponding to a 2-minute period started at 3 minutes and ending at 5 min within the oxygen challenge) as an oxygen challenge signal image. A relative signal change image was computed as the difference between the baseline image and the oxygen challenge signal image. A disk filter (5 pixel/0.25 mm; Matlab Image Processing Toolbox) was applied to smooth the relative signal change image prior to overlaying the relative signal change image on the anatomy image.

FIG. 4E and FIG. 11C are representative maps of the fractional change in PA amplitude for a transverses slice through the lower abdominal cavity of a mouse. FIG. 11D is a map of the fractional change in PA amplitude for a transverses slice through the lower abdominal cavity of a mouse that includes two lobes of a liver. After switching the oxygen concentration from 95% to 5% to initiate the hypoxic phase of the oxygen challenge at t=3 minutes, the whole-body oxygenation levels decreased accordingly. Because deoxy-hemoglobin has a much stronger molar optical absorption than oxy-hemoglobin at the excitation wavelength of 720 nm (see FIG. 11A), the calculated PA signal changes reflected mainly the whole-body deoxy-hemoglobin concentration changes. In FIG. 4E, FIG. 11C, and FIG. 11D, a yellow color assigned to a pixel represents a positive relative PA signal change at that pixel, corresponding to a decrease in sO$_2$. Similarly, a blue color assigned to a pixel represents a negative relative PA signal change at that pixel, corresponding to an increase in sO$_2$.

The baseline signal images and oxygen challenge signal images obtained at various transverse cross-sections were further analyzed to calculate average normalized PA signal amplitudes for pixels within the stomach, kidney, and liver of the mouse at normoxic and hypoxic conditions. FIG. 4F is a bar graph summarizing the average normalized PA signal amplitudes for normoxic (open bars) and hypoxic (black bars) states for the stomachs, kidneys, and livers of the mice imaged in this experiment. Without being limited to any particular theory, a global shortage of oxygen supply to a mouse is thought to induce a corresponding whole-body decrease in sO$_2$. Based on the results of these experiments, a relative sO$_2$ decrease was observed in most of the organs, such as the brain (see FIG. 4C), liver, and kidney (see FIG. 4F), and a relative sO$_2$ was observed in some organs, such as the stomach (see FIG. 4F). Without being limited to any particular theory, the mouse is likely adjusting whole-body metabolic activity to survive an oxygen challenge. Because vital organs, such as the brain, heart, and kidney, must maintain basic function independently of oxygenation status, the relatively unchanged oxygen consumption during hypoxia leads to a sO$_2$ drop. Because other non-vital organs, such as the stomach, are known to regulate their metabolic activity according to need (prandial status, sympathetic/parasympathetic stimulation, etc.), reduced metabolic activity during hypoxia may result in a sO$_2$ increase within these non-vital organs.

The results of this experiment demonstrated the ability of the SIP-PACT system to obtain photoacoustic images at frame rates capable of capturing the dynamics of whole-body oxygenation distribution across internal organs in vivo and without labeling.

Example 4: Tracking of Circulating Tumor Cells (CTCs) Using SIP-PACT System

To demonstrate the tracking of circulating tumor cells (CTCs) using the SIP-PACT system and methods described herein, the following experiments were conducted.

Adult, 3-4-month-old Swiss Webster mice (Hsd: ND4, Swiss Webster, Harlan Co.; 20-30 g body weight) were used for the in vivo CTC imaging. The mice were prepared for SIP-PACT imaging in a similar manner to Ex. 3. The mouse was then secured to a lab-made imaging platform, and the cortical surface was positioned flat and lined up with the transducer array's focal plane. Throughout the experiment, the mouse was maintained under anesthesia with 1.5% vaporized isoflurane. For imaging of the melanoma cancer cells, 100 μL of a cell suspension containing 1×106 B16 cells (also referred to herein as circulating tumor cells or CTCs) was injected into the external carotid artery and/or the common carotid artery provided with a custom-constructed ligature.

Time-series PA images of the mouse cortical vessels were obtained using a system similar to the system described in Ex. 1 and illustrated schematically in FIG. 1A. In these experiments, the mouse was illuminated from above by 680 nm laser pulses with a pulse width of 6 ns and a repetition rate of 10 Hz, delivered to the surface of the skin overlying the mouse cortex at a fluence of 8 mJ/cm$^2$. Without being limited to any particular theory, the 680 nm laser pulse wavelength was selected due to the much stronger optical absorption of the melanin contained within the CTCs at around 680 nm relative to the optical absorption of hemoglobin, as illustrated in the spectrum shown in FIG. 12A.

Figure 5A:
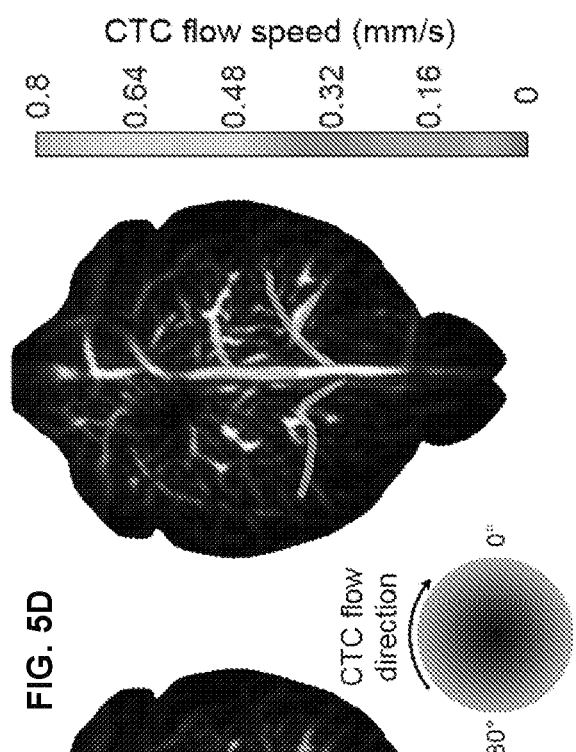
FIG. 5A is a label-free SIP-PACT image obtained using an excitation laser pulse wavelength of 680 nm showing baseline cortical vasculature before the injection of melanoma cancer cells (CTCs)
Figure 5B:
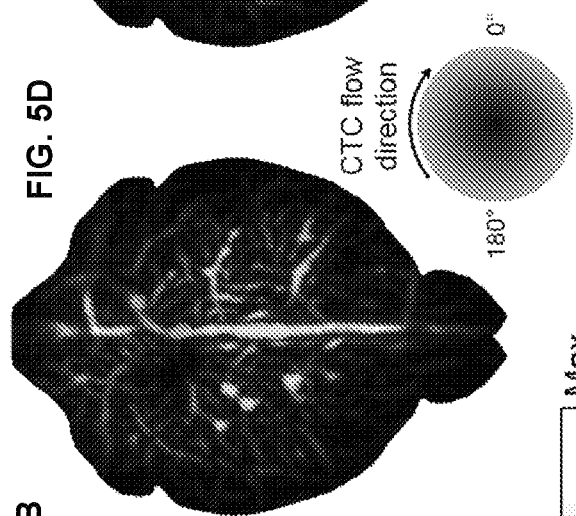
FIG. 5B is a label-free SIP-PACT image obtained using an excitation laser pulse wavelength of 680 nm after injection of CTCs, in which the color map summarizes the various flow directions of injected CTCs.

As a baseline (control), motion-contrast PA images of the cortical vessels of the mouse were obtained before injection of the CTC suspension into the mouse using the motion-contrast method described previously herein in Ex. 2. FIG. 5A is a representative PA motion-contrast image reconstructed using the methods described in Ex. 2 overlaid on an anatomical image of the cortical vessels of the mouse prior to injection of the CTC suspension. After injection of the CTC cell suspension, a time-series of motion-contrast PA images were obtained using the method of Ex. 2. The time-series of motion-contrast PA images were analyzed to obtain local motion vectors from consecutive frames/images using a dense optical flow based algorithm. FIG. 5B is a representative PA motion-contrast image obtained after CTC injection overlaid on the anatomical image of the mouse cortex vessels with the motion of CTC cells represented by colored dots. As depicted in FIG. 5B, the size of each colored dot represents the amplitude of movement and the color represents the direction of movement.

Figure 5D:
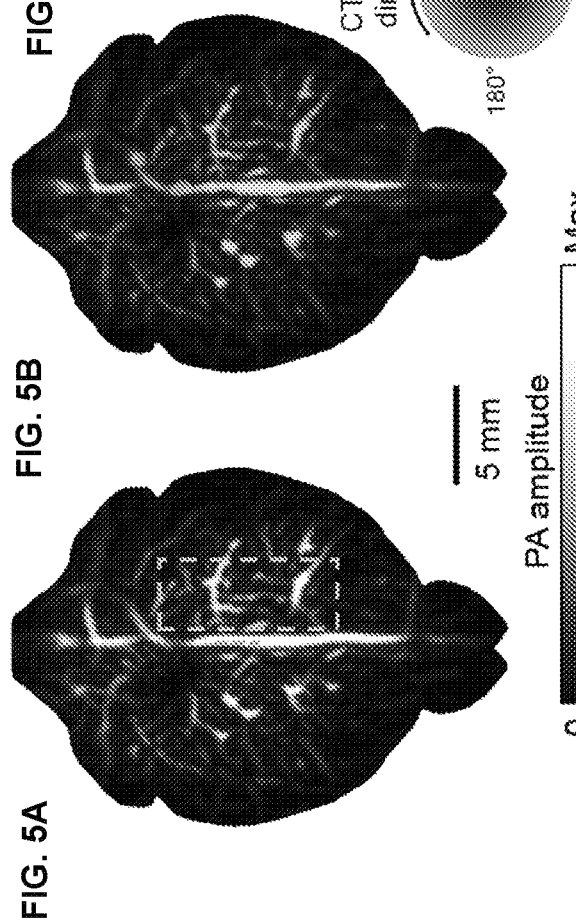
FIG. 5D is a label-free SIP-PACT image obtained using an excitation laser pulse wavelength of 680 nm showing a map of flow speed distribution of the injected CTCs in segmented cortical vessels.
Figure 5C:
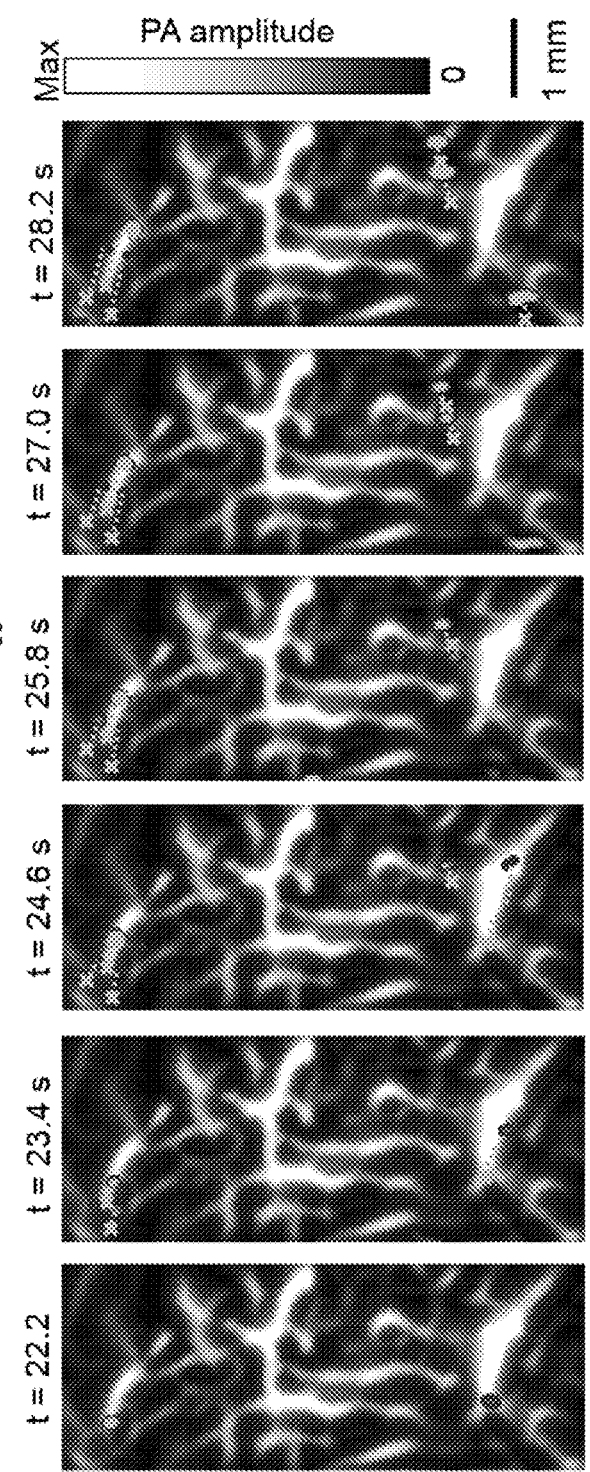
FIG. 5C is a series of label-free SIP-PACT images (i.e. frames) obtained using an excitation laser pulse wavelength of 680 nm at various post-injection times of CTCs tracking the movement of the injected CTCs. Within each frame, crosses mark the initial position of each CTC, circles denote the final position of the CTCs, and the dashed lines denote the movement of the CTCs.

The movements of the injected CTCs within the cortical vessels within the yellow dashed box region overlaid on FIG. 5A were visualized in a series of close-up images shown in FIG. 5C. The CTCs detected in each time frame are highlighted in red, the CTCs detected in the previous frames are shown in yellow, and the flow path of each CTC is marked by an orange dashed line.

In addition, the flow rate of the CTCs (typically less than the cerebral blood flow rate) was calculated by tracking the CTCs in real time and analyzing the movement of the flowing CTCs in the spatiotemporal frequency domain as described below.

Cortical vessels containing flowing CTCs were identified by inspection of videos consisting of the time series of images obtained as described above. A transect was defined along one of the identified cortical veins. This transect is depicted as a red dashed line overlaid on FIG. 5A. Time traces of the PA signal amplitudes measured for each pixel along the cortical transects were extracted and mapped to the space-time domain. FIG. 12B is a map of the extracted PA signal amplitudes in the space-time domain in which the displacement distance along the cortical transect was represented as a horizontal position of each pixel on the map and the elapsed time at which each PA signal at each displacement distance was represented as the vertical position of each pixel on the map. Referring to FIG. 12B, each streak of relatively high normalized PA amplitudes represents a CTC moving along the cortical transect.

A two-dimensional Fourier transformation was performed on the spatiotemporal map of FIG. 12B to obtain a corresponding map of these data in the spatiotemporal frequency domain, shown in FIG. 12C. Referring to FIG. 12C, the pixel position in the horizontal direction corresponds to the frequency signal As illustrated in FIG. 12C, the two-dimensional Fourier transformation mapped lines with the same slope in the space-time domain onto a single line in the spatiotemporal frequency domain, simplifying the calculation of the flow speed and enhancing accuracy. After removing the two DC components and thresholding at 10% of the maximum amplitude, linear fitting was applied to the transformed images to estimate an overall flow speed. As computed from the map shown in FIG. 12C, the flow speed of the injected melanoma cells within the selected cortical vessel was computed by linear fitting to be 0.65 mm/s.

For longer vessel, where a speed distribution was expected, a heuristically determined 1.5-mm sliding window was selected, and the method described above was performed within each window to calculate changes in the CTC flow speed along the cortical vessel. The heuristic tuning of the sliding window size balanced the competing goals of flow speed quantification accuracy and spatial resolution of the CTC flow speed map. Applying this method with the sliding window, the CTC flow speed distributions in multiple cortical vessels of the brain were similarly calculated. FIG. 5D is a map of the calculated CTC flow speeds overlaid onto an anatomical image of the brain.

In another experiment, the flow of injected CTCs in cortical arteries was visualized using the method described above. Time traces of the PA signal amplitudes measured for each pixel along a cortical transect defined along a cortical artery (depicted as a red dashed line overlaid on FIG. 13A) were extracted. FIG. 13B is a map of the extracted PA signal amplitudes in the space-time domain similar to the map shown in FIG. 12B. FIG. 13C is a map of the two-dimensional Fourier transformed signals from the map of FIG. 13B. The flow speed of the CTCs along the cortical transect defined within the cortical artery was calculated to be 10.0 mm/s using the method described above.

Figures 14A, 14B, 14C:
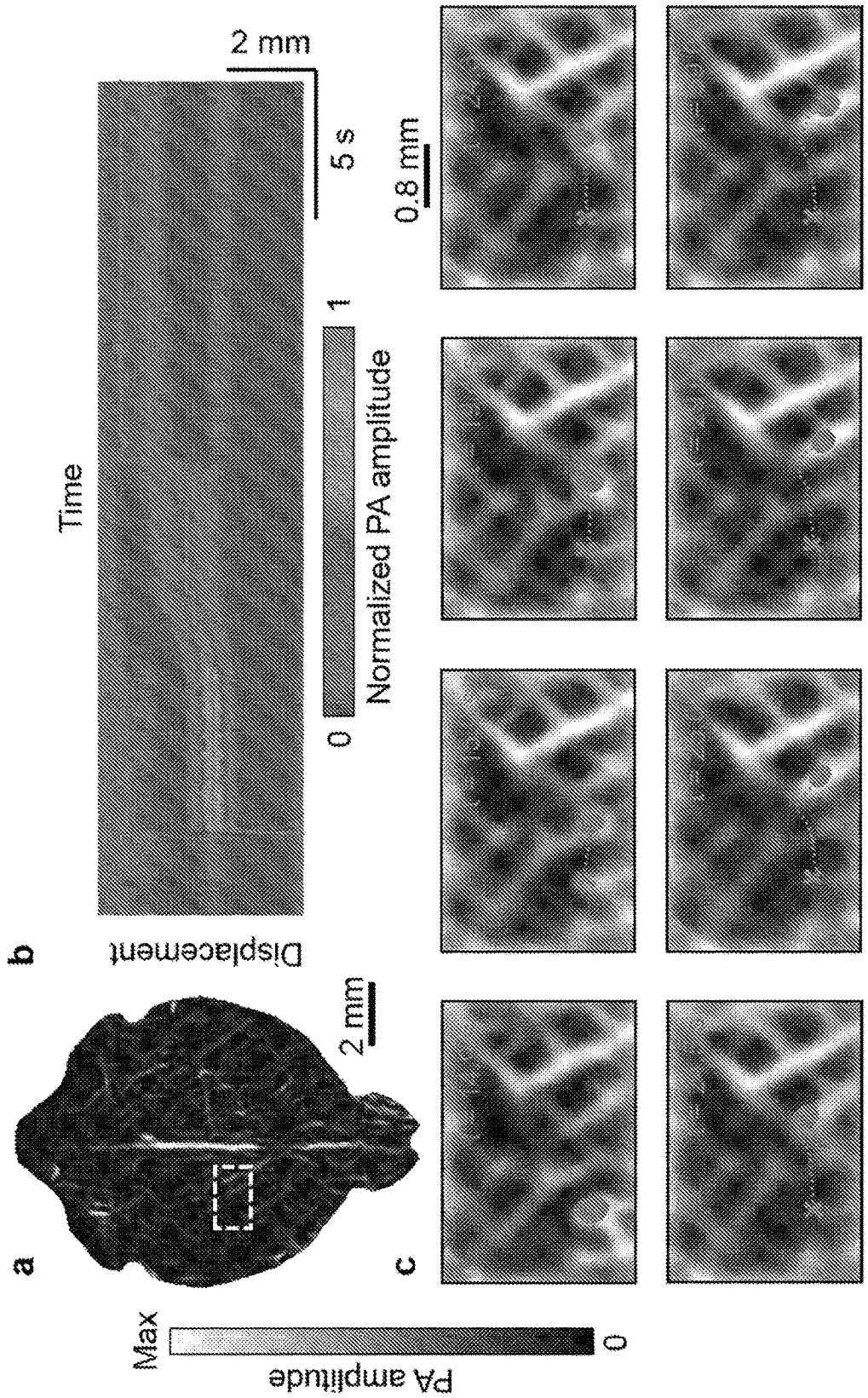
FIG. 14A is a label-free SIP-PACT image of a mouse brain cortex after cessation of movement of the injected CTCs.
FIG. 14B is a map of PA signal amplitude for each pixel along a trajectory denoted as dashed lines in FIG. 14C as a function of time; the line in FIG. 14B denotes the trajectory of the center position of a group of CTCs prior to cessation of movement. The plateau of the line in FIG. 14B represents the trajectory and time at which the group of CTCs ceased movement.
FIG. 14C contains a series of images showing enlargements of the label-free SIP-PACT image of FIG. 14A within a region denoted by a white dashed box in FIG. 14A; the images of FIG. 14C were obtained over a range of times after injection of CTCs. Within each image of FIG. 14C, overlaid crosses denote an initial center position of a tracked CTC, each overlaid dot denote the central position of the tracked CTC in each image, and each dashed line denotes a trajectory of a tracked CTC.

FIG. 14A is another representative PA motion-contrast image reconstructed using the methods described in Ex. 2. After injection of the CTC cell suspension, a time-series of motion-contrast PA images were obtained using the method of Ex. 2. FIG. 14B is a map of the PA amplitudes as a function of displacement along a cortical vessel (displacement, vertical axis) and time (horizontal axis). Referring again to FIG. 14B, the overlaid red line tracks the trajectory of a center position of non-moving CTCs, and the horizontal plateau of the red line represents where and when the CTCs ceased moving within the cortical vessel. The time-series of motion-contrast PA images were analyzed to obtain local motion vectors, and the movements of the injected CTCs within the cortical vessels within the dashed box region overlaid on FIG. 14A were visualized in a series of close-up images shown in FIG. 14C. The CTCs detected in each time frame shown in FIG. 14C were highlighted in red, the CTCs detected in the previous frames were shown in yellow, and the flow path of each CTC was marked by an orange dashed line. As illustrated in FIG. 14C, the position of the overlaid red dot representing a CTC was unchanged at imaging times of 25 seconds or later, indicating that the motion of the CTC was arrested within the cortical vessel.

These experiments demonstrated the ability of the SIP-PACT system to perform metastasis imaging by tracking circulating CTCs and observing the CTCs becoming trapped in cortical vessels in vivo within a mouse brain non-invasively. This capability can provide new insights into the extravasation and homing of metastasizing cells, and can address unanswered questions in metastasis research. This knowledge can potentially be used to enhance the design of tailored cancer therapies.

Example 5: EIR Response of SIP-PACT System

To assess the electrical impulse response (EIR) of the SIP-PACT system described herein, the following experiments were conducted.

A point PA source was positioned at the center of the ring ultrasound transducer array of the SIP-PACT system as described in Ex. 1 and illustrated in FIG. 1A. The point source was created by depositing red epoxy on the tip of a single mode optic fiber. The deposited epoxy measured about 30 μm×30 μm×50 μm, and was small enough to be regarded as a spatial point source for the SIP-PACT system. After the fiber tip was positioned in the acoustic focal plane of the transducer array and the center of the ring, an excitation laser pulse with a pulse width of one nanosecond was fired through the single mode fiber and raw PA signals were recorded by each transducer in the 512-element array.

Figures 6A, 6B:
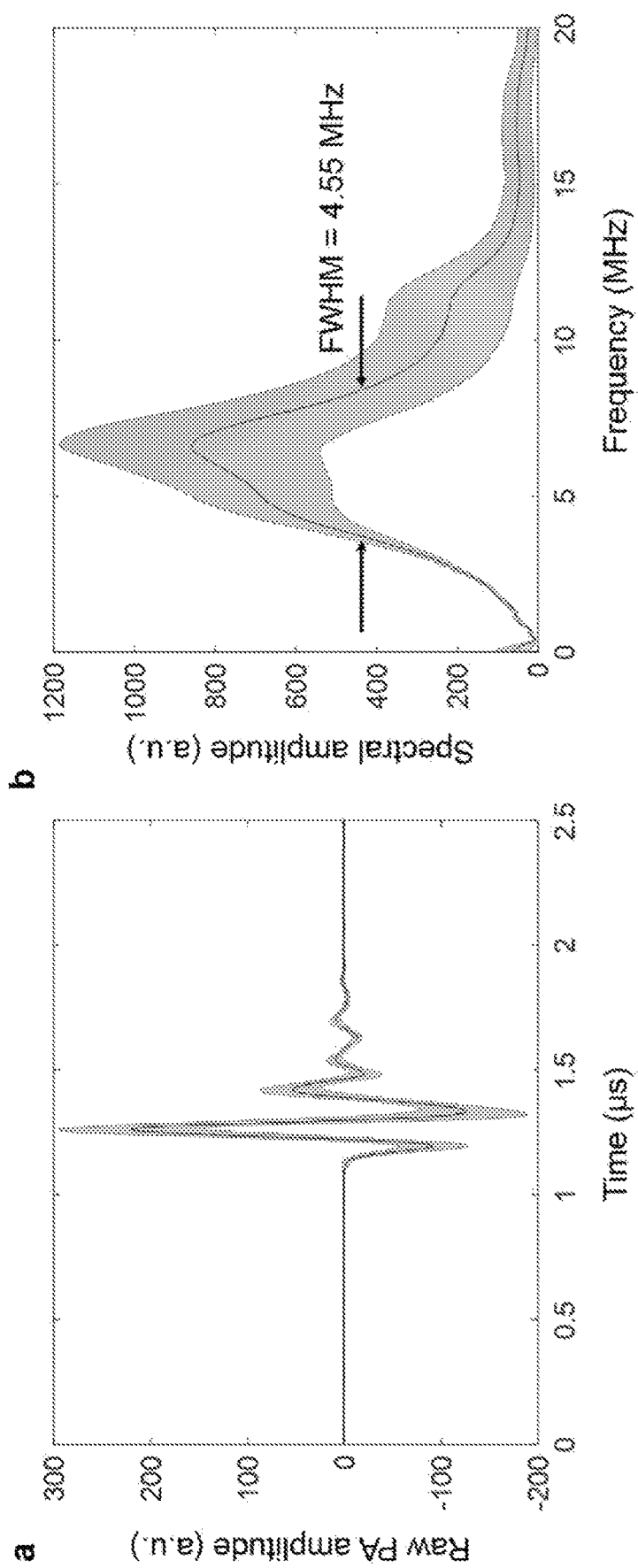
FIG. 6A is a graph showing raw frequency (RF) PA measurements obtained from individual ultrasonic transducer elements in a ring array, in which the PA source was a point PA source positioned at the center of the transducer ring array. Black solid line denotes the mean value of all transducer element responses, and the gray region delineates the standard deviation of all RF PA measurements.
FIG. 6B is a graph showing the frequency spectrum of the RF signals summarized in FIG. 6A, showing a transducer array bandwidth of about 4.55 MHz. Black line denotes the mean values of the spectral amplitude averaged over all measured RF signals, and the gray region represents the standard deviation of all measured RF signals across the elements of the ring transducer array.

FIG. 6A is a graph summarizing the raw radio frequency (RF) signals detected by each ultrasonic transducer element of the ring array as produced by the point PA source at the center of the ring. The black solid line of FIG. 6A represents the mean value of all transducer elements' responses, and the gray region represents the standard deviation across all elements. FIG. 6B is a frequency spectrum summarizing the Fourier transform amplitude of each RF signal summarized in FIG. 6A, in which the black solid line represents the mean value of the spectral amplitude of all RF signals, and the gray region represents the standard deviation across the elements. Referring again to FIG. 6B, the bandwidth of the transducer array was determined to be about 4.55 MHz based on the frequency spectrum.

Example 6: In-Plane and Elevational Resolution of SIP-PACT System

To assess the in-plane and elevational resolution of the photoacoustic computed tomographic (PACT) images obtained using the SIP-PACT system and methods described herein, the following experiments were conducted.

Figures 7A, 7B, 7C:
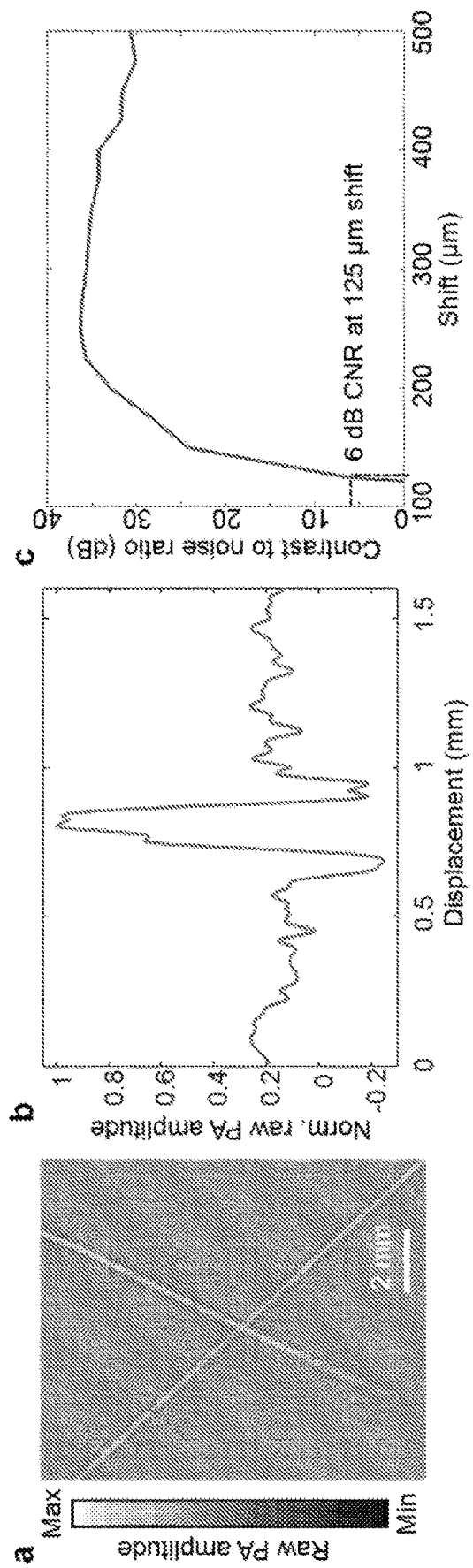
FIG. 7A is a SIP-PACT image of two crossed tungsten wires, each with a nominal diameter of 50 µm.
FIG. 7B is a graph of the photoacoustic amplitude distribution along a transect denoted by a dash-dot line in FIG. 7A.
FIG. 7C is a graph of the contrast-to-noise ratio (CNR) versus a shift distance, in which each CNR was determined using the sum of the baseline PA signal profile shown in FIG. 7B and a PA signal shifted by each shift distance.

To quantify the in-plane resolution of the SIP-PACT system, two crossed tungsten wires, each with a nominal diameter of 50 μm were positioned within the SIP-PACT system described in Ex. 1 and illustrated in FIG. 1A. The SIP-PACT system was used as described herein to obtain a PA image of the crossed tungsten wires, shown in FIG. 7A. PA signals from the PA image were extracted from the PA image along a transect defined perpendicular to one of the tungsten wires and represented by the red dashed line overlaid on the PA image of FIG. 7A. FIG. 7C is a graph of the contrast-to-noise ratio (CNR) versus the shift in the sum of the original line profile shown in (b) and the shifted one. The in-plane resolution, defined as the shift corresponding to 6 dB CNR, is 125 μm.

Based on the PA amplitude data summarized in FIG. 7C, contrast-to-noise ratios (CNRs) were calculated over a range of shift distances, where each CNR was determined using the sum of the baseline PA signal profile shown in FIG. 7B and a PA signal shifted by a shift distance. FIG. 7C is a graph of the contrast-to-noise ratios (CNR) plotted against the corresponding shift distances. Based on the data from FIG. 7C, the in-plane resolution, defined as the shift corresponding to 6 dB CNR, was determined to be about 125 rm.

Figures 8A, 8B, 8C, 8D:
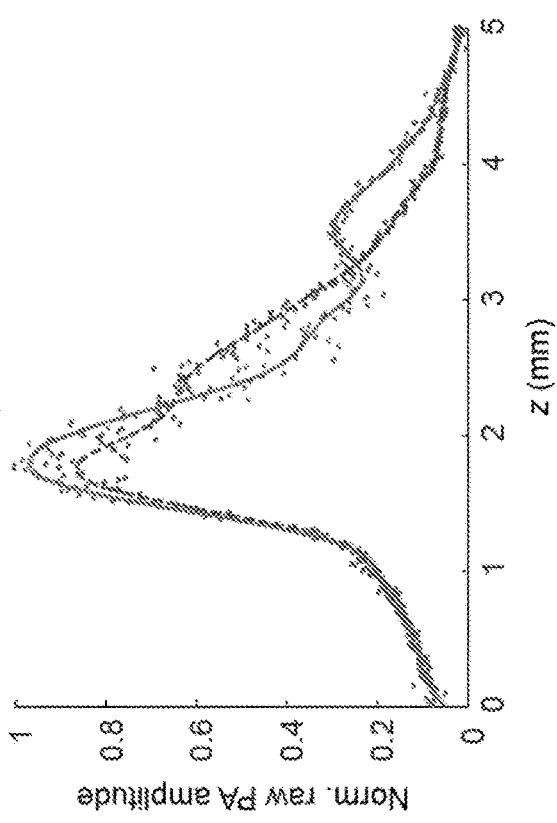
FIG. 8A is a photoacoustic image of a simulated acoustic focus field projected onto the x-z plane.
FIG. 8B is a photoacoustic image of a tungsten wire with a nominal diameter of 50 µm, projected onto the x-z plane.
FIG. 8C is a graph of PA amplitude as a function of distance from the center of focus of the ring transducer array showing simulated profiles of FIG. 8A along a z-transect positioned at the center of the ring transducer array (indicated in FIG. 8A by the solid white arrow) and along a z-transect positioned at a 6.5 mm offset from the center of the ring transducer array (indicated in FIG. 8A by the dashed white arrow)
FIG. 8D is graph of PA amplitude as a function of distance from the center of focus of the ring transducer array showing the simulated profiles of FIG. 8B along a z-transect positioned at the center of the ring (indicated in FIG. 8B by a solid white arrow) and along a z-transect positioned at a 6.5 mm offset from the center of the ring transducer array (indicated in FIG. 8B by a dashed white arrow)

To assess the elevational resolution of the ring transducer array of the SIP-PACT system described in Ex. 1 and illustrated in FIG. 1A, a simulation was performed to estimate the acoustic focus field of the ring array. FIG. 8A is a map of a simulated acoustic focus field projected in the x-z plane (see coordinate axis inset of FIG. 1A). FIG. 8C is a profile of the normalized PA signal extracted from the simulated acoustic field obtained along a first linear transect at the center of the ring array as indicated by a solid white line on FIG. 8A and along a second linear transect positioned 6.5 mm from the center of the ring array as indicated by a dashed white line overlaid on FIG. 8A. Referring to FIG. 8B, the full width at half maximum (FHHM) for the profile at the ring center was 0.85 mm, and the FWHM for the profile positioned 6.5 mm off-center within the ring array was 1.34 mm. FIG. 8B is a photoacoustic image of a tungsten wire with a nominal diameter of 50 μm obtained using the SIP-PACT system as described above and projected on the x-z plane. FIG. 8D is a profile of the normalized PA signal extracted from the PA image of FIG. 8B along a first linear transect at the center of the ring array (solid white line) and along a second linear transect positioned 6.5 mm from the center of the ring array (dashed white line). Referring to FIG. 8D, the full width at half maximum (FHHM) for the profile at the ring center was 1.05 mm, and the FWHM for the profile positioned 6.5 mm off-center within the ring array was 1.51 mm, which were consistent with the FWHM values estimated from the simulated acoustic field of FIG. 8A.

Example 7: Effect of Dual-Speed UBP Reconstruction Method on Image Quality

To assess the effect of the dual-speed UPB reconstruction method on image quality of PACT images obtained using the SIP-PACT system and methods described herein, the following experiments were conducted.

The k-Wave toolbox was used in MATLAB (MathWorks, Natick, Mass., USA) to develop a 2D simulation of the SIP-PACT system with the circular ultrasound transducer array. The simulation is illustrated schematically in FIG. 9A. As shown in FIG. 9A, the simulation included a circular numerical phantom with a radius of 13 mm and a uniform speed of sound ($c_{tissue}$) of 1520 m/s. The phantom was surrounded by water with a uniform speed of sound ($c_{water}$) of 1480 m/s, and the entire region containing the water was bounded by a ring-shaped detector array with a radius of 52 mm. The phantom and the ring array were located concentrically with the phantom centered within the ring array. Within the simulated phantom, an optical absorption pattern representing a leaf skeleton was used, shown illustrated in FIG. 9B.

The k-Wave toolbox was again used to generate simulated PA data, and the simulated PA data was reconstructed into PA images according to each of two algorithms. A universal back-projection (UBP) reconstruction algorithm assuming a single speed of sound (SOS) set at a value intermediate between $c_{tissue}$ and $c_{water}$ was used to reconstruct a single-SOS PA image, shown in FIG. 9C. A UBP reconstruction algorithm assuming a dual speed of sound, described herein above, was used to reconstruct a dual-SOS PA image, shown in FIG. 9D. Comparing the single-SOS and dual-SOS PA images of FIGS. 9C and 9D, respectively, the dual speed of sound PA reconstruction algorithm reduces splitting or fringing artifacts in the image.

Another 2D simulation of a phantom within a SIP-PACT system with a ring transducer array was developed to assess the in localization error in PA images due to the use of the single SOS reconstruction algorithm described herein above. FIG. 10A is a schematic illustration of the simulation, which included a circular phantom with a 10 mm radius ($R_x=R_y=10$ mm) and a uniform SOS ($v_1=1570$ m/s) centered within a ring transducer array with a ring radius of $R_d=52$ mm centered at a simulation origin (x=y=0). The phantom was surrounded within the ring array by water with a uniform SOS ($v_2=1506$ m/s) and was offset from the center of the ring array by an arbitrary offset distance ($x_0, y_0$). A single PA source was positioned within the simulated phantom at an arbitrary position ($x_s, y_s$).

The simulated PA signal generated by a point source, located at the position ($x_s, y_s$) within the phantom and received by each simulated ultrasound detector positioned at ($x_d, y_d$) was back-projected assuming a single SOS intermediate between $v_1$ and $v_2$. FIG. 9B is a summary of the back-projected positions of the simulated PA signal as received by each detector positioned at a corresponding azimuthal angle. The true position of the PA source is indicated by a red star overlaid on the graph of FIG. 9B and each back-projected position based on the PA signal as received by each detector positioned at each azimuthal angle of the ring array is color-coded to indicate the corresponding azimuthal angle of the detector used for the reconstructed position. As illustrated in FIG. 9B the reconstructed position of the point source, according to the single-SOS assumption, scatters around the correct position, depending on the azimuthal angle of the transducer, with a difference of as much as about 0.4 mm in position observed among all detectors of the ring array.

Measurements of PA signals from a mouse liver were obtained using the SIP-PACT system and methods described in Ex. 1. Single-SOS and dual-SOS PA images of the mouse liver were reconstructed using the PA signals in the universal back-projection algorithm assuming a single intermediate speed of sound and assuming two speeds of sound respectively, as described herein previously. A comparison of the single-SOS PA image (FIG. 10C) and the dual-SOS PA image (FIG. 10D) revealed many artifacts, including horseshoe-shaped features on the body surface (for example the blood vessels perpendicular to the plane of the PA image and distributed around the perimeter of the image, as well as splitting of the vasculature in the upper-left and lower-right regions of the body that appear in the single SOS PA image of FIG. 10C. These artifacts were significantly reduced in the corresponding dual-SOS PA image of FIG. 10D.

The results of this experiment demonstrated that gross localization errors are introduced by the assumption of a single SOS in the universal back-projection reconstruction algorithm used to reconstruct PA images from detected PA signals. In PA images reconstructed using a single-SOS assumption, these gross localization errors are manifested by image artifacts such as horseshoe-shaped features. These image artifacts are greatly reduced using the UPB reconstruction algorithm assuming dual SOS.

Example 8: 2D Time-Resolved Imaging of Dye Perfusion Using SIP-PACT System

To demonstrate 2D time-resolved imaging of dye perfusion using the SIP-PACT system and methods described herein, the following experiments were conducted.

Adult, 3-4-month-old Swiss Webster mice (Hsd: ND4, Swiss Webster, Harlan Co.; 20-30 g body weight) were prepared for imaging using the SIP-PACT system in a manner similar to Ex. 4. For dye perfusion imaging, 100 µL of NIR dye (FHI 104422P, Fabricolor Holding Int'l LLC) solution with a 0.5% mass concentration was injected into the external carotid artery and/or the common carotid artery provided with a custom-constructed ligature prior to imaging as described previously in Ex. 4.

Time-series PA images of the mouse cortical vessels were obtained using a SIP-PACT system similar to the system described in Ex. 1 and illustrated schematically in FIG. 1A. In these experiments, the mouse was illuminated from above by 1064 nm laser pulses at a repetition rate of 50 Hz, delivered to the surface of the skin overlying the mouse cortex at a fluence of about 50 mJ/cm$^2$. As a baseline (control), motion-contrast PA images of the cortical vessels of the mouse were obtained before injection of the NIR dye into the mouse using the motion-contrast method described previously herein in Ex. 2.

FIG. 15A is a time series of representative PA images corresponding to different post-injection times. The perfusion of the NIR dye was quantified as normalized differential PA signal amplitudes (PA signal at each post-injection time minus a pre-injection PA signal). The map of normalized differential PA signal amplitudes for each post-injection time are superimposed over a normalized PA amplitude image obtained prior to injection of the NIR dye. Referring to FIG. 15A, the injected NIR dye was observed moving up a central vessel and into vessels of decreasing size. FIG. 15B is a graph of the total PA signal received by all detectors in the ring transducer array as a function of post-injection time. FIG. 15B exhibits an increase in total PA signal post-injection to a relatively constant signal magnitude at about 20 seconds post-injection.

Whole-body perfusion of the NIR dye after arterial injection was assessed using a SIP-PAT system similar to the system illustrated in FIG. 1B. For the whole-body functional imaging, each whole mouse body was illuminated from the sides with laser pulses of 1064 nm delivered at a repetition rate of 50 Hz and a fluence at the skin surface of about 50 mJ/cm$^2$ as described previously. Whole-body perfusion dynamics were imaged using the SIP-PACT system by eliciting PA signals from the mouse body at various transverse planes through the thoracic and abdominal cavities of the mouse in response to illumination by the laser pulses.

Figure 16:
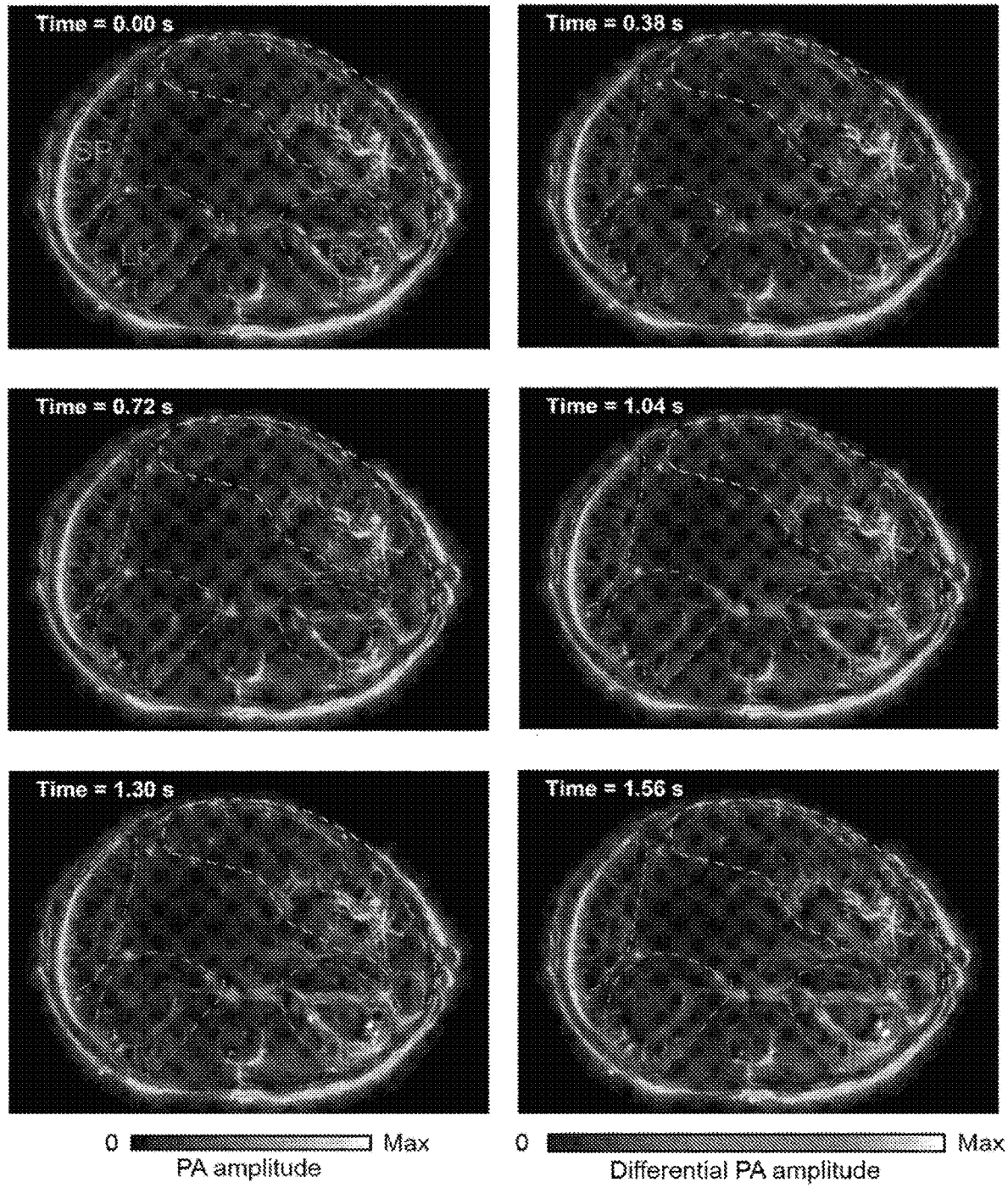
FIG. 16 contains a series of cross-sectional SIP-PACT images through a lower abdominal cavity at different times after injection of a PA contrast agent to provide a visualization of whole-body dye perfusion.

FIG. 16 is a time series of representative PA images corresponding to different post-injection times.

Example 9: Deep Imaging of Whole Rat Brain Using SIP-PACT System

To demonstrate whole-brain imaging using the SIP-PACT system as described above in one aspect, the following experiments were conducted.

Adult, two- to three-month-old Sprague Dawley rats (Hsd:Sprague Dawley SD, Harlan Co.; 170-200 g body weight) were used for the in vivo whole rat brain imaging. Before the whole-brain imaging experiments, a craniotomy was performed on the rat to form a cranial window to maximize acoustic transmission. Under isoflurane anesthesia, the rat was placed in a stereotaxic apparatus. After being shaved and swabbed, the scalp was incised and retracted. The parietal bone was removed using a fine drill bit, with frequent irrigation and swabbing with cold, sterile phosphate-buffered saline. A bone flap was removed over an area of approximately 0.5 cm×0.9 cm to expose the parietal lobes of the rat's brain. The cortical surface was positioned flat and lined up with the transducer array's focal plane.

Figure 19:
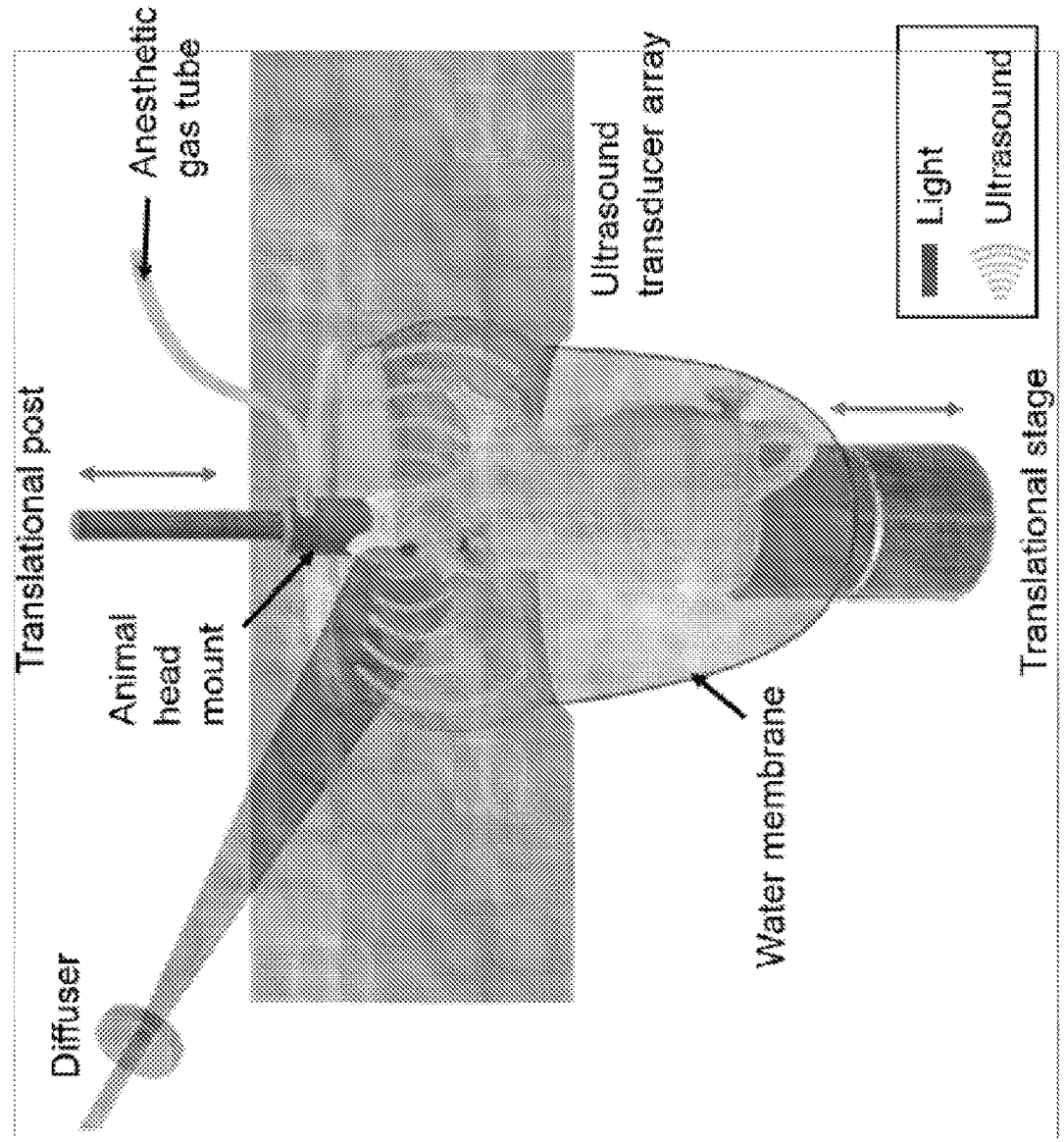
FIG. 19 is a schematic illustration of a SIP-PACT system for animal brain imaging according to one aspect of the disclosure.

The rat's head was mounted vertically within a SIP-PACT system and the light pulses were obliquely directed onto the rat cortex, as illustrated schematically in FIG. 19. After locating the proper imaging plane to obtain a coronal view of the rat's brain, the isoflurane level delivered to the mouse was changed to 0.5% from 1.5%. After about forty minutes, the measurement of functional connectivity was initiated. Each functional connectivity measurement was obtained in about ten minutes, with a 2 Hz frame rate and light pulses 1,064 nm illumination.

Figure 20:
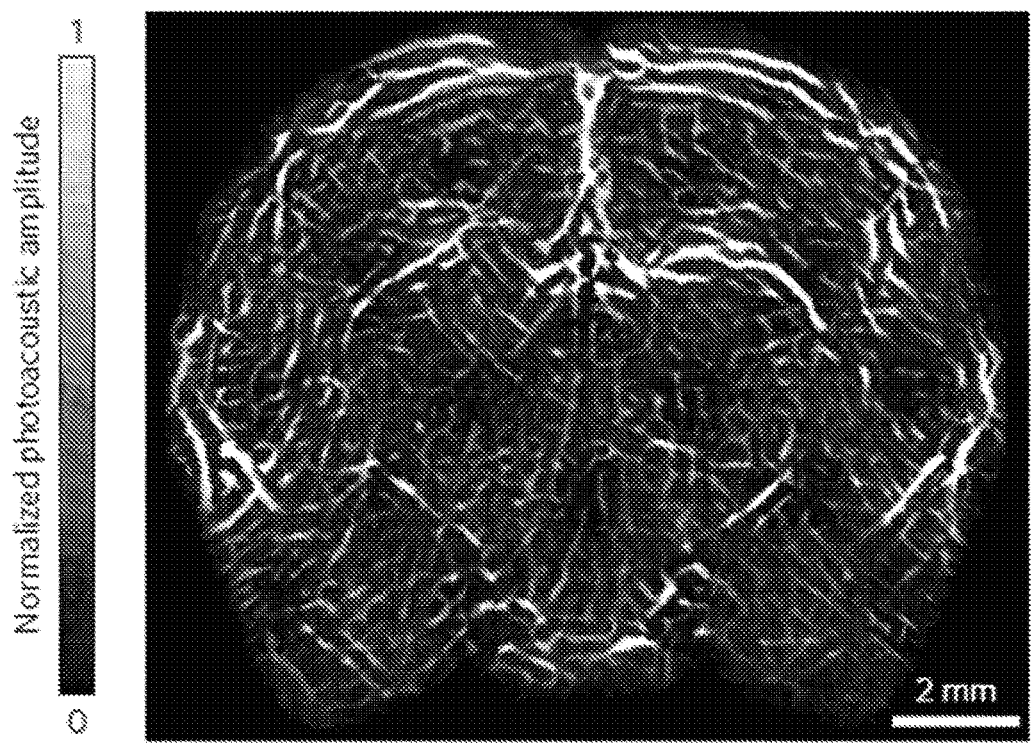
FIG. 20 is an image showing a vasculature of a whole-brain of a rat in the coronal plane obtained using a SIP-PACT system according to one aspect of the disclosure.

Taking advantage of the deep penetration of 1,064 nm wavelength light, full-view acoustic transducer coverage and high detection sensitivity of SIP-PACT, a coronal view of the rat whole brain at depths of up to about 11 mm was produced with detailed vasculature imaging, as illustrated in FIG. 20.

Existing systems and methods, such as resting state fMRI, measure intrinsic functional connectivity across spatially separated brain regions using regionally correlated, spontaneous, low-frequency (0.01-0.1 Hz) fluctuations in BOLD signals, particularly during resting state and task-free periods. In a manner similar to fMRI, SIP-PACT also globally monitors the hemodynamics of the brain with sufficient spatiotemporal resolution and penetration. To measure functional connectivity of the rat's brain, the spontaneous hemodynamic responses between contralateral regions of the rat's brain were measured and compared.

Figure 21:
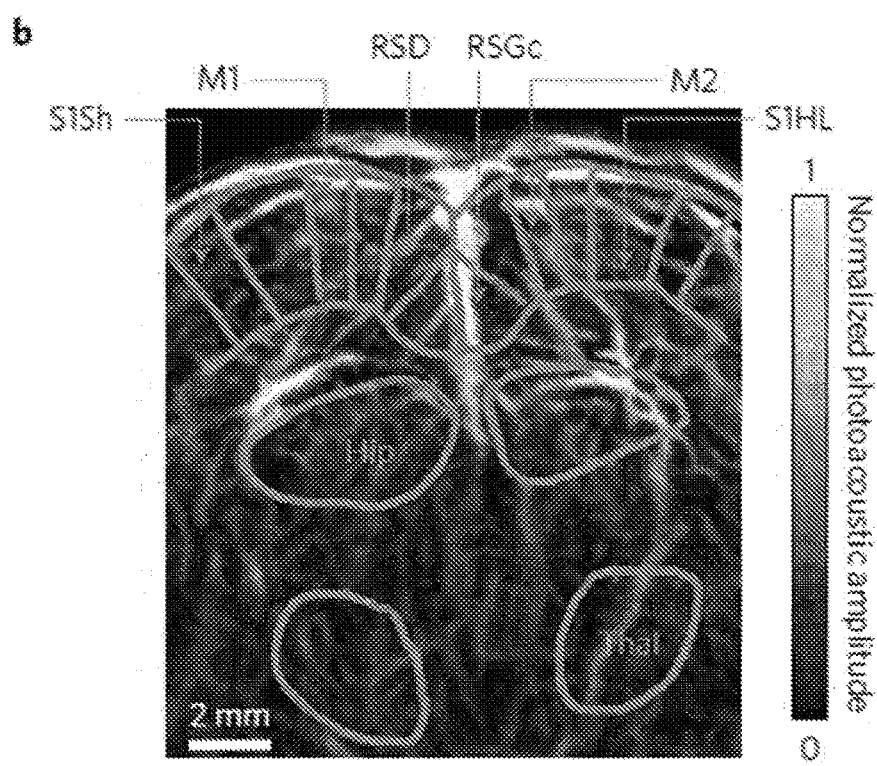
FIG. 21 is an image showing segmentations of different functional regions of the brain of the rat shown in FIG. 20.

To measure functional connectivity using the SIP-PACT system, the whole-brain images were initially filtered using a 5 pixel disk filter to reduce motion noises due to respiration. A region of interest (ROI) in the visible brain area was then identified manually, and a second-order Butterworth bandpass filter (0.01 Hz to 0.1 Hz) was subsequently applied to all temporal PA signal sequences. The measured functional connectivity of the rat's whole brain in the coronal plane (~bregma—2.16 mm) included 16 functional regions, shown labelled in FIG. 21.

Figure 22:
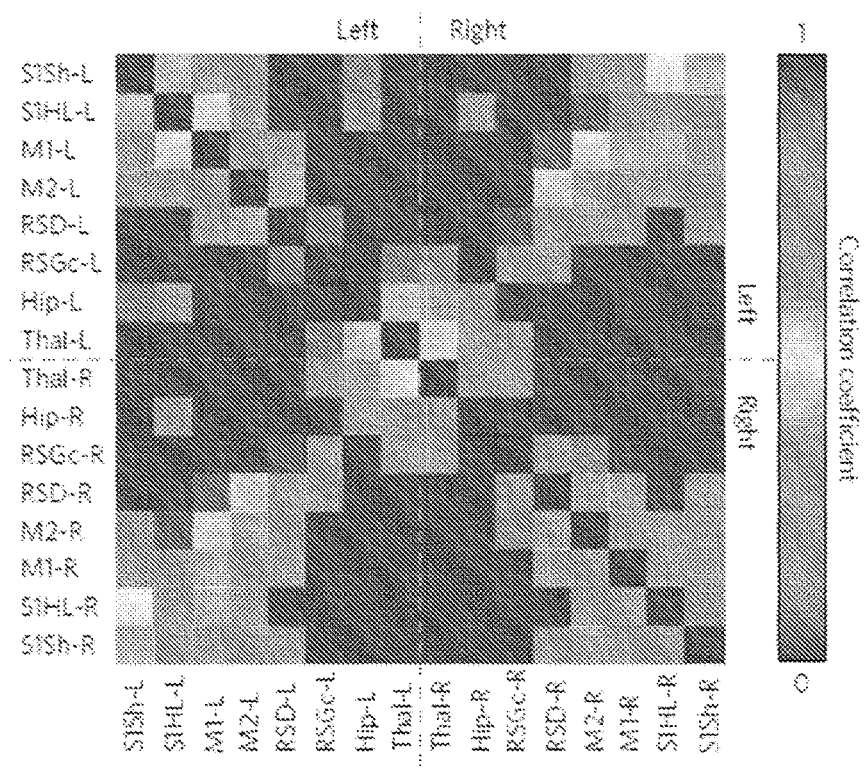
FIG. 22 is an image showing a correlation matrix of the 16 functional regions shown labeled in FIG. 21; Hip, hippocampus; IN, intestine; LK, left kidney; LLV, left liver; M1, primary motor cortex; M2, secondary motor cortex; RK, right kidney; RLV, right liver; RSD, retrosplenial dysgranular cortex; RSGc, retrosplenial granular cortex; S1Sh, primary somatosensory-shoulder region; S1HL, primary somatosensory cortex-hindlimb region; SC, spinal cord; SP, spleen; SV, splenic vein; and Thal, thalamus.

A global signal regression was performed on the time sequences within the ROI, and a functional region-based functional connectivity analysis was performed by identifying the functional regions, averaging the signals from pixels within each functional region, and computing correlation coefficients between each pair of functional regions to form the connectivity network image. FIG. 22 is a map of the correlation coefficients obtained from the global signal regression showing clear correlation between the left and right hemispheres, as well as the correlation between neighboring regions in the neocortex. In addition, a left-right correlation was identified between the deep thalamus regions at a depth of 9.7 mm.

Figure 23:
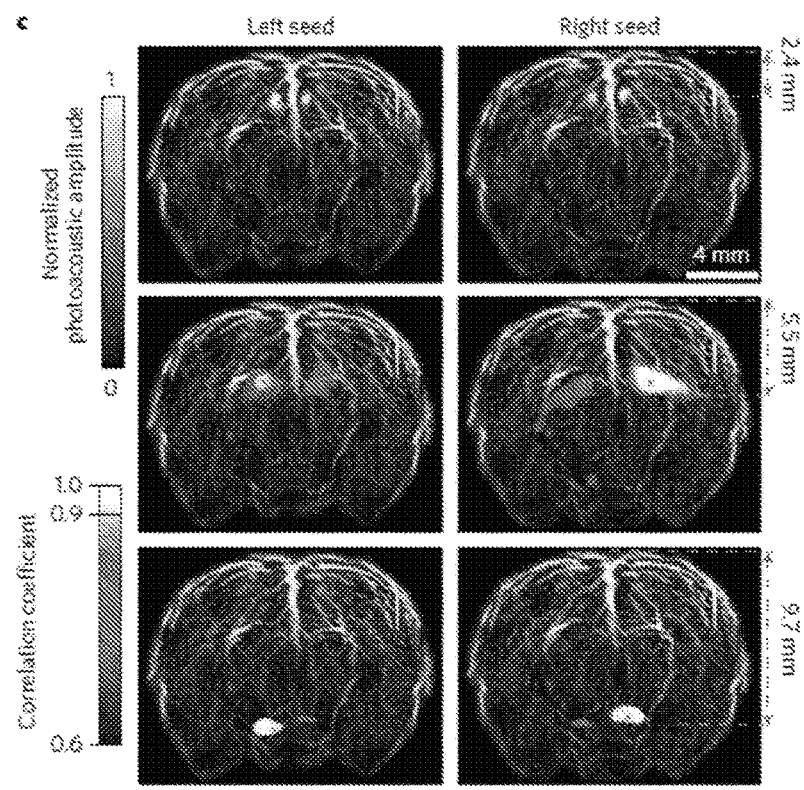
FIG. 23 is a series of brain images showing the results of a seed-based functional connectivity analyses of the RSGc region (top row), the hippocampus region (middle row) and the thalamus region (bottom row) on both sides of the brain.

A seed-based functional connectivity analysis was also performed by selecting a seed within the brain in the image and computed the correlation coefficients between all pixels in the ROI and the seed. Seed-based connectivity maps are shown in FIG. 23 for the RSGc region (top row), the hippocampus region (middle row) and the thalamus region (bottom row) on both sides of the brain.

The results of this experiment demonstrated the capability of the SIP-PACT system to perform high-resolution imaging suitable for studying deep brain functions at depths that were previously challenging to image using existing optical contrast methods.

Example 10: Detection Sensitivity of SIP-PACT

To assess the detection sensitivity of the SIP-PACT system as described above, the following experiments were conducted.

The noise-equivalent molar concentration (NEC) of hemoglobin was used for the quantification of detection sensitivity. For a fair comparison, the incident fluence of SIP-PACT is scaled to the American National Standards Institute (ANSI) safety limit for the skin at 1064 nm (100 $mJ/cm^2$ at the skin surface at a 10-Hz repetition rate) of the dual-speed UPB reconstruction.

Figure 27:
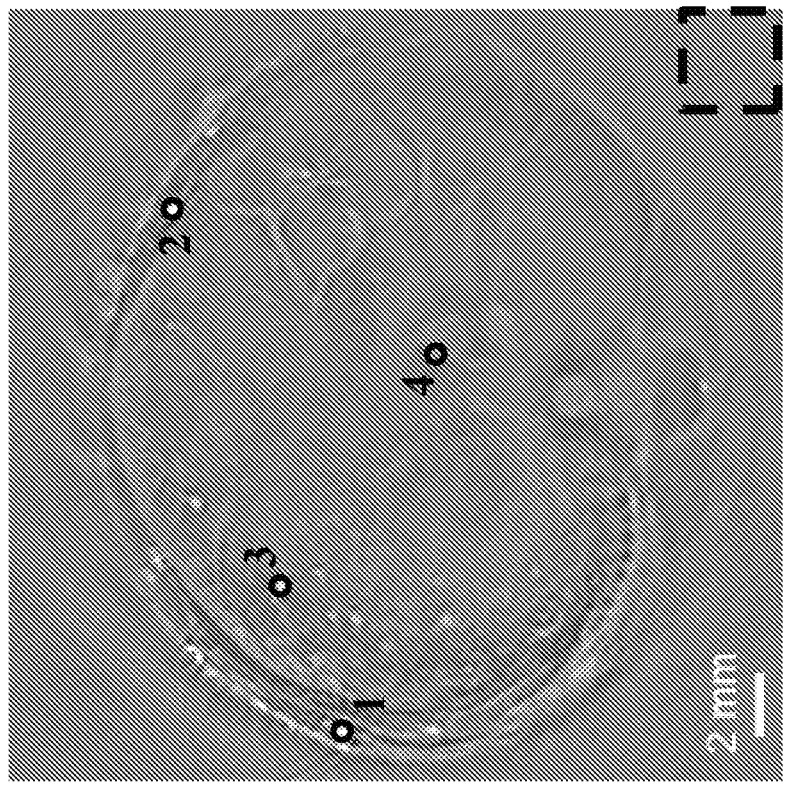
FIG. 27 is an image showing a cross-sectional image of an upper abdominal cavity, with circles overlaid to label those blood vessels within the image selected for signal amplitude quantification and a dashed square overlaid to label the region of the image selected for noise level quantification.

Four vessels within a cross-sectional image of the upper abdominal cavity (see circles in FIG. 27) were selected for signal amplitude quantification. A region of the image outside of the upper abdominal cavity within the water tank of the SIP-PACT system (see dashed square in FIG. 27) was selected for noise level quantification. NEC was calculated using standard methods.

Figure 28:
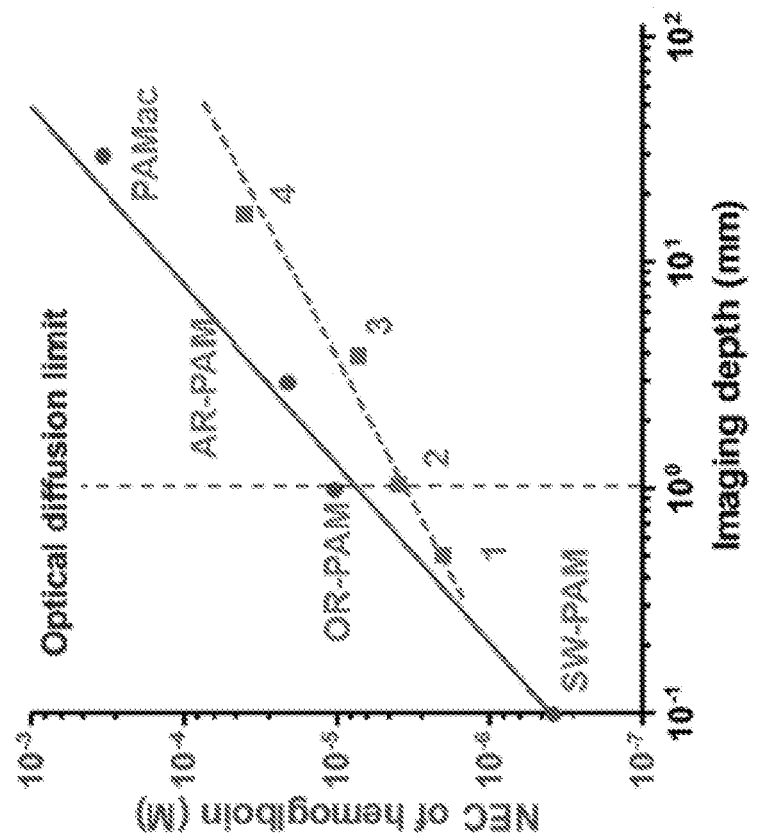
FIG. 28 is a graph comparing the calculated detection sensitivity (NEC of hemoglobin) of a SIP-PACT system to previously reported sensitivity values.

FIG. 28 is a graph showing the calculated NEC for the SIP-PACT system compared to previously reported sensitivity values say various imaging depths. The dots of FIG. 28 are previously reported NEC values and the solid line is the fit of the reported NEC values. The squares of FIG. 28 are the NEC values quantified from the vessels in the image of FIG. 27, and the dashed line is the fit of the SIP-PACT derived NEC values. As illustrated by the graph of FIG. 28, the SIP-PACT-derived NEC values were consistently lower than the previously reported NEC values derived from various other optical imaging technologies, indicating a higher sensitivity for the SIP-PACT system.

Example 11: Image Quality of SIP-PACT

To assess the image quality of the SIP-PACT system as described above, the following experiments were conducted.

Figures 29, 30, 31:
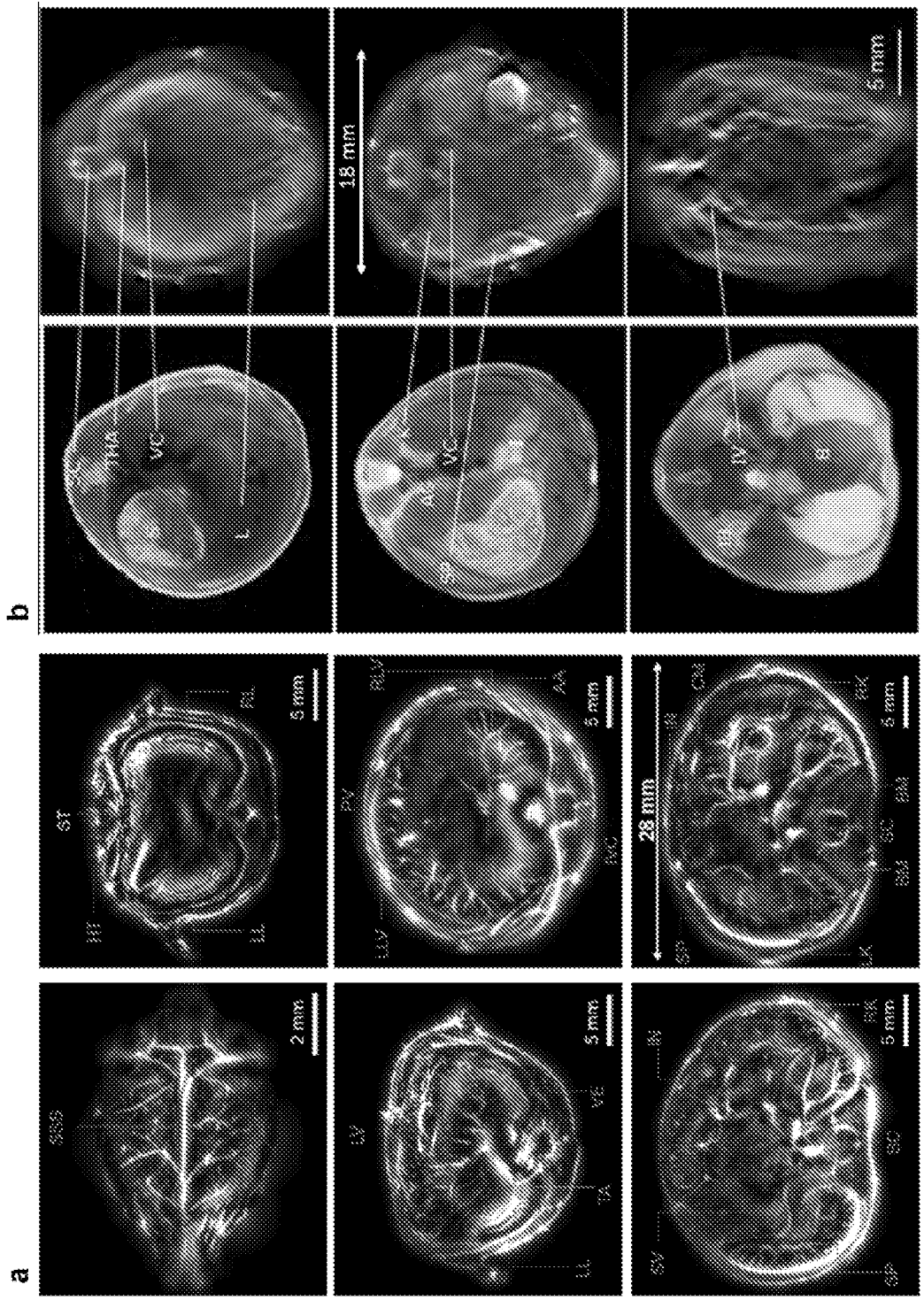
FIG. 29 is a series of cross-sectional images of mouse whole-body anatomy, from brain to lower abdominal cavity, acquired by SIP-PACT according to one aspect of the disclosure: AA, abdominal aorta; BM, backbone muscles; CM, cecum; HT, heart; IN, intestines; IVC, inferior vena cava; LK, left kidney; LL, left lung; LLV, left lobe of liver; LV, liver; PV, portal vein; RK, right kidney; RL, right lung; RLV, right lobe of liver; SC, spinal cord; SP, spleen; SSS, superior sagittal sinus; ST, sternum; SV, splenic vein; TA, thoracic aorta; VE, vertebra.
FIG. 30 is a series of reference macroscopic RGB pictures of cross sections of a frozen mouse taken from approximately the corresponding positions of the images of FIG. 31: AG, adrenal gland; B, bladder; I, intestines; IB, iliac body; IV, iliac vein; K, kidney; L, liver; P, pancreas; S, stomach; SC, spinal cord; SP, spleen; THA, thoracic aorta; VC, vena cava.
FIG. 31 is a series of cross-sectional images acquired by an existing PACT system, commercially available from iThera Medical GmbH.

Whole-body images obtained using SIP-PACT (see FIG. 29) were compared to corresponding images obtained using a state-of-the-art small animal PACT imaging system (see FIG. 31) as well as reference macroscopic RGB images of frozen mouse cross-sections. The SIP-PACT images of FIG. 29 showed detailed structures and vasculatures of internal organs, while state-of-the-art PACT images of FIG. 31 barely differentiated the internal organs due to low image contrast. The image quality of SIP-PACT is considerably higher than that of the state-of-the-art PACT imaging system.

Example 12: Effect of Data Multiplexing on Image Quality of SIP-PACT

To assess the effect of multiplexing on imaging quality of the SIP-PACT system as described above, the following experiments were conducted.

Figure 32:
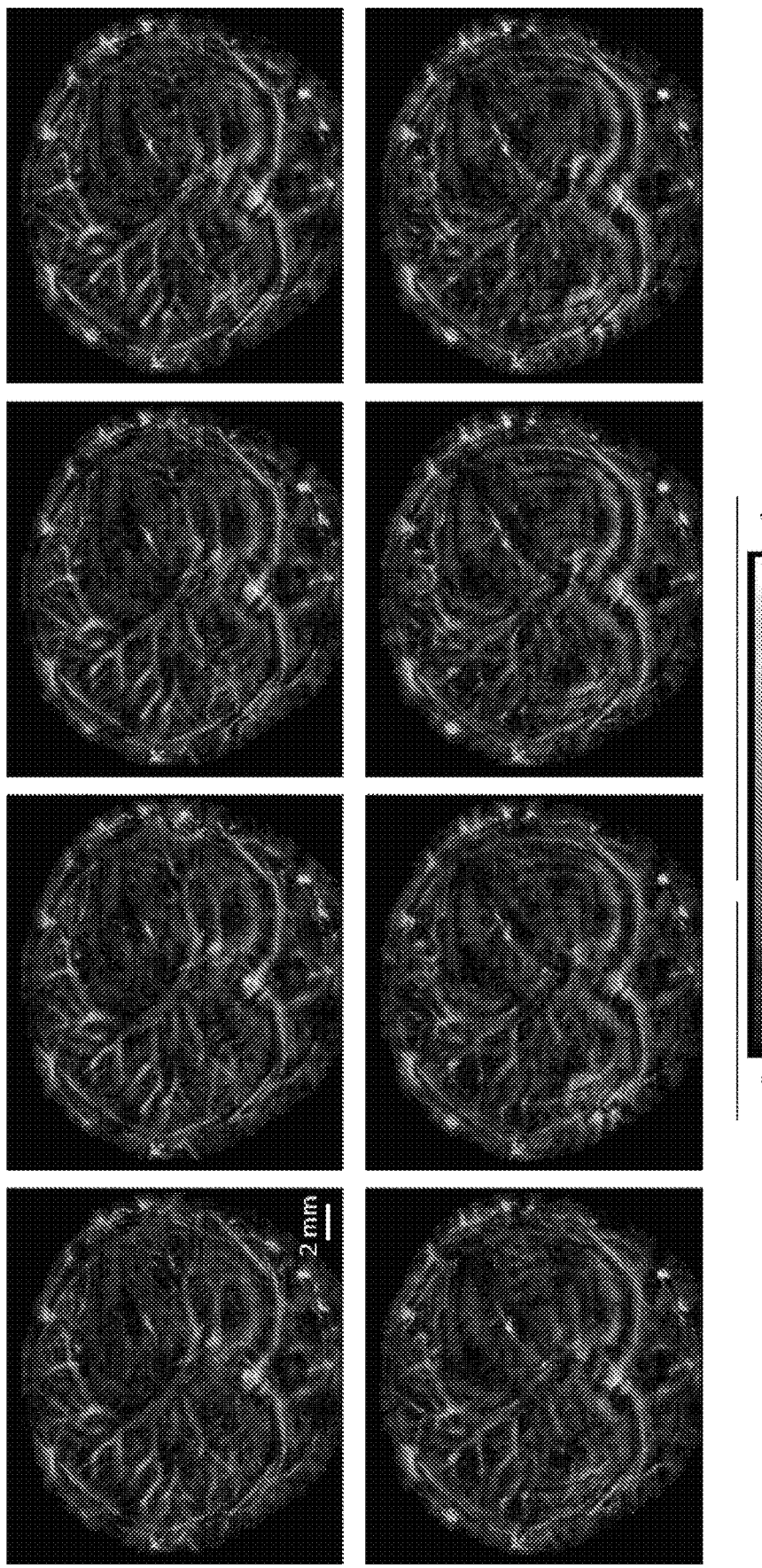
FIG. 32 is a series of eight consecutive images acquired by the SIP-PACT system.
Figure 34:
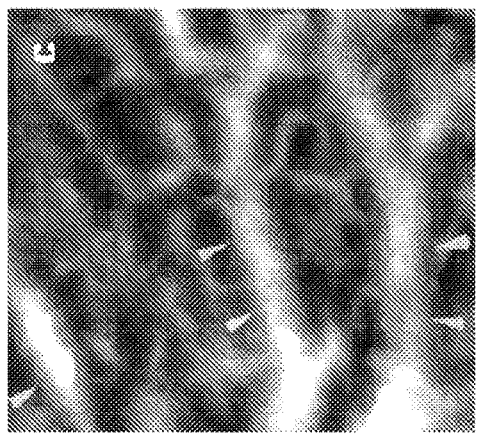
FIG. 34 is an enlargement of a portion of the image of FIG. 33 within the dashed box.
Figure 36:
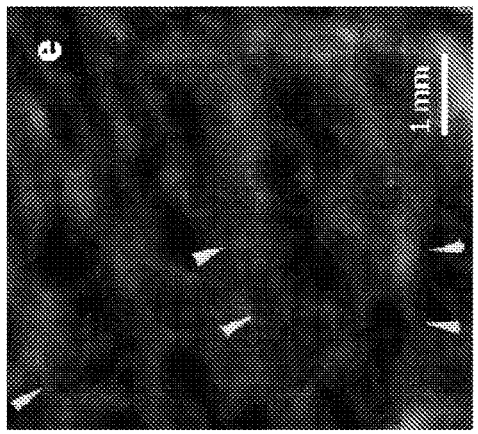
FIG. 36 is an enlargement of a portion of the image of FIG. 35 within the dashed box.

Eight consecutive images were acquired by the SIP-PACT system (see FIG. 32), shown left to right in two rows. A close-up of the first image (see FIG. 33) and an enlargement of a portion of the image of FIG. 33 (see FIG. 34) were obtained. A comparison image (see FIG. 35) and corresponding close-up image (see FIG. 36) were obtained by simulating an 8-to-1 multiplexing using the raw data for the images in FIG. 32. Arrows overlaid on FIGS. 33, 34, 35, and 36 denote features visible in the SIP-PACT images of FIGS. 33 and 34 but are but missing in the simulated multiplexed PACT images of FIGS. 35 and 36.

Figure 33:
FIG. 33 is the SIP-PACT image corresponding to the first image from the series of images of FIG. 32.
Figure 35:
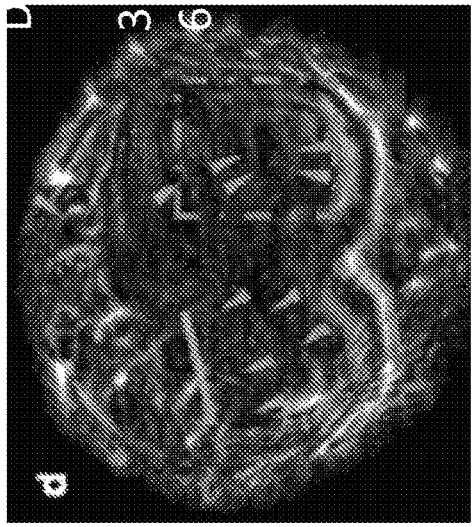
FIG. 35 is a PACT image reconstructed from data produced by an 8:1 multiplexing simulation using the raw data from FIG. 33.
Figure 37:
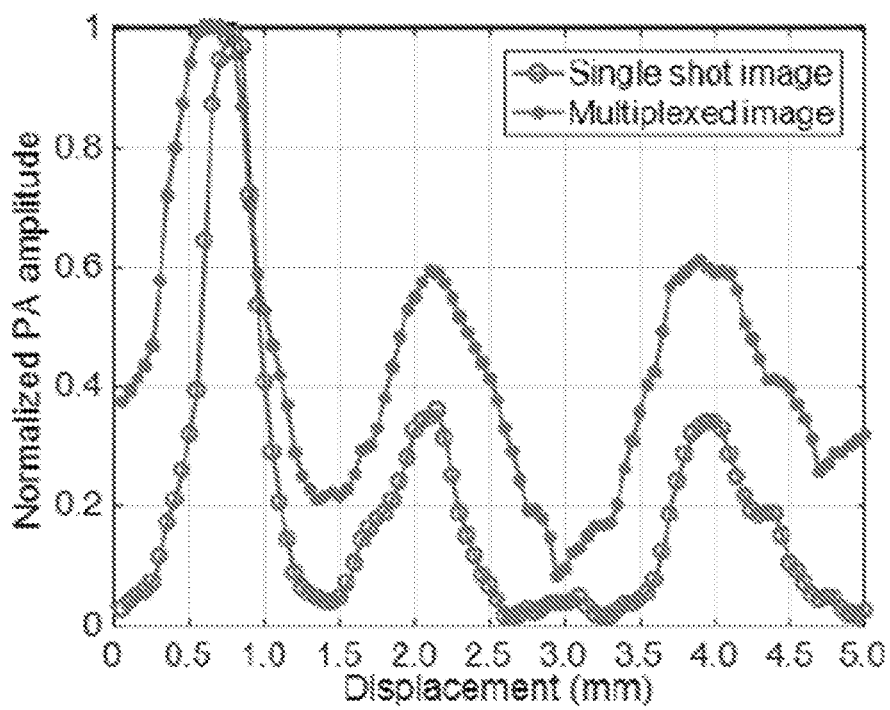
FIG. 37 is a graph showing the PA signal amplitude profiles along a linear transect denoted by overlaid lines in FIG. 33 and FIG. 35.
Figure 38:
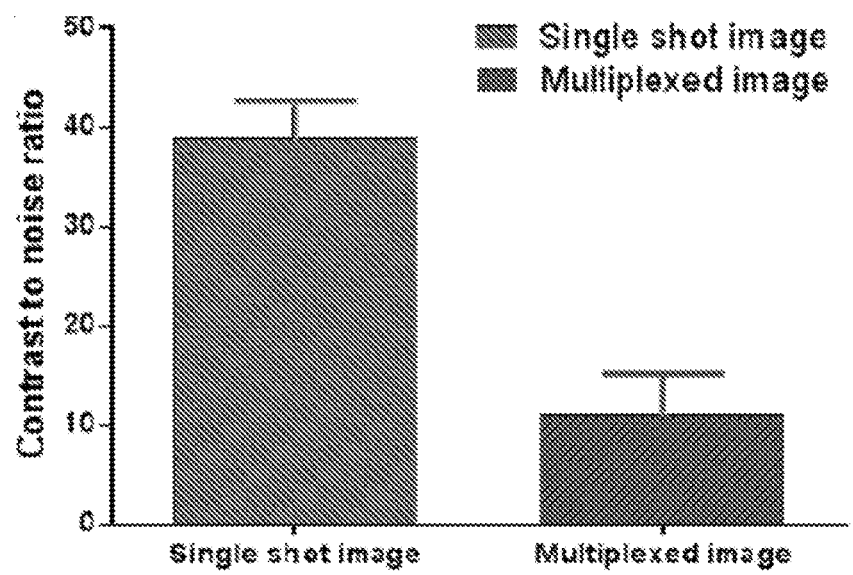
FIG. 38 is a graph comparing the contrast to noise ratios of a SIP-PACT image and a PACT image obtained using simulated multiplexing.
Figures 39A, 39B, 39C, 39D:
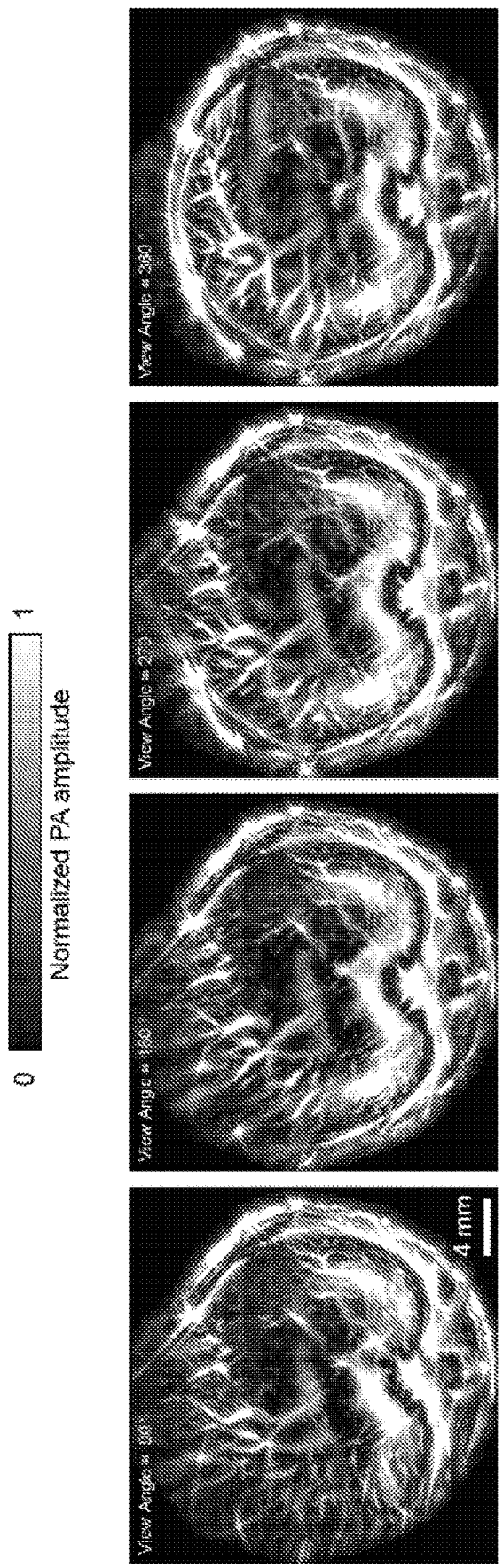
FIG. 39A is a SIP-PACT image reconstructed with a detection view angle of 90°.
FIG. 39B is a SIP-PACT image reconstructed with a detection view angle of 180°.
FIG. 39C is a SIP-PACT image reconstructed with a detection view angle of 270°.
FIG. 39D is a SIP-PACT image reconstructed with a detection view angle of 360°.

FIG. 37 shows PA signal profiles along transects denoted by overlaid lines in in FIG. 33 and FIG. 35. The data of FIG. 37 demonstrate that multiplexing blurs the imaged vessels and degrades image resolution. FIG. 38 shows a comparison of the contrast-to-noise ratios of the images in FIG. 33 and FIG. 35. The data of FIG. 38 demonstrates that PA signal multiplexing degraded the reconstructed image contrast.

Example 13: Effect of Detection View Angle on Image Quality of SIP-PACT

To assess the effect of view angle of the ultrasound detector array on image quality of the SIP-PACT system as described above, the following experiments were conducted.

FIGS. 39A, 39B, 39C, and 39D are SIP-PACT images reconstructed assuming transducer array detection angles of 90□, 180□, 270□, and 360□, respectively. The reconstructed images demonstrate that more structures are discernable with fewer reconstruction artifacts as the transducer array detection angles increases. With a 360□ (full-view) view angle, the reconstructed image had the best image quality and least streaking artifacts. All images were reconstructed using the half-time dual-speed-of-sound universal back-projection method.

To assess the sensitivity of the image quality degradation due to detection view angle with respect to different image reconstruction algorithms. SIP-PACT images were reconstructed using the full-time dual-speed-of-sound universal back-projection method for 360-degree detection view angle (FIG. 40A) and for 270-degree detection view angle (FIG. 40B). The arrows in FIG. 40A point out the missing features in the limited view angle image of FIG. 40B, while the arrows in FIG. 40B point out reconstruction artifacts induced by the limited view angle. FIG. 40C is a differential image between FIG. 40A and FIG. 40B. A threshold of zero was applied to the differential image of FIG. 40C so that only the positive differential values are shown to highlight the features in FIG. 40A that are missing in FIG. 40B.

In addition, SIP-PACT images were reconstructed using the half-time dual-speed-of-sound universal back-projection method for 360-degree detection view angle (FIG. 40D) and for 270-degree detection view angle (FIG. 40E). The arrows in FIG. 40D point out the missing features in the limited view angle image of FIG. 40E, while the arrows in FIG. 40E point out reconstruction artifacts induced by the limited view angle. FIG. 40F is a differential image between FIG. 40D and FIG. 40E. A threshold of zero was applied to the differential image of FIG. 40F so that only the positive differential values are shown to highlight the features in FIG. 40A that are missing in FIG. 40B. FIG. 40G is a differential image between the images of FIG. 40A and FIG. 40D, demonstrating that the half-time dual-speed-of-sound universal back-projection reconstruction method minimized the reconstruction artifacts induced by PA signals reflected multiple times by the bones inside the animal.

The results of this experiment demonstrated that a combination of full-view detection and half-time dual-speed-of-sound universal back-projection reconstruction enhanced SIP-PACT image quality.

Example 14: Validation of SIP-PACT Measurements of Breathing Motion and Heartbeats To validate the breathing motion and heartbeats detected by analysis of SIP-PACT images as described above, the following experiments were conducted.

Figure 41C:
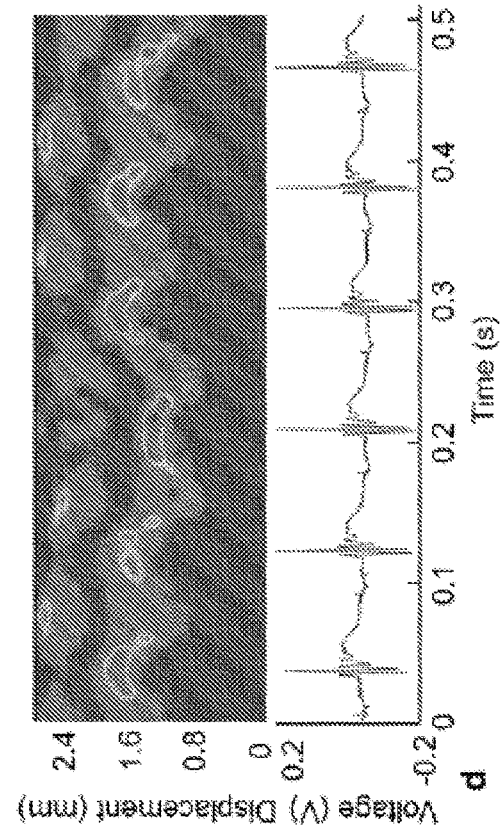
FIG. 41C shows co-registered measurements of a spatiotemporal map of heartbeats from SIP-PACT images (top graph) and from ECG measurements (bottom graph).
Figure 41A:
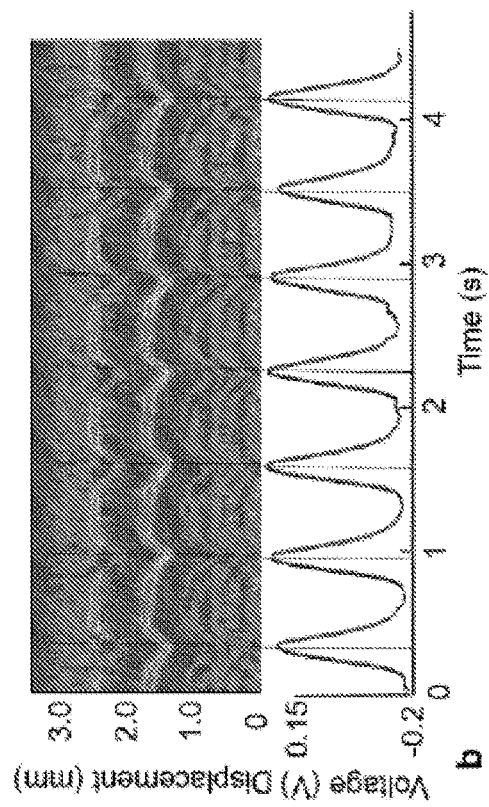
FIG. 41A shows co-registered measurement of a spatiotemporal map of breathing motion from SIP-PACT images (top graph) and from pressure sensor measurements (bottom graph).
Figure 41D:
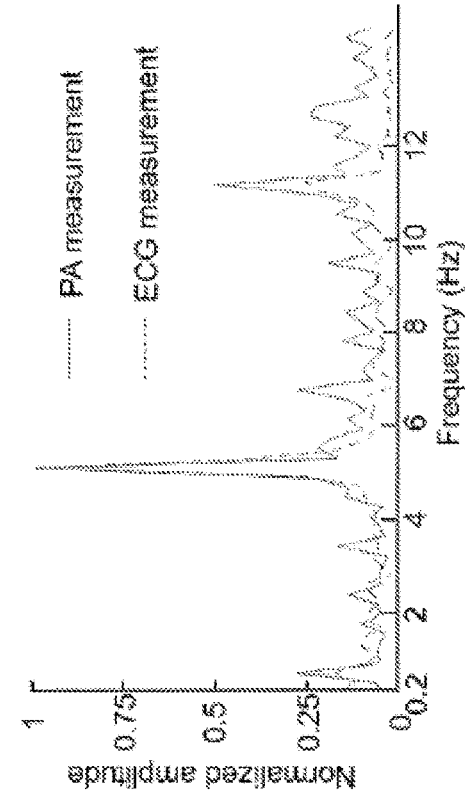
FIG. 41D shows a Fourier transform of the spatiotemporal map and ECG measurements of FIG. 41C.
Figure 41B:
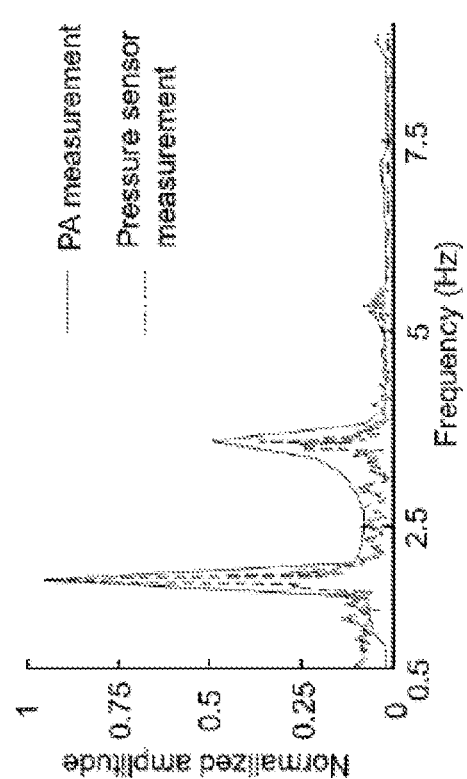
FIG. 41B shows a Fourier transform of the spatiotemporal map and pressure sensor measurements of FIG. 41A.
Figure 43:
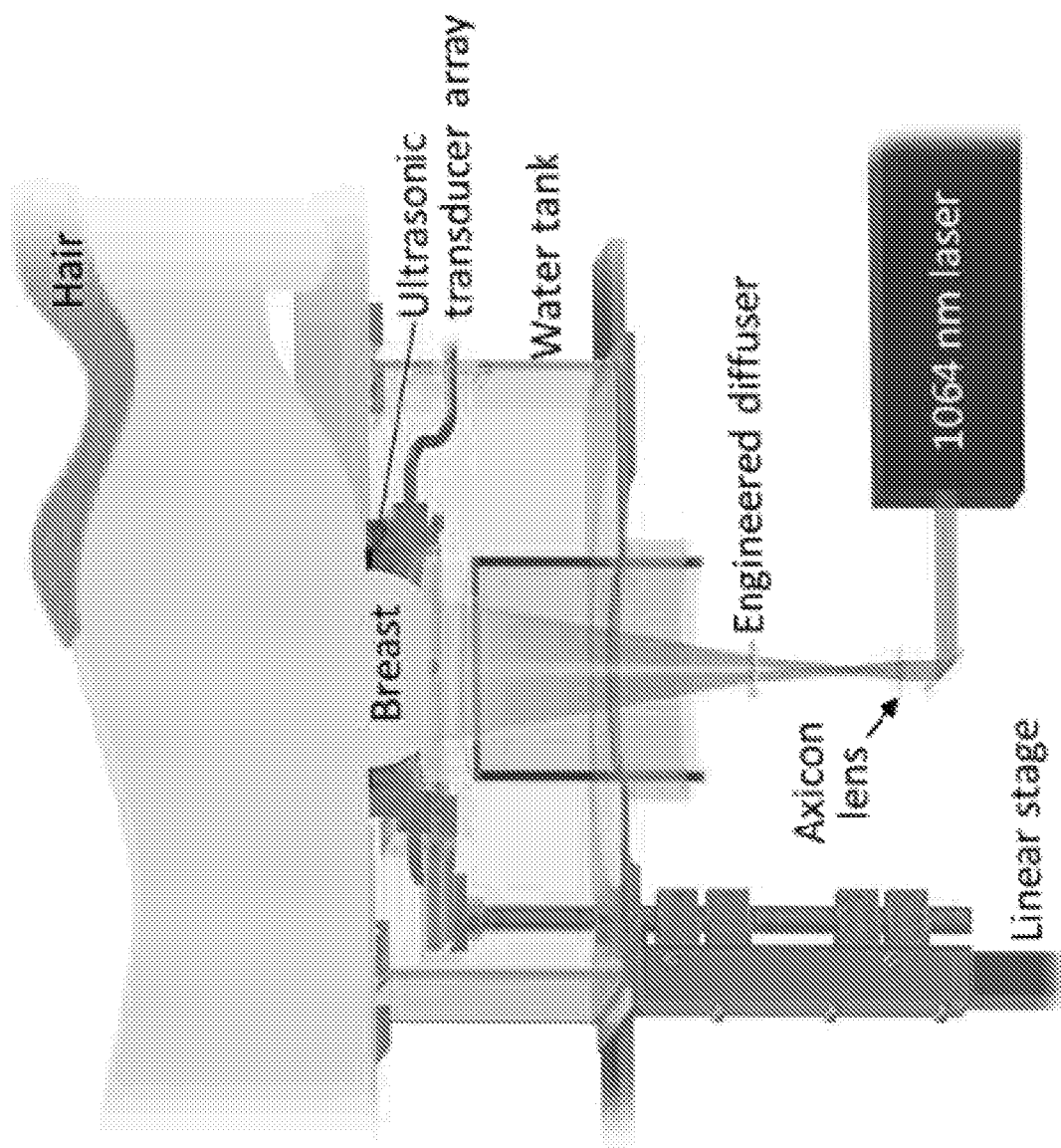
FIG. 43 is a schematic illustration of a SBH-PACT breast imaging system.

SIP-PACT imaging was performed as described above on a mouse, along with pressure sensor and electrocardiography (ECG) measurements conducted in parallel with the SIP-PACT imaging on the same mouse. FIG. 41A shows co-registered measurement of a spatiotemporal map of breathing motion from SIP-PACT images (top graph) and from pressure sensor measurements (bottom graph). FIG. 41B shows a Fourier transform of the spatiotemporal map and pressure sensor measurements of FIG. 41A showing the identical respiratory frequency measured by SIP-PACT and the pressure sensor. FIG. 41C shows co-registered measurements of a spatiotemporal map of heartbeats from SIP-PACT images (top graph) and from ECG measurements (bottom graph). FIG. 41D shows a Fourier transform of the spatiotemporal map and ECG measurements of FIG. 41C showing the identical heartbeats measured by SIP-PACT and the ECG measurements.

Example 15: Effect of Frame Rate on Respiratory Rate and Heart Rate Measured by SIP-PACT To assess the effect of frame rate on respiratory rate and heart rate measured by SIP-PACT, the following experiments were conducted.

A time-series of cross-sectional SIP-PACT images of an upper thoracic cavity similar to the image shown in FIG. 42A were obtained at frame rates of 50 Hz and 10 Hz. Transects crossing a rib and a heart wall were defined within the images, as denoted by lines overlaid on FIG. 42A. PA signal data were extracted along the transects from each series and analyzed to determine breathing rate and heartbeat as described above. FIG. 42B is a spatiotemporal map of the PA signal data extracted along the transects from the 50-Hz frame rate data, showing the displacements of the rib during respiration and the heart wall during heartbeats. FIG. 42C is a spatiotemporal map of the PA signal data extracted along the transects from the 10-Hz frame rate data, showing the displacements of the rib during respiration and the heart wall during heartbeats. FIG. 42D is a graph showing Fourier transforms of the rib and heart wall movements from the 50-Hz spatiotemporal map of FIG. 42B showing the respiratory frequency and heartbeat frequency. FIG. 42E is a graph showing Fourier transforms of the rib and heart wall movements from the 10-Hz spatiotemporal map of FIG. 42C showing the respiratory frequency and the heartbeat frequency aliased due to the low frame rate.

The results of this experiment demonstrated that higher frame rates resulted in the reduction of aliasing and other inaccuracies in SIP-PACT-based measurements of physiological activities.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A photoacoustic computed tomography (PACT) system for producing a 2D or 3D image of at least a portion of a subject, the PACT system comprising:
a light source configured to direct a light pulse into an imaging plane passing through the at least a portion of the subject, wherein a plurality of photoacoustic signals is produced within the imaging plane in response to illumination by the light pulse; and
a full-ring transducer array comprising a plurality of ultrasound transducers, the plurality of ultrasound transducers distributed around a circumference of a ring surrounding the imaging plane, wherein the full-ring transducer array is configured to spatially sample the plurality of photoacoustic signals and wherein the full-ring transducer array is configured to spatially sample a portion of the plurality of photoacoustic signals originating from within a field of view positioned within the imaging plane, the field of view comprising a diameter selected to satisfy a criterion based on a number of the plurality of ultrasound transducers and a wavelength of a high cut-off frequency of the plurality of ultrasound transducers such that a product of the diameter with $\pi$ is less than or equal to a half of a product of the number of the plurality of ultrasound transducers with the wavelength.

2. The PACT system of claim 1, further comprising a plurality of preamplifiers, each pre-amplifier of the plurality of preamplifiers operatively coupled directly to one corresponding ultrasound transducer from the plurality of ultrasound transducers, each preamplifier configured to exclusively amplify the plurality of photoacoustic signals sampled by the one corresponding ultrasound transducer.

3. The PACT system of claim 2, further comprising at least one analog-to-digital sampling device, the at least one analog-to-digital sampling device comprising a plurality of data channels, each data channel of the plurality of data channels operatively coupled to one preamplifier of the plurality of preamplifiers, each data channel of the plurality of data channels configured to exclusively sample and digitize the plurality of the photoacoustic signals amplified by the one preamplifier.

4. The PACT system of claim 3 further comprising a computing device, the computing device comprising at least one processor and a memory storing a plurality of modules, each module comprising instructions executable on the at least one processor, the plurality of modules comprising an image reconstruction module, the image reconstruction module configured to reconstruct the 2D image of the at least a portion of the subject based on the plurality of photoacoustic signals produced in response to illumination by a single light pulse.

5. The PACT system of claim 4, further comprising a scanning element configured to position the full-ring transducer array and the imaging plane at a plurality of positions along a scanning pattern relative to the at least a portion of the subject, wherein:

the light source is further configured to direct a sequence of light pulses into a series of imaging planes, wherein each light pulse of the sequence of light pulses is directed into one imaging plane of the series of imaging planes, each imaging plane positioned at one position of the plurality of positions along the scanning pattern;

the full-ring transducer array is further configured to spatially sample a plurality of photoacoustic signal sets, each photoacoustic signal set comprising the plurality of photoacoustic signals produced at one imaging plane of the series of imaging planes;

the image reconstruction module is further configured to reconstruct a series of 2D images of the at least a portion of the subject, each 2D image of the series of 2D images based on one photoacoustic signal set sampled from one imaging plane of the series of imaging planes; and the image reconstruction module is further configured to reconstruct the 3D image of the at least a portion of the subject based on a combined plurality of photoacoustic signals, the combined plurality of photoacoustic signals comprising the pluralities of photoacoustic signals from the plurality of photoacoustic signal sets sampled at the series of imaging planes;

wherein the image reconstruction module reconstructs the 2D or 3D image of the at least a portion of the subject using a dual speed-of-sound universal back-projection reconstruction algorithm.

6. The PACT system of claim 4, wherein:

the light source is further configured to direct a sequence of light pulses into the imaging plane, the sequence of light pulses produced at a light pulse frequency;

the full-ring transducer array is further configured to spatially sample a plurality of photoacoustic signal sets, each photoacoustic signal set comprising the plurality of photoacoustic signals produced in response to illumination of the imaging plane by each light pulse of the sequence of light pulses; and the image reconstruction module is further configured to reconstruct a time-series of 2D images of the at least a portion of the subject within the imaging plane, each 2D image of the time-series of 2D images based on one photoacoustic signal set.

7. The PACT system of claim 6, wherein the plurality of modules further comprises a motion contrast module configured to produce a motion contrast image based on the time-series of 2D images, wherein the motion contrast module is further configured to:

pixel-wise obtain a plurality of temporal frequency spectra, each temporal frequency spectrum based on fluctuations of a photoacoustic signal amplitude obtained from corresponding pixels within each 2D image of the time-series of 2D images;

select a peak magnitude of photoacoustic signal amplitude within a preselected frequency range from each temporal frequency spectrum; and producing the motion contrast image by pixel-wise assigning each selected peak magnitude of photoacoustic signal amplitude within the preselected frequency range to each corresponding pixel of the time-series of 2D images;

wherein the image reconstruction module reconstructs the 2D or 3D images of the at least a portion of the subject using a dual speed-of-sound universal back-projection reconstruction algorithm.

8. The PACT system of claim 6, wherein the plurality of modules further comprises a multiscale vessel enhancing filtering module configured to enhance an image contrast in the 2D or 3D images produced by the PACT system, wherein the multiscale vessel enhancing filtering module is further configured to:

apply a set of Hessian-based Frangi vesselness filters at one or more different scales to produce a set of filtered images, wherein the one or more different scales are chosen to cover a range of about 1.2 to about 10 times a resolution of the PACT system; and averaging the set of filtered images to produce a 2D or 3D image with enhanced contrast.

9. The PACT system of claim 6, wherein the plurality of modules further comprises a motion analysis module configured to calculate a motion of at least one detected structure along a preselected transect within the time-series of 2D images, wherein the motion analysis module is further configured to:

extract a plurality of photoacoustic signal transects from the time-series of 2D images, each photoacoustic signal transect comprising a group of photoacoustic signal magnitudes corresponding to a group of pixels positioned along the preselected transect within each 2D image of the time-series of 2D images;

assemble the plurality of photoacoustic signal transects to form a spatiotemporal map, the spatiotemporal map comprising a plurality of pixel rows, each pixel row comprising a photoacoustic signal transect, wherein a horizontal axis of the spatiotemporal map is indicative of an imaging time associated with each 2D image of the time-series of 2D images, and a vertical axis of the spatiotemporal map is indicative of a pixel distance along the preselected transect;

track a position of at least one maximum photoacoustic signal within the spatiotemporal map, the at least one maximum photoacoustic signal indicative of the at least one detected structure;

perform a 2D Fourier transformation of the spatiotemporal map to produce a spectral map, the spectral map comprising a plurality of pixel rows, each pixel row comprising a series of normalized spectral amplitudes wherein a horizontal axis of the spectral map is indicative of a spatial frequency, and a vertical axis of the spectral map is indicative of a temporal frequency; and calculate a slope of a plurality of maximum spectral amplitudes within the spectral map, the slope indicative of a speed of the motion of the at least one detected structure.

10. The PACT system of claim 6, wherein the plurality of modules further comprises a sparse sampling correction module configured to reduce image artifacts associated with sparse data sampling within a portion of the imaging plane outside of the field of view of the full-ring transducer array, wherein the sparse sampling correction module is further configured to:

produce at least one plurality of filtered photoacoustic signals by filtering the plurality of photoacoustic signals using a low-pass filter with a selected cutoff frequency, the selected cutoff frequency corresponding to an enlarged field of view relative to the field of view determined by the criterion, wherein the selected cutoff frequency is less than the high cut-off frequency of the full-ring transducer array associated with the field of view, and the enlarged field of view contains the field of view;
reconstruct at least one additional 2D image, each additional image of the at least one additional 2D image reconstructed using each plurality of filtered photoacoustic signals of the at least one plurality of filtered photoacoustic signals;
produce at least one blurred mask, wherein each blurred mask of the at least one blurred mask is produced by selecting and blurring a portion of each enlarged field of view positioned outside of any smaller enlarged field of views within each enlarged field of view;
multiply each additional 2D image by the corresponding blurred mask to produce each masked 2D image of at least one masked 2D image; and
add the at least one masked 2D image to produce a final 2D image, the final 2D image characterized by reduced artifacts associated with sparse sampling relative to the 2D image produced by the image reconstruction module.

11. The PACT system of claim 1, wherein the at least a portion of the subject is selected from the group consisting of: a brain, a breast, an abdominal cavity, a thoracic cavity, a pleural cavity, a hand, a foot, an arm, a leg, a finger, a toe, and a penis.

12. The PACT system of claim 1, further comprising a computing device, the computing device comprising at least one processor and a memory storing a plurality of modules, each module comprising instructions executable on the at least one processor, the plurality of modules comprising an image reconstruction module, the image reconstruction module configured to:
provide a speed-of-sound map representing a spatial distribution of a first speed-of-sound $V_1$ and a second speed-of-sound $V_2$ within an imaging region of the PACT system, the speed-of-sound map comprising an elliptical tissue region positioned within a circular water region;
for each combination of a plurality of photoacoustic signal source positions and a plurality of detector positions within the speed-of-sound map:
calculate a total distance L of a signal path from each photoacoustic signal source position to each detector position;
calculate a first distance $L_1$ from each photoacoustic signal source position to an intersection point of the signal path with a tissue-water interface comprising a boundary enclosing the elliptical tissue region on the speed-of-sound map;
calculate a second distance $L_2$ from the intersection point to each detector position by subtracting $L_1$ from L; and
calculate a delay time $t_{delay}$ according to Eqn. (12), the delay time $t_{delay}$ comprising a sum of a first time to travel at the first speed-of-sound $V_1$ through the elliptical tissue region and a second time to travel at the second speed-of-sound $V_2$- through the circular water region:

$$t_{delay} = \frac{L_1}{V_1} + \frac{L_2}{V_2} \qquad \text{Eqn. (12)}$$

combine all $t_{delays}$ to form a dual-speed-of-sound delay map comprising each $t_{delay}$ and each corresponding photoacoustic signal source position and detector position; and
reconstruct the 2D image using a universal back-projection method with the dual-speed-of-sound delay map.

13. The PACT system of claim 12, wherein each photoacoustic signal of the plurality of photoacoustic signals is assumed to travel in a linear path from each photoacoustic signal source position to each detector position without refraction at the tissue-water interface.

14. The PACT system of claim 12, wherein the image reconstruction module further configured to:
provide a series of speed of sound maps, each speed of sound map corresponding to a vertical position of a series of vertical positions of an detector array, wherein series of photoacoustic signal sets is obtained by the detector array positioned at the series of vertical positions of the detector array, each photoacoustic signal set comprising a portion of the plurality of photoacoustic signals;
form a series of dual-speed-of-sound delay maps, each dual-speed-of-sound delay map of the series of dual-speed-of-sound delay maps corresponding to each speed of sound map of the series of speed of sound maps; and
reconstruct a 3D image from the series of photoacoustic signal sets using the universal back-projection method with the series of dual-speed-of-sound delay maps.

15. A photoacoustic computed tomography (PACT) system for producing a 2D or 3D image of a breast of a subject, the PACT system comprising:
a light source configured to direct a light pulse into an imaging plane passing through the breast of the subject, wherein a plurality of photoacoustic signals is produced within the imaging plane in response to illumination by the light pulse; and
a full-ring transducer array comprising a plurality of ultrasound transducers, the plurality of ultrasound transducers distributed around a circumference of a ring surrounding the imaging plane, wherein the full-ring transducer array is configured to spatially sample the plurality of photoacoustic signals and wherein the full-ring transducer array is configured to spatially sample a portion of the plurality of photoacoustic signals originating from within a field of view positioned within the imaging plane, the field of view comprising a diameter selected to satisfy
a criterion based on a number of the plurality of ultrasound transducers and a wavelength of a high cut-off frequency of the plurality of ultrasound transducers such that a product of the diameter with $\pi$ is less than or equal to a half of a product of the number of the plurality of ultrasound transducers with the wavelength.

16. The PACT system of claim 15, further comprising:
a plurality of preamplifiers, each pre-amplifier of the plurality of preamplifiers operatively coupled directly to one corresponding ultrasound transducer from the plurality of ultrasound transducers, each preamplifier configured to exclusively amplify the plurality of photoacoustic signals sampled by the one corresponding ultrasound transducer; and
at least one analog-to-digital sampling device, the at least one analog-to-digital sampling device comprising a plurality of data channels, each data channel of the plurality of data channels operatively coupled to one preamplifier of the plurality of preamplifiers, each data channel of the plurality of data channels configured to exclusively sample and digitize the plurality of the photoacoustic signals amplified by the one preamplifier.

17. The PACT system of claim 16, wherein:
the light source is further configured to direct a sequence of light pulses into the imaging plane, the sequence of light pulses produced at a light pulse frequency; and
the full-ring transducer array is further configured to spatially sample a plurality of photoacoustic signal sets, each photoacoustic signal set comprising the plurality of photoacoustic signals produced in response to illumination of the imaging plane by each light pulse of the sequence of light pulses.

18. The PACT system of claim 17, further comprising a linear scanning stage configured to position the full-ring transducer array and the imaging plane at a plurality of positions along a scanning pattern relative to the breast of the subject, wherein:
the light source is further configured to direct the sequence of light pulses into a series of imaging planes, wherein each light pulse of the sequence of light pulses is directed into one imaging plane of the series of imaging planes, each imaging plane positioned at one position of the plurality of positions along the scanning pattern; and
each photoacoustic signal set comprising the plurality of photoacoustic signals is produced at one imaging plane of the series of imaging planes.

19. The PACT system of claim 18, further comprising a computing device, the computing device comprising at least one processor and a memory storing a plurality of modules, each module comprising instructions executable on the at least one processor, the plurality of modules comprising an image reconstruction module, the image reconstruction module configured to reconstruct, using a dual speed-of-sound universal back-projection reconstruction algorithm, at least one of:
a 2D image of the breast at a single imaging plane based on the plurality of photoacoustic signals produced in response to illumination by a single light pulse;
a series of 2D images of the breast, each 2D image of the series of 2D images based on one photoacoustic signal set sampled from one imaging plane of the series of imaging planes;
a time-series of 2D images of the breast of the subject within the single imaging plane, each 2D image of the time-series of 2D images based on one photoacoustic signal set; and
a 3D image of the breast based on a combined plurality of photoacoustic signals, the combined plurality of photoacoustic signals comprising the pluralities of photoacoustic signals from the plurality of photoacoustic signal sets sampled at the series of imaging planes.

20. The PACT system of claim 19, further comprising:
an imaging bed comprising a support surface and an opening formed through the support surface, the opening configured to receive the breast of the subject when the subject is positioned prone on the support surface of the imaging bed; and
a water tank coupled to the opening opposite to the support surface of the imaging bed, the water tank containing an amount of water and the full-ring transducer array;
wherein the breast of the subject is positioned within the full-ring transducer array at the imaging plane.

* * * * *